US006761888B1

(12) United States Patent
Schenk

(10) Patent No.: US 6,761,888 B1
(45) Date of Patent: *Jul. 13, 2004

(54) PASSIVE IMMUNIZATION TREATMENT OF ALZHEIMER'S DISEASE

(75) Inventor: Dale B. Schenk, Burlingame, CA (US)

(73) Assignee: Neuralab Limited (BM)

( * ) Notice: Subject to any disclaimer, the term of this patent is extended or adjusted under 35 U.S.C. 154(b) by 0 days.

This patent is subject to a terminal disclaimer.

(21) Appl. No.: 09/580,018

(22) Filed: May 26, 2000

(51) Int. Cl.[7] .................. C07K 16/00; C07K 16/18; A61K 39/00
(52) U.S. Cl. ................ 424/130.1; 530/300; 530/350; 530/387.1
(58) Field of Search ............................ 530/300, 350, 530/387.1; 424/130.1, 131.1, 141.1, 141.2

(56) References Cited

U.S. PATENT DOCUMENTS

| | | |
|---|---|---|
| 4,666,829 A | 5/1987 | Glenner et al. |
| 4,713,366 A | 12/1987 | Stevens |
| 5,004,697 A | 4/1991 | Pardridge |
| 5,057,540 A | 10/1991 | Kensil et al. |
| 5,187,153 A | 2/1993 | Cordell et al. |
| 5,192,753 A | 3/1993 | McGeer et al. |
| 5,208,036 A | 5/1993 | Eppstein et al. |
| 5,220,013 A | 6/1993 | Ponte et al. |
| 5,231,000 A | 7/1993 | Majocha et al. |
| 5,231,170 A | 7/1993 | Averback |
| 5,270,165 A | 12/1993 | Van Nostrand et al. |
| 5,387,742 A | 2/1995 | Cordell |
| 5,434,170 A | 7/1995 | Andrulis et al. |
| 5,441,870 A | 8/1995 | Seubert et al. |
| 5,464,823 A | 11/1995 | Lehrer et al. |
| 5,571,499 A | 11/1996 | Hafler et al. |
| 5,571,500 A | 11/1996 | Hafler et al. |
| 5,583,112 A | 12/1996 | Kensil et al. |
| 5,585,100 A | 12/1996 | Mond et al. |
| 5,593,846 A | 1/1997 | Schenk et al. |
| 5,605,811 A | 2/1997 | Seubert et al. |
| 5,612,486 A | 3/1997 | McConlogue et al. |
| 5,622,701 A | 4/1997 | Berg |
| 5,641,473 A | 6/1997 | Hafler et al. |
| 5,641,474 A | 6/1997 | Hafler et al. |
| 5,645,820 A | 7/1997 | Hafler et al. |
| 5,679,348 A | 10/1997 | Nesburn et al. |
| 5,688,651 A | 11/1997 | Solomon |
| 5,721,130 A | 2/1998 | Seubert et al. |
| 5,733,547 A | 3/1998 | Weiner et al. |
| 5,736,142 A | 4/1998 | Sette et al. |
| 5,744,368 A | 4/1998 | Goldgaber et al. |
| 5,750,349 A | 5/1998 | Suzuki et al. |
| 5,750,361 A | 5/1998 | Prusiner et al. |
| 5,753,624 A | 5/1998 | McMichael et al. |
| 5,776,468 A | 7/1998 | Hauser et al. |
| 5,780,587 A | 7/1998 | Potter |
| 5,786,180 A | 7/1998 | Konig et al. |
| 5,824,322 A | 10/1998 | Balasubramanlan |
| 5,837,473 A | 11/1998 | Maggio et al. |
| 5,837,672 A | 11/1998 | Schenk et al. |
| 5,846,533 A | 12/1998 | Prusiner |
| 5,849,298 A | 12/1998 | Weiner et al. |
| 5,851,996 A | 12/1998 | Kline |
| 5,854,204 A | 12/1998 | Findeis et al. |
| 5,869,054 A | 2/1999 | Weiner et al. |
| 5,869,093 A | 2/1999 | Weiner et al. |
| 5,877,399 A | 3/1999 | Hsiao et al. |
| 5,935,927 A | 8/1999 | Vitek et al. |
| 5,955,079 A | 9/1999 | Mond et al. |
| 5,955,317 A | 9/1999 | Suzuki et al. |
| 5,958,883 A | 9/1999 | Snow |
| 5,989,566 A | 11/1999 | Cobb et al. |
| 6,057,367 A | 5/2000 | Stamler et al. |
| 6,114,133 A | 9/2000 | Seubert et al. |
| 6,150,091 A | 11/2000 | Pandolfo et al. |
| 6,262,335 B1 | 7/2001 | Hsiao et al. |
| 6,284,221 B1 | 9/2001 | Schenk et al. |
| 6,284,533 B1 | 9/2001 | Thomas |
| 6,294,171 B2 | 9/2001 | McMichael |
| 6,399,314 B1 | 6/2002 | Krishnamurthy |
| 6,417,178 B1 | 7/2002 | Klunk et al. |
| 2001/0018053 A1 | 8/2001 | McMichael |
| 2001/0021769 A1 | 9/2001 | Prusiner |
| 2002/0009445 A1 | 1/2002 | Du et al. |
| 2002/0077288 A1 | 6/2002 | Frangione |
| 2002/0086847 A1 | 7/2002 | Chain |
| 2002/0094335 A1 | 7/2002 | Chalifour et al. |
| 2002/0102261 A1 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |

(List continued on next page.)

FOREIGN PATENT DOCUMENTS

| | | |
|---|---|---|
| EP | 451 700 | 10/1991 |
| EP | 276 723 | 12/1993 |
| EP | 613 007 | 8/1994 |
| EP | 666 080 | 8/1995 |
| EP | 359 783 | 11/1995 |

(List continued on next page.)

OTHER PUBLICATIONS

Andersen et al., "Do nonsteroidal anti–inflammatory drugs decrease the risk for Alzheimer's disease?," *Neurology*, 45:1441–1445 (1995).

(List continued on next page.)

*Primary Examiner*—Gary Kunz
*Assistant Examiner*—Christopher James Nichols
(74) *Attorney, Agent, or Firm*—Townsend and Townsend and Crew LLP

(57) ABSTRACT

The invention provides improved agents and methods for treatment of diseases associated with amyloid deposits of Aβ in the brain of a patient. Such methods entail administering agents that induce a beneficial immunogenic response against the amyloid deposit. The methods are useful for prophylactic and therapeutic treatment of Alzheimer's disease. Preferred agents including N-terminal fragments of Aβ and antibodies binding to the same.

36 Claims, 18 Drawing Sheets

U.S. PATENT DOCUMENTS

| | | |
|---|---|---|
| 2002/0162129 A1 | 10/2002 | Lannfelt |
| 2002/0168377 A1 | 11/2002 | Schaetzl |
| 2002/0187157 A1 | 12/2002 | Jensen et al. |
| 2002/0197258 A1 | 12/2002 | Ghanbari et al. |
| 2003/0068325 A1 | 4/2003 | Wang |
| 2003/0073655 A1 | 4/2003 | Chain |

FOREIGN PATENT DOCUMENTS

| | | |
|---|---|---|
| EP | 683 234 | 11/1995 |
| EP | 440 619 | 1/1996 |
| EP | 526 511 | 5/1997 |
| EP | 782 859 | 7/1997 |
| EP | 783 104 A1 | 7/1997 |
| EP | 594 607 | 8/1997 |
| EP | 845 270 | 6/1998 |
| EP | 863 211 | 9/1998 |
| EP | 868 918 | 10/1998 |
| EP | 652 962 | 12/1998 |
| EP | 911 036 | 4/1999 |
| EP | 561 087 | 8/1999 |
| EP | 639 081 | 11/1999 |
| EP | 506 785 | 3/2000 |
| EP | 1 172 378 A1 | 1/2002 |
| GB | 2 220 211 | 1/1990 |
| GB | 2 335 192 | 9/1999 |
| WO | WO 88/10120 | 12/1988 |
| WO | PCT89/01343 A1 | 2/1989 |
| WO | WO 89/03687 | 5/1989 |
| WO | WO 89/06242 | 7/1989 |
| WO | WO 89/06689 | 7/1989 |
| WO | WO 90/12870 | 11/1990 |
| WO | WO 90/12871 | 11/1990 |
| WO | WO 91/08760 | 6/1991 |
| WO | WO 91/12816 | 9/1991 |
| WO | WO 91/16819 | 11/1991 |
| WO | WO 91/19810 | 12/1991 |
| WO | WO 92/06187 | 4/1992 |
| WO | WO 92/06708 | 4/1992 |
| WO | WO 92/13069 | 8/1992 |
| WO | WO 93/02189 | 2/1993 |
| WO | PCT93/04194 | 3/1993 |
| WO | WO 93/14200 | 7/1993 |
| WO | WO 93/15760 | 8/1993 |
| WO | WO 93/16724 | 9/1993 |
| WO | WO 93/21950 | 11/1993 |
| WO | WO 94/01772 | 1/1994 |
| WO | WO 94/03615 | 2/1994 |
| WO | PCT94/28412 A1 | 12/1994 |
| WO | WO 95/04151 | 2/1995 |
| WO | WO 95/05853 | 3/1995 |
| WO | WO95/11008 A2 | 4/1995 |
| WO | WO 95/11311 | 4/1995 |
| WO | WO 95/11994 | 5/1995 |
| WO | PCT95/12815 A1 | 5/1995 |
| WO | WO 95/31996 | 11/1995 |
| WO | WO 96/18900 | 6/1996 |
| WO | WO 96/25435 | 8/1996 |
| WO | PCT96/28471 A1 | 9/1996 |
| WO | WO 96/39176 | 12/1996 |
| WO | WO 97/10505 A1 | 3/1997 |
| WO | WO 97/17613 | 5/1997 |
| WO | PCT97/21728 A1 | 6/1997 |
| WO | WO 98/07850 | 2/1998 |
| WO | WO 98/44955 | 10/1998 |
| WO | PCT99/00150 A2 | 1/1999 |
| WO | WO 99/06066 | 2/1999 |
| WO | WO 99/27911 | 6/1999 |
| WO | WO 99/27944 | 6/1999 |
| WO | WO 99/27949 | 6/1999 |
| WO | WO99/06545 A2 | 11/1999 |
| WO | WO 99/58564 | 11/1999 |
| WO | WO 99/60021 | 11/1999 |
| WO | WO 99/60024 | 11/1999 |
| WO | WO01/62284 A2 | 3/2000 |
| WO | WO00/43039 A1 | 7/2000 |
| WO | PCT00/43049 A1 | 7/2000 |
| WO | WO00/72870 A1 | 12/2000 |
| WO | PCT00/77178 A1 | 12/2000 |
| WO | WO00/72878A2 A3 | 12/2000 |
| WO | WO00/72880A2 A3 | 12/2000 |
| WO | WO 02/03911 A2 | 4/2001 |
| WO | WO01/42306 A2 | 6/2001 |
| WO | WO01/39796 A2 | 8/2001 |
| WO | WO01/62801 A2 | 8/2001 |
| WO | WO 01/77167 A2 | 10/2001 |
| WO | WO 01/90182 A2 | 11/2001 |
| WO | WO 02/34777 A1 | 5/2002 |
| WO | WO 02/34878 A2 | 5/2002 |

OTHER PUBLICATIONS

Associated Press, "Immune cells may promote Alzheimer's, a study finds," *The Boston Globe* (Apr. 13, 1995).

Bauer et al., "Interlukin–6 and α–2–macroglobulin indicate an acute–phase state in Alzheimer's disease cortices," *FEBS Letters*, 285(1):111–114 (1991).

Blass, John P., "Immunologic Treatment of Alzheimer's Disease," *New England J. Medicine*, 341(22):1694 (1999).

Bodmer et al., "Transforming Growth Factor–Beta Bound to Soluble Derivatives of the Beta Amyloid Precursor Protein of Alzheimer's Disease," *Biochem. Biophys. Res. Comm.*, 171(2):890–897 (1990).

Borchelt et al., "Accelerated Amyloid Deposition in the Brains of Transgenic Mice Coexpressing Mutant Presenilin 1 and Amyloid Precursor Proteins", *Neuron*, 19:939–945 (1997).

Boris–Lawrie et al., Recent advances in retrovirus vector technology, *Cur. Opin. Genet Develop.*, 3: 102–109 (1993).

Brice et al., "Absense of the amyloid precursor protein gene mutation (APP 717 : Val–>Ile) in 85 cases of early onset Alzheimer's disease," *J. Neurology, Neurosurg, Psychiatry*, 56:112–115 (1993).

Chao et al., "Transforming Growth Factor–β Protects human Neurons Against β–Amyloid–Induced Injury," *Soc. Neurosci. Abstracts*, 19:513.7 (1993).

Duff et al., Mouse model made, *Nature*, 373: 476–477 (1995).

Elizan et al., "Antineurofilament antibodies in a postencephalitic and idiopathic parkinson's disease," *J. Neurol. Sciences*, 59:341–347 (1983).

Felsenstein et al., "Processing of the β–amyloid precursor protein carrying the familial, Dutch–type, and a novel recombinant C–terminal mutation," *Neuroscience Letters*, 152:185–189 (1993).

Finch et al., "Evolutionary Perspectives on Amyloid and Inflammatory Features of Alzheimer Disease," *Neurobiology of Aging*, 17(5):809–815 (1996).

Fisher et al., "Expression of the amyloid precursor protein gene in mouse oocytes and embryos," *PNAS*, 88:1779–1782 (1991).

Flanders et al., "Altered expression of transforming growth factor–β in Alzheimer's disease," *Neurology*, 45:1561–1569 (1995).

Games et al., "Alzheimer–type neuropathology in transgenic mice overexpressing V717F β–amyloid precursor protein", *Nature*, 373(6514): 523–527 (1995).

Gandy et al., "Amyloidogenesis in Alzheimer's disease: some possible therapeutic opportunities," *TiPS*, 13:108–113 (1992).

Gaskin et al., "Human antibodies reactive with beta–amyloid protein in Alzheimer's disease," *J. Exp. Med.*, 177:1181–1186 (1993).

Glenn et al., "Skin immunization made possible by cholera toxin", *Nature*, 391: 851 (1998).

Glenner et al., "Alzheimer's Disease: Initial Report of the Purification and Characterization of a Novel Gerebrovascular Amyloid Protein", *Biochemical and Biophysical Research Communications*, 120(3):885–890 (1994).

Glenner et al., "Alzheimer's Disease and Downs Syndrome: Sharing of A Unique Cerebrovascular Amyloid Fibril Protein", *Biochemical and Biophysical Research Communications*, 122(3): 1131–1135 (1984).

Goate et al., "Segregation of a missense mutation in the amyloid precursor protein gene with familial Alzheimer's disease," *Nature*, 349:704–706 (1991).

Gozes et al., "Neuroprotective strategy for Alzheimer disease: Intranasal administration of a fatty neuropeptide," *PNAS*, 93:427–432 (1996).

Gupta et al., "Differences in the immunogenicity of native and formalized cross reacting material (CRM197) of diptheria toxin in mice and guinea pigs and their implications on the development and control of diphteria vaccine based on CRMs", *Vaccine*, 15(12/13):1341–1343 (1997).

Haga et al., "Synthetic Alzheimer amyloid β/A4 peptides enhance production of complement C3 component by cultured microglial cells," *Brain Research*, 601:88–94 (1993).

Hanes et al., "New advances in microsphere–based single-dose vaccines", *Advanced Drug Delivery Reviews*, 28: 97–119 (1997).

Hardy, "Amyloid, the presenilins and Alzheimer's disease", *TINS*, 20(4): 154–159 (1997).

Hardy, John, "New Insights into the Genetics of Alzheimer's Disease," *Annals of Med.*, 28:255–258 (1996).

Hsiao et al., "Correlative Memory Deficits, Aβ Elevation, and Amyloid Plaques in Transgenic Mice", *Science*, 274: 99–102 (1996).

Huberman et al., "Correlation of cytokine secretion by mononuclear cells of Alzheimer's patients and their disease stage," *J. Neuroimmunology*, 52:147–152 (1994).

Hyman et al., "Molecular Epidemiology of Alzheimer's Disease," *N. E. J. Medicine*, 333(19):1283–1284 (1995).

Itagaki et al., "Relationship of microglia and astrocytes to amyloid deposits of Alzheimer's disease," *J. Neuroimmunology*, 24:173–182 (1989).

Jansen et al., "Immunotoxins: Hybrid Molecules Combining High Specificity and Potent Cytotoxicity", *Immun. Rev.*, 62: 185–216 (1982).

Kalaria, R. N., "Serum amyloid P and related molecules associated with the acute–phase response in Alzheimer's disease," *Res. Immunology*, 143:637–641 (1992).

Kawabata et al., "Amyloid plaques, neurofibrillary tangles and neuronal loss in brains of transgenic mice overexpressing a C–terminal fragment of human amyloid precursor protein," *Nature*, 354:476–478 (1991).

Lamper–Etchells et al., "Regional Localization of Cells Containing Complement C1q and C4 mRNAs in the Frontal Cortex During Alzheimer's Disease," *Neurodegeneration*, 2:111–121 (1993).

Langer, "New Methods of Drug Delivery", *Science*, 249: 1527–1532 (1990).

Lannfelt et al., "Alzheimer's disease: molecular genetics and transgenic animal models," *Behavioural Brain Res.*, 57:207–213 (1993).

Lemere et al., "Mucosal Administration of Aβ Peptide Decreases Cerebral Amyloid Burden In Pd–App Transgenic Mice," *Society for Neuroscience Abstracts*, vol. 25, part I, Abstract 519.6, 29th Annual Meetings, 10–23–28/99.

Livingston et al., "The Hepatitis B Virus–Specific CTL Responses Induced in Humans by Lipopeptide Vaccination Are Comparable to Those Elicited by Acute Viral Infection", *J. Immunol.*, 159: 1383–1392 (1997).

Lopez et al., "Serum auto–antibodies in Alzheimer's disease," *Acta. Neurol. Scand.*, 84:441–444 (1991).

McGee et al., "The encapsulation of a model protein in poly (D,L lactide–co–glycolide) microparticles of various sizes: an evaluation of process reproducibility", *J. Micro. Encap.*, 14(2): 197–210 (1997).

Meda et al., "Activation of microglial cells by β–amyloid protein and interferon–γ," *Nature*, 374:647–650 (1995).

Miller et al., "Antigen–driven Bystander Suppression after Oral Administration of Antigens," *J. Exp. Med.*, 174:791–798 (1991).

Nathanson et al., "Bovine Spongiform Encephalopathy (BSE): Causes and Consequences of a Common Source Epidemic", *Am. J. Epidemiol.*, 145(11): 959–969 (Jun. 1, 1997).

New York Times National, "Anti–Inflammatory Drugs May Impede Alzheimer's," (Feb. 20, 1994).

Paresce et al., "Microglial cells influence aggregates of the Alzheimer's disease amyloid beta–protein via a scavenger receptor," *Neuron*, 17:553–565 (Sep. 1996).

Paul et al., "Transdermal immunization with large proteins by means of ultradeformable drug carriers", *Eur. J. Immunol.*, 25: 3521–3524 (1995).

Prieels et al., "Synergistic adjuvants for vaccines", *Chemical Abstracts*, 120(8): p. 652, col. 1, abstract 86406t (1994).

Quon et al., "Formation of β–Amyloid protein deposits in brains of transgenic mice," *Nature*, 352:239–241 (1991).

Raso, V. A., "Immunotherapy of Alzheimer's Disease," *Immunotherapy Weekly*, Abstract (Apr. 2, 1998).

Rogers et al., Complement activation by β–amyloid in Alzheimer Disease, *PNAS*, 89:1–5 (1992).

Rossor et al., "Alzheimer's Disease Families with Amyloid Protein Mutations," *Annals of New York Academy of Sciences*, 695:198–202 (1993).

Selkoe, D.J., "Imaging Alzheimers's Amyloid," *Nat. Biotech.*, 18:823–824 (2000).

Selkoe, Dennis J., "Amyloid Protein and Alzheimer's Disease . . . ," *Scientific American*, pp. 68–78 (11/91).

Selkoe, Dennis J., "In the Beginning . . . ," *Nature*, 354:432–433 (1991).

Selkoe, Dennis J., "The Molecular pathology of Alzheimer's Disease," *Neuron*, 6:487–498 (1991).

Selkoe, Dennis J., "Alheimer's Disease: Genotypes, Phenotype, and Treatments," *Science*, 275:630–631 (1997).

Selkoe, "Alzheimer'Disease: A Central Role for Amyloid", *J. Neuropathol. Exp. Neurol.*, 53(5): 438–447 (1994).

Selkoe, "Physiological production of the β–amyloid protein and the mechanism of Alzheimer's disease", *Trends in Neurosciences*, 16(10): 403–409 (1993).

Seubert et al., "Isolation and quantification of soluble Alzheimer's β–peptide from biological fluids", *Nature*, 359: 325–327 (1992).

Shiosaka, Sadao, "Attempts to make models for Alzheimer's disease," *Neuroscience Res.*, 13:237–255 (1992).
Smits et al., "Prion Protein and Scrapie Susceptibility", *Vet. Quart.*, 19(3): 101–105 (1997).
Solomon et al., "Disaggregation of Alzheimer β–amyloid by site–directed mAb," *PNAS*, 94:4109–4112 (1997).
Solomon et al., "Monoclonal antibodies inhibit in vitro fibrillar aggregation of the Alzheimer β–amyloid peptide," *PNAS*, 93:452–455 (1996).
Stoute et al., A Preliminary Evaluation of a Recombinant Circumsporozoite Protein Vaccine Against *Plasmodium falciparum* Malaria, *N. Engl. J. Med.*, 336(2): 86–91 (1997).
Sturchler–Pierrat et al., "Two amyloid precursor protein transgenic mouse models with Alzheimer disease–like pathology", *PNAS*, 94: 13287–13292 (1997).
Tanaka et al., "NC–1900, an active fragment analog of arginine vasopressin, improves learning and memory deficits induced by beta–amyloid protein in rats," *European J. Pharmacology*, 352:135–142 (1998).
Trieb et al., "Is Alzheimer beta amyloid precursor protein (APP) an autoantigen? Peptides corresponding to parts of the APP sequence stimulate T lymphocytes in normals but not in patients with Alzheimer's disease," *Immunobiology*, 191(2–3):114–115 Abstract C.37, (1994).
Verbeek et al., "Accumulation of Intercellular Adheasion Molecule–1 in Senile Plaques in Brain Tissue of patients with Alzheimer's Disease," *Amer. Journ. Pathology*, 144(1):104–116 (1994).
Walker et al., "Labeling of Cerebral Amyloid In Vivo with a Monoclonal Antibody," *J. Neuropath. Exp. Neurology*, 53(4):377–383 (1994).
Wengenack et al., "Targeting Alzheimer Amyloid plaques in vivo," *Nature Biotech.*, 18:868–824 (2000).
Weiner et al., "Oral Tolerance: Immunologic Mechanisms and Treatment of Animal and Human Organ–Specific Autoimmune Disease by Oral Administration of Autoantigens," *Annu. Rev. Immunol.*, 12:809–837(1994).
Weissmann et al., Bovine spongiform encephalopathy and early onset variant Creutzfeldt–Jakob disease, *Curr. Opin. Neurobiol.*, 7: 695–700 (1997).
Wood et al., Amyloid precursor protein processing and Aβ42 deposition in a transgenic mouse model of Alzheimer disease, *PNAS*, 94: 1550–1555 (1997).
Schenk et al., "Immunization with amyloid–β attenuates Alzheimer–disease–like pathology in the PDAPP mouse," *Nature*, 400: 173–177 (1999).
Van Gool et al., "Concentrations of amyloid–β protein in cerebrospinal fluid increase with age in patients free from neurodegenerative disease," *Neuroscience Letters*, 172:122–124 (1994).
Bercovici et al., "Chronic Intravenous Injections of Antigen Induce and Maintain Tolerance in T Cell Receptor–Transgenic Mice," *Eur. J. Immunol.* 29:345–354 (1999).
Bickel et al., "Site Protected, Cationized Monoclonal Antibody Against Beta Amyloid as a Protential Diagnostic Imaging Technique for Alzheomer's Diseases," *Soc. for Neuroscience Abstracts* 18:764 (1992).
Bard et al., "Peripherally administered antibodies against amyloid β–peptide enter the central nervous system and reduce pathology in a mouse model of Alzheimer disease," *Nature Medicine*, 6(8):916–919 (2000).
Chen et al. "An Antibody to β Amyloid Precursor Protein Inhibits Cell–substratum Adhesion in Many Mammalian Cell Types," *Neuroscience Letters* 125:223–226 (1991).

Demattos et al., "Peripheral Anti Aβ Antibody Alters CNS And Plasma Aβ Clearance and Decreases Brain Aβ Burden in a Mouse Model of Alzheimer's Disease," *Proc. Natl. Acad. Sci. USA, 10.1073/pnas.151261398* (2001).
Friedland et al., "Development of an anti–A monoclonal antibody for in vivo imaging of amyloid anglopathy in Alzheimer's disease," *Mol. Neurology*, 9:107–113 (1994).
Games et al., "Prevention and Reduction of AD–type Pathology in PDAPP Mice Immunized with $A\beta_{1-42}$," *Annals of the New York Academy of Science* 920:274–84 (2000).
Gravina et al., "Amyloid β Protein (Aβ) in Alzheimer's Disease," *J. Biol. Chem.*, 270(13):7013–7016 (1995).
Harrington et al., "Characterisation of an epitope specific to the neuron–specific isoform of human enclase recognised by a monoclonal antibody raised against a synthetic peptide corresponding to the C–terminus of β/A4– protein," *Biochimica Biophysica Acta*, 1158:120–128 (1993).
Helmuth, L., "Further Progress on a β–Amyloid Vaccine," *Science*, 289:375 (2000).
Iwatsubo et al., "Visualization of Aβ42(43) and Aβ40 in Senile Plaques with End–Specific Aβ Monoclonals: Evidence That an Initially Deposited Species Is Aβ42(43)," *Neuron*, 13:45–53 (1994).
Joachim et al., "Antibodies to Non–beta Regions of the Beta–amyloid Precursor Protein Detect a Subset of Senile Plaques," *Am. J. of Pathology* 138:373–378 (1991).
Katzav–Gozansky et al., "Effect of monoclonal antibodies in preventing carboxypeptidase A aggregation," *Biotechnol. Appl. Biochem.*, 23:227–230 (1996).
Konig et al., "Development and Characterization of a Monoclonal Antibody 369.2B Specific for the Carboxyl–Terminus of the βA4 Peptide," *Annals of NY Acad Sci.*, 777:344–355 (1996).
Majocha et al., "Development of a Monoclonal Antibody Specific for β/A4 Amyloid in Alzheimer's Disease Brain for Application to In Vitro Imaging of Amyloid Angiopathy," *The J. of Nuclear Med.* 33:2184–2189 (1992).
Masters et al., "Amyloid Plaque core protein in Alzheimer Disease and Down Syndrome," *Proc. Natl. Acad. Sci. USA*, 82:4245–4249 (1985).
Mori et al., "Mass Spectrometry of Purified Amyloid β Protein Alzheimer's Disease," *J. Biol. Chem.*, 267(24):17082–17088 (1992).
Murphy et al., "Development of a Monoclonal Antibody Specific for the COOH–Terminal of β–Amyloid 1–42 and Its Immunohistochemical Reactivity in Alzheimer's Disease and Related Disorders," *Am. J. Pathology*, 144(55):1082–1088 (1994).
Rudinger, "Characteristics of the Amino Acids as Components of a Peptide Hormone Sequence," in *Peptide Hormones*, J.A. Parson, ed. University Park Press, Baltimore, pp 1–7 (1976).
Saido et al., "Spatial Resolution of Fodrin Proteolysis In Postischemic Brain," *J. Biol. Chem.*, 268(33):25239–25243 (1993).
Saido et al., "Spatial Resolution of the Primary β–Amyloidogenic Process Induced in Postischemic Hippocampus," *J. Biol. Chem.*, 269(21):15253–15257 (1994).
Schenk et al., "Therapeutic Approaches Related to Amyloid–β Peptide and Alzheimer's Disease," *J. Med. Chem.*, 38(21):4141–4154 (1995).
Solomon et al., "Inhibitory effect of monoclonal antibodies on Alzheimer's β–amyloid peptide aggregation," *Int. J. Exp. Clin. Invest.*, 3:130–133 (1996).

Solomon et al., "Thermal Stabilization of Carboxypeptidase A as a Function of PH and Ionic Milleu," *Biochem. Mol. Biol. Int.*, 43(3):601–611 (1997).

Solomon et al., "Modulation of The Catalytic Pathway of Carboxypeptidase A by Conjugation with Polyvinyl Alcohols," *Adv. Mol. Cell Biology*, 15A:33–45 (1996).

Southwick et al., "Assessment of Amyloid β protein in Cerebrospinal fluid as an Aid in the Diagnosis of Alzheimer's Disease," *J. Neurochemistry*, 66:259–268 (1996).

Wen, G.Y., "Alzheimer's Disease and Risk Factors," *J. Food Drug Analysis*, 6(2):465–476(1998).

Wong et al., "Neuritic Plaques and Cerebrovascular Amyloid in Alzheimer Disease are Antigenically Related," *Proc. Natl. Acad. Sci. USA*, 82:8729–8732 (1985).

U.S. patent application Ser. No. 09/724,842, Challfour et al., filed Nov. 28, 2000.

U.S. patent application Ser. No. 09/441,140, Solomon et al., filed Nov. 16, 1999.

Barrow, et al., "Solution Conformations and aggregational Properties of Synthetic Amyloid Beta–Peptides of Alzheimer's Disease. Analysis of Circular Dichroism Spectra" *J. Mol. Biol.*, 225(4): 1075–1093 (1992).

Beasley, "Alzheimer's traced to proteins caused by aging," Reuters Apr. 20, 2001 7:56 PM ET.

Cameron, "Recent Advances in Transgenic Technology," *Molecular Biotechnology*, 7:253–265 (1997).

Caputo et al., "Therapeutic approaches targeted at the amyloid proteins in Alzheimer's disease," *Clin. Neuropharm.*, 15:414A–414B (1992).

Chapman, Paul F., "Model behavior," *Nature*, 408:915–916 (2000).

Chemical Abstract database, Abstract of "Injection of Newborn Mice with Seven Chemical Adjuvants to Help Determine Their–Safety–in Use in Biologicals," Chemical Abstract database, (Publication date unknown).

Chen, et al. A learning deficit related to age and beta–amyloid plaques in a mouse model of Alzheimer's disease, Nature, 408(6815)975–9 (2000).

Chen, et al., "Neurodegenerative Alzheimer–like pathology in PDAPP 717V→F transgenic mice," *Progress in Brain Research*, Van Leeuwen et al. Eds, 117:327–337 (1998).

Chung et al. "Uptake, Degradation, and Release of Fibrillar and Soluble Forms of Alzheimer's Amyloid β–Peptide by Microglial Cells," *J. Biol. Chem.*, 274(45):32301–32308 (1999).

Coloma et al., "Transport Across the Primate Blood Brain Barrier on a Genetically Engineered Chimeric Monoclonal Antibody to the Human Insulin Receptor," *Pharm. Res.*, 17:266–274 (2000).

Conway et al., "Acceleration of oligomerization, not fibrillization, is a shared property of both α–synuclein mutations linked to early–onset Parkinson's disease: Implications for pathogenesis and therapy," *PNAS*, 97(2):571–576 (2000).

Cordell, B., "β–Amyloid formation as a potential therapeutic target for Alzheimer's disease," *Ann. Rev. Pharmacol. Toxicol.*, 34:69–89 (1994).

Costa et al., "Immunoassay for transthyreth variants associated with amyloid neuropathy," *Scand. J. Immunol.*, 38:177–182 (1993).

Daly, et al., "Detection of the membrane–retained carboxy–terminal tail containing polypeptides of the amyloid Precursor protein in tissue from Alzheimer's Disease brain," *Life Sci.*, 63:2121–2131 (1998).

Du, et al., Reduced levels of amyloid beta–peptide antibody in Alzheimer disease, Neurology, 57(5):801–5 (2001).

Dumery et al., "β–Amyloid protein aggregation: its implication in the physiopathology of Alzheimer's disease," *Pathol. Biol.*, 49:72–85 (2001).

Elan, "Elan and AHP Provide an Update on the Phase 2A Clinical Trial of AN–1792," Press Release. (Jan. 28, 2002).

Elan, "Elan and Wyeth Provide Update on Status of Alzheimer's Collaboration," Press Release (Mar. 1, 2002).

Esiri, "Is an effective Immune Intervention of Alzheimer's disease in prospect?," *Trends in Pharm. Sci.*, 22:2–3 (2001).

Felsenstein et al., "Transgenic Rat and In–Vitro Studies of B–Amyloid Precursor Protein Processing;" *Alzheimer's and Parkinson's Diseases*, Hanin et al, Ed., pp 401–409, Plenum Press, New York, (1995).

Frenkel et al., "Generation of auto–antibodies towards Alzheimer's disease vaccination," *Vaccine*, 19:2615–2619 (2001)).

Frenkel et al., "High affinity binding of monoclonal antibodies to the sequential epitope EFRH of β–amyloid peptide is essential for modulation of fibrillar aggregation," *J. of Neurolmmunology*, 95:136–142 (1999).

Frenkel et al., "Immunization against Alzheimer's β–amyloid–plaques via EFRH phage administration," *PNAS USA*, 97:11455–11459 (2000).

Frenkel et al., "N–terminal EFRH sequence of Alzheimer's β–amyloid peptide represents the epitope of its anti–aggregating antibodies," *J. of Neuroimmunology*, 88:85–90 (1998).

Frenkel, et al., "Modulation of Alzheimer's β–amyloid neurotoxicity by site–directed single chain antibody," *J. of Neuroimmunology*, 106:23–31 (2000).

Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York (1997).

Gardella et al., "Intact Alzheimer amyloid precursor protein (APP) is present in platelet membranes and is encoded by platelet mRNA," *Biochem. Biophys. Res. Comm.*, 173:1292–1298 (1990).

Geddes, "N–terminus truncated β–amyloid peptides and C–terminus truncated secreted forms of amyloid precursor protein: distinct roles in the pathogenesis of Alzheimer's disease," *Neurobiology of Aging*, 20:75–79 (1999).

Giulian, et al., "The HHQK Domain of b–Amyloid Provides a Structural Basis for the Immunopathology of Alzheimer's Disease," *Journal of Biological Chem.*, 273:29719–29726 (1998).

Gonzales–Fernandez et al., "Low antigen dose favors selection of somatic mutants with hallmarks of antibody affinity maturation," *Immunology*, 93:149–153 (1998).

Gortner, *Outlines of Biochemistry*, pp. 322–323, John Wiley & Sons, Inc., New York (1949).

Grubeck–Loebenstein, et al., "Immunization with β–amyloid: could T–cell activation have a harmful effect?", *TINS*, 23:114 (2000).

Haass et al. "Amyloid beta–peptide is produced by cultured cells during normal metabolism," *Nature*, 359(8393):322–5 (1992).

Harigaya, et al., "Modified amyloid β protein ending at 42 or 40 with different solubility accumulates in the brain of Alzheimer's disease," *Biochem. Biophys. Res. Comm.*, 211:1015–1022 (1995).

Hazama, et al., "Intranasal Immunization Against Herpes Simplex Virus Infection by Using a Recombinant Glycoprotein D Fused With Immunomodulating Proteins, the B Subunit of *Escherichia coli* Heat–Labile Enterotoxin and Interleukin–2", *Immunology*, vol. 78: 643–649 (1993).

Hilbich et al., :Human and rodent sequence analogs of Alzheimer's amyloid βA4 share similar properties and can be solubilized in buffers of pH 7,4, *Eur. J. Biochem.*, 201:61–69 (1991).

Ikeda, et al., "Immunogold labeling of cerebrovascular and neuritic plaque amyloid fibrils in Alzheimer's disease with an anti–β protein monclonal antibody," *Lab. Invest.*, 57:446–449 (1987).

Janus, et al. A beta peptide immunization reduces behavioural impairment and plaques in a model of Alzheimer's disease, Nature, 408(6815):979–82 (2000).

Jen, et al., "Preparation and purification of antisera against different regions or isoforms of b–amyloid precursor protein," *Brain Research Protocols*, 2:23–30 (1997).

Jobling and Holmes, "Analysis of structure and function of the B subunit of cholera toxin by the use of site–directed-:mutagenesis," *Molecular Microbiology*, 5(7):1755–1767 (1991).

Kida, et al., "Early amyloid–β deposits show different immunoreactivity to the amino– and carboxy–terminal regions of b–peptide in Alzheimer's disease and Down's syndrome brain," *Neuroscience Letters*, 193:105–108 (1995).

Lansbury, Peter T., "Inhibition of amyloid formation: a strategy to delay the onset of Alzheimer's disease," *Curr. Ops. in Chemical Biology*, 1:260–267 (1997).

Lemere, et al., "Nasal Aβ treatment induces anti–Aβ antibody production and decreases cerebral amyloid burden in PD–APP mice," *Annals of the NY Acad. Sci.*, 920:328–331 (2000).

Mak, et al., "Polyclonals to b–amyloid (1–42) identify most plaque and vascular deposits in Alzheimer cortex, but not striatum," *Brain Research*, 667:138–142 (1994).

Mann, et al., "Amyloid β protein (Aβ) deposition in chromosome 14–linked Alzheimer's disease: Predominance of A$\beta_{42(43)}$," *Annals of Neurology*, 40:149–156 (1996).

Mann, et al., "The extent of amyloid deposition in brain in patients with Down's syndrome does not depend upon the apolipoprotein E genotype," *Neuroscience Letters*, 196:105–108 (1995).

Masliah et al., "β–Amyloid peptides enhance α–synuclein accumulation and neuronal deficits in a transgenic mouse model linking Alzheimer's disease and Parkinson's disease," *PNAS*, 98(21):12245–12250 (2001).

Mattson, Cellular actions of beta–amyloid precursor protein and its soluble and fibrillogenic derivatives, Physiol Rev, 77(4):1081–132 (1997).

McGeer, et al., "Immunohistochemical localization of beta–amyloid precursor protein sequences in Alzheimer and normal brain tissue by light and electon microscopy," *J. of Neuroscience Res.*, 31:428–442 (1992).

McNeal et al., "Stimulation of local immunity and protection in mice by intramuscular immunization with triple– or double–layered rotavirus particles and QA–21," *Virology*, 243:158–166 (1998).

Mena, et al., "Monitoring pathological assembly of tau and β–amyloid proteins in Alzheimer's disease," *Acta Neuropathol.*, 89:50–56 (1995).

Merluzzi, et al. Humanized antibodies as potential drugs for therapeutic use. Adv Clin Path. 4(2):77–85 (2000).

Morgan, et al, A beta peptide vaccination prevents memory loss in an animal model of Alzheimer's disease, Nature, 408(6815):982–5 (2000).

Morris,–et al., "The Consortium to Establish a registry for Alzheimer's Disease (CERAD)," *Neurology*, 39:1159–65 (1989).

Nakamura et al., "Histopathological studies on senile plaques and cerebral amyloid angiopathy in aged cynomologus monkeys," *Exp. Anim.*, 43:711–718 (1995).

Nakamura, et al., "Carboxyl end–specific monoclonal antibodies to amyloid β protein (Aβ) subtypes (Aβ40 abnd Aβ42(43) differentiate Ab in senile plaques and amyloid angiopathy in brains of aged cynomolgus monkeys," *Neuroscience Letters*, 201:151–154 (1995).

Nakayama et al., "Histopahtological studies of senile plaques and cerebral amyloidosis in cynomolgus monkeys," *J. of Med. Primatology*, 27:244–252 (1998).

Newcombe and Cohen, "Solubility characteristics of isolated amyloid fibrils," *Biochim. Biophys. Acta*, 104:480–486 (1965).

Niemann, "Transgenic farm animals get off the ground," *Transgenic Research* 7:73–75 (1998).

Pardridge et al., "Chimeric peptides as a vehice for peptide pharmaceutical delivery through the blood–brain barrier," *Biochem. Biophys. Res. Comm.*, 146:307–313 (1987).

Perutz et al., "Amyloid fibers are water–filed nanotubes," *PNAS*, 99(8):5591–5595 (2002).

Peterson, et al., "Recombinant Antibodies: Alternative Strategies for Developing and Manipulating Murine–Derived Monoclonal Antibodies," *Laboratory Animal Science*, 46(1):8–14 (1996).

Philippe, et al., "Generation of a monoclonal antibody to the carboxy–terminal domain of tau by immunization with the amino–terminal domain of the amyloid precursor protein," *J. of Neuroscience Res.*, 46:709–719 (1996).

Saito et al., "Vector–mediated delivery of $^{125}$I–labeled β–amyloid peptide Ab$^{1-40}$ through the blood–brain barrier and binding to Alzheimer disease amyloid of the Aβ$^{1-40}$ vector complex," *PNAS USA*, 92:10227–10231 (1995).

Saitoh, N. and K; Imai, "Immunological analysis of Alzheimer's disease using anti– β–protein monoclonal antibodies," *Sapporo Med. J.*, 60:309–320 (1991).

Sasaki et al., "Human choroid plexus is an uniquely Involved area of the brain in amyloidosis: a histochemical, immunohistochemical and ultrastructural study," *Brain Res.*, 755:193–201 (1997).

Schenk, et al, Immunotherapy with beta–amyloid for Alzheimer's disease: a new frontier. DNA Cell Biol. 20(11):679–81 (2001).

Schenk, et al., "β–peptide immunization," *Arch. Nuerol.*, 57:934–936 (2000).

Selkoe, The cell biology of beta–amyloid precursor protein and presenllin in Alzheimer's disease. Trends Cell Biol. 8(11):447–53 (1998).

Sigmund, "Viewpoint: Are Studies in Genetically Altered Mice Out of Control," *Arterloscler Thromb Vasc Biol.*, 20:1425–1429 (2000).

Sigurdsson, et al. In vivo reversal of amyloid–beta lesions in rat brain. J Neuropathol Exp Neurol. 59(1):11–17 (2000).

Sinha, et al. Recent advances in the understanding of the processing of APP to beta amyloid peptide. Ann N Y Acad Sci. 920:206–8 (2000).

Skolnick and Fetrow, "From genes to protein structure and function: novel applications of computational approaches in the genomic era," *Trends in Biotech*, 18(1):34–39 (2000).

Small, et al. Alzheimer's disease and Abeta toxicity: from top to bottom. Nat Rev Neurosci. 2(8):595–8 (2001).

Soto, et al, Beta sheet breaker peptides inhibit fibrillogenesis in a rat brain model of amyloidosis: Implications for Alzheimer's therapy. Nat Med. 4(7):822–6 (1998).

St. George–Hyslop, Peter H. and David A. Westaway, :Antibody clears senile plaques, *Nature*, 40:116–117 (1999).

Stein and Johnson, "Lack of Neurodegeneration in Transgenic Mice Overexpressing Mutant Amyloid Precursor Protein is Associated with increased Levels of Transthyretin and Activation of Cell Survival Pathways," *The Journal of Neuroscience*, 22(17):7380–7388 (Sep. 1, 2002).

Szendrei, et al., "The effects of aspartic acid–bond Isomerization on In vitro properties of the amyloid β–peptide as modeled with N–terminal decapeptide fragments," *Int. J. Peptide Protein Res.*, 47:289–296 (1996).

Tennent et al., "Serum amyloid P component prevents proteolysis of the amyloid fibrils of Alzheimer's disease and systemic amyloidosis," *PNAS*, 92:4299–4303 (1995).

Thorsett, E.D. and L.H. Latimer, "Therapeutic approaches to Alzheimer's disease," *Curr. Op. in Chem. Biology*, 4:377–382 (2000).

Tjernberg et al., "Arrest of β–amyloid fibril formation by a pentapeptide ligand," *Journal of Biological Chemistry*, 271:8545–8548 (1996).

Vehmas, et al. beta–Amyloid peptide vaccination results in marked changes in serum and brain Abeta levels in APPswe/PS1 Delta EO–mice, as detected by SELDI–TOF–based ProteinChip® technology, DNA Cell Biol. (11):713 21 (2001).

Weiner et al., "Nasal administration of amyloid–β peptide decreases cerebral amyloid burden in a mouse model of Alzheimer's disease," *Annals of Neurology*, 48:567–579 (2000).

Wu, et al., "Drug targeting of a peptide radiopharmaceutical through the primate blood–brain barrier in vivo with a monoclonal antibody to the human insulin receptor," *J. Clin. Invest.*, 100:1804–1812 (1997).

Yamaguchi et al., Diffuse plaques associated with astroglial amyloid β protein, possibly showing a disappearing stage of senile plaques, *Acta Neuropathol.* 95:217–222 (1998).

Younkin, "Amyloid β vaccination: reduced plaques and improved cognition," *Nature Medicine*, 7:18–19 (2001).

Check, "Battle of the Mind," *Nature*, 422:370–372 (Mar. 2003).

Nicoll et al., "Neuropathology of human Alzheimer's disease after immunization with amyloidβ peptide: a case report," *Nature Medicine*, 9(4):448–452 (Apr. 2003).

Aguzzi et al., "Prion research: the next frontiers," *Nature*, 389:795–798 (1997).

Akiyama et al., "Inflammation and Alzheimer's disease," *Neurobiology of Aging*, 21:383–421 (2000).

Akiyama et al., "Occurrence of the Diffuse Amyloid β–Protein (Aβ)Deposits With Numerous Aβ–Containing Gilal Cells in the Cerebral Cortex of Patients With Alzheimer's Disease," *Glia*, 25:324–331 (1999).

Check, "Battle of the Mind," *Nature*, 422:370–372 (Mar. 2003).

Diomede et al., "Activation effects of a prion protein fragment [PrP–(106–126)] on human leucocytes," *Biochem. J.*, 320:53–570 (1996).

Dodart, "Immunotherapy for Alzheimer's disease: will vaccination work?" *Trends in Molecular Medicine*, 9(3):85–87 (2003).

Fratutschy et al., "Effects of Injected Alzheimer β–amyloid cores in rat brain," *PNAS*, 88:8362–8366 (1991).

Furlan et al., "Vaccination with amyloid–β peptide induces autoimmune encephalomyelitis in C57/BL6 mice," *Brain*, 126:285–291 (2003).

Goldfarb et al., "The Transmissible Spongiform Encephalopathies," *Ann. Rev. Med.*, 46:57–65 (1995).

Goldsteins et al., "Goldsteins et al., Exposure of cryptic epitopes on transthyretin only in amypoid and in amyloidogenic mutants," *PNAS*, 96:3108–3113 (1999).

Jakes et al., "Characterisation of an Antibody Relevant to the Neuropathology of Alzheimer Disease," *Alzheimer Disease and Associated Disorders*, 9(1):47–51, Raven Press, Ltd., New York (1995).

Johnstone et al., Nuclear and Cytoplasmic Localization of the β–Amyloid Peptide (1–43) in Transfected 293 Cells, *Biochemical and Biophysical Research Communications*, 220:710–718 (1996).

Jorbeck et al., "Artificial Salmonella Vaccines: *Salmonella typhimurium* O–antigen–Specific Oligosaccharide–Protein Conjugates Elicit Opsonizing Antibodies that Enhance Phagocytosis," *Infection and Immunity*, May:497–502 (1981).

Kovács et al., "Mutations of the Prion Protein Gene Phenotypic Spectrum," *J. Neurol.*, 249:1567–1582 (2002).

Monsonego et al., "Immune hyporesponsiveness to amyloid β–peptide in amyloid precursor protein transgenic mice: Implications for the pathogenesis and treatment of Alzheimer's disease," *PNAS*, 98(18):10273–10278 (2001).

Munch et al., "Potentional neurotoxic inflammatory response to Aβ vaccination in humans," (2002) *J. Neural Transm.*, 109:1081–1087.

Munson ed., "Principals of Pharmacology: Basic Concepts & Clinical Applications," (1995), 47–48, Chapman & Hall, New York, New York.

Mutschler et al., "Drug Actions: Basic Principles and Therapeutic Aspects," (1995) 7, 11–12, *medpharm* Scientific Publishers, Stuttgart, Germany.

Nicoll et al., "Neuropathology of human Alzheimer's disease after immunization with amyloid–β peptide: a case report," *Nature Medicine*, 9(4):448–452 (Apr. 2003).

Palha et al., "Antibody recognition of amyloidogenic transthyretin variants in serum of patients with familial amyloidiotic polyneuropathy," *J. Mol. Med.*, 7:703–707 (2001).

Prusiner et al., "Ablation of the prion protein (PrP) gene in mice prevents scraple and facilitates production of anti–PrP antibodies," *PNAS*, 90:10608–10612 (1993).

Sigurdsson et al., "Anti–priori antibodies for prophylaxis following prion exposure in mice," *Neurosciences Letters*, 336:185–187 (2003).

Sigurdsson et al., "Immunization Delays the Onset of Prion Disease in Mice," *American Journal of Pathology*, 161:13–17 (2002).

Sigurdsson et al., "A safer vaccine for Alzheimer's disease?," *Neurobiology of Aging*, 23:1001–1008 (2002).

Sipe, "Amyloidosis," *Annu. Rev. Biochem.*, 61:947–975 (1992).

Spooner et al., "The generation and characterization of potentially therapeutic Aβ antibodies in mice: differences according to strain and immunization protocol," *Vaccine*, 21:290–297 (2002).

Su et al., "Intravascular infusions of soluble β–amyloid compromise the blood–brain barrier, activate CNS Glial cells and Induce peripheral hemorrhage," *Brain Research*, 818:105–107 (1999).

Tal et al., "Complete Freund's Adjuvant Immunization Prolongs Survival in Experimental Prion Disease in Mice," *Journal of Neuroscience Research*, 71:286–290 (2003).

Tan et al., "Amyloidosis," *Histopathology*, 25:403–414 (1994).

Tsuzuki et al., "Amyloid β protein in rat soleus in choroquine–induced myopthy using end–specific antibodies for Aβ40 and Aβ42: immunohistochemical evidence for amyloid β protein," *Neuroscience Letters*, 2002:77–80 (1995).

Weldon et al., "Neurotoxicity of Aβ Peptide: Confocal Imaging of Cellular Changes Induced by—Amyloid in Rat CNS in Vivo," *Society for Neuroscicence Abstracts*, 22(Part 1) (1996).

Wisniewski et al., "Therapeutics in Alzheimer's and Prion Diseases," *Biochemical Society Transactions*, 30(4):–574–587 (2002).

Benjamini and Leskowitz, from *IMMUNOLOGY A Short Course*, Second Edition, Chapter 4, Antibody Structure, pp. 49–65, 1991, published by Wiley–Liss, Inc., New York, New York.

Pan et al., "Antibodies to β–Amyloid Decrease the Blood-to–Brain Transfer of β–Amyloid Peptide," *Exp. Biol. Med.*, 227(8):609–615 (2002).

STUDY 002
RETROSPLENIAL CORTICAL ASTROCYTOSIS

CORTEX

| PBS CONTROL | | UNTREATED CONTROL | |
|---|---|---|---|
| 624-165 | 272 | 764-181 | 3470 |
| 625-166 | 1802 | 785-182 | 171 |
| 626-167 | 62 | 766-183 | 91 |
| 633-168 | 4696 | 767-184 | 6692 |
| 634-169 | 3090 | 768-185 | 1353 |
| 671-170 | 2417 | 771-186 | 1153 |
| 672-171 | 2840 | 772-187 | 3800 |
| 829-172 | 3320 | 780-188 | 3740 |
| 830-173 | 1833 | 843-189 | 163 |
| 831-174 | 416 | 844-190 | 122 |
| 792-175 | 126 | 845-191 | 427 |
| 793-176 | 2559 | 846-192 | 2674 |
| 794-177 | 289 | 887-193 | 453 |
| 732-178 | 179 | 888-194 | 2996 |
| 733-179 | 1329 | 889-195 | 1075 |
| 734-180 | 5665 | | |
| MEDIAN<br>p VALUE (M-W) | 1817 | MEDIAN<br>p VALUE (M-W) | 1153 |
| MEAN<br>ST. DEV.<br>% CV<br>p VALUE (t TEST) | 1931<br>1718<br>89<br><br>n=16 | MEAN<br>ST. DEV.<br>% CV<br>p VALUE (t TEST) | 1825<br>1769<br>97<br><br>n=15 |

FIG. 15A

CORTEX

| 2 mg ALUM 100 µg AN1528 | | 50 µg ALUM 100 µg AN1528 | |
|---|---|---|---|
| 660-083 | 295 | 643-105 | 385 |
| 661-084 | 3180 | 644-106 | 2640 |
| 662-085 | 2480 | 645-107 | 2403 |
| 633-086 | 3014 | 654-108 | 1741 |
| 664-087 | 5870 | 655-109 | 3053 |
| 665-088 | 5978 | 656-110 | 5990 |
| 693-089 | 1620 | 678-111 | 3360 |
| 694-090 | 35 | 679-112 | 1230 |
| 695-091 | 3400 | 704-114 | 2680 |
| 697-092 | 2630 | 705-115 | 78 |
| 698-093 | 983 | 706-116 | 1290 |
| 699-094 | 5327 | 729-117 | 3180 |
| 701-095 | 1862 | 730-118 | 1833 |
| 702-096 | 1849 | 731-119 | 4590 |
| 703-097 | 2239 | 736-120 | 1112 |
| 739-098 | 806 | 737-121 | 1653 |
| 740-099 | 5303 | 757-122 | 992 |
| 741-100 | 459 | 758-123 | 4692 |
| 800-103 | 154 | 808-124 | 785 |
| 801-104 | 852 | 809-125 | 244 |
|  |  | 810-126 | 32 |
| MEDIAN p VALUE (M-W) | 2051 | MEDIAN p VALUE (M-W) | 1741 |
| MEAN ST. DEV. % CV p VALUE (t TEST) | 2407 1913 79 n=20 | MEAN ST. DEV. % CV p VALUE (t TEST) | 2140 1659 78 n=21 |

FIG. 15B

CORTEX

| 25 µg QS21<br>100 µg AN1528 | | CFA/IFA<br>100 µg AN1792 | |
|---|---|---|---|
| 615-128 | 1257 | 539-068 | 693 |
| 616-129 | 361 | 640-069 | 508 |
| 617-130 | 1008 | 641-070 | 440 |
| 536-131 | 3290 | 642-071 | 467 |
| 637-132 | 2520 | 690-072 | 42 |
| 638-133 | 3880 | 691-073 | 2491 |
| 744-134 | 627 | 692-074 | 121 |
| 745-135 | 58 | 795-075 | 137 |
| 746-136 | 2610 | 796-076 | 822 |
| 747-137 | 1509 | 797-077 | 475 |
| 769-138 | 1788 | 748-087 | 600 |
| 770-139 | 988 | 749-079 | 78 |
| 773-140 | 1199 | 750-080 | 1267 |
| 774-141 | 339 | 751-081 | 1351 |
| 775-142 | 402 | 761-082 | 69 |
| 776-143 | 537 | | |
| 840-144 | 1119 | | |
| 841-145 | 194 | | |
| 821-146 | 1259 | | |
| 822-147 | 5413 | | |
| 823-148 | 2233 | | |
| MEDIAN<br>p VALUE (M-W) | 1199 | MEDIAN<br>p VALUE (M-W) | 475<br>0.0481 |
| MEAN<br>ST. DEV.<br>% CV<br>p VALUE (t TEST) | 1552<br>1364<br>88<br><br>n=21 | MEAN<br>ST. DEV.<br>% CV<br>p VALUE (t TEST) | 637<br>655<br>103<br>0.0106<br>n=15 |

FIG. 15C

CORTEX

| 5 μg THIMEROSAL/PBS 10 μg AN1792 | | 2 mg ALUM 100 μg AN1792 | |
|---|---|---|---|
| 635-149 | 1337 | 610-001 | 432 |
| 669-150 | 4644 | 611-002 | 1012 |
| 670-151 | 6335 | 612-003 | 3607 |
| 673-152 | 3700 | 613-004 | 508 |
| 674-153 | 2750 | 620-005 | 465 |
| 676-154 | 1687 | 621-006 | 16 |
| 681-156 | 185 | 622-007 | 28 |
| 682-157 | 8031 | 623-008 | 217 |
| 683-158 | 3450 | 708-009 | 2738 |
| 754-159 | 157 | 709-010 | 927 |
| 755-160 | 6857 | 710-011 | 1609 |
| 756-161 | 482 | 716-012 | 1608 |
| 805-162 | 524 | 784-014 | 3890 |
| 806-163 | 397 | 785-015 | 1614 |
| 807-164 | 234 | 786-016 | 285 |
| | | 787-017 | 3102 |
| | | 788-018 | 1617 |
| | | 789-019 | 1474 |
| | | 815-020 | 424 |
| | | 816-021 | 1375 |
| | | 817-022 | 2323 |
| MEDIAN | 1687 | MEDIAN | 1375 |
| p VALUE (M-W) | | p VALUE (M-W) | 0.5000 |
| MEAN | 2718 | MEAN | 1394 |
| ST. DEV. | 2685 | ST. DEV. | 1166 |
| % CV | 99 | % CV | 84 |
| p VALUE (t TEST) | | p VALUE (t TEST) | 0.2650 |
| | n=15 | | n=21 |

FIG. 15D

CORTEX

| 50 μg MPL<br>100 μg AN1792 | | 25 μg QS21<br>100 μg AN1792 | |
|---|---|---|---|
| 646-023 | 2002 | 627-045 | 91 |
| 647-024 | 147 | 628-046 | 3397 |
| 648-025 | 1304 | 631-049 | 3702 |
| 649-026 | 34 | 632-050 | 1776 |
| 650-027 | 980 | 667-052 | 1832 |
| 724-028 | 1282 | 668-053 | 3023 |
| 726-030 | 1966 | 686-054 | 189 |
| 727-031 | 733 | 687-055 | 891 |
| 720-032 | 2563 | 688-056 | 240 |
| 721-033 | 5563 | 689-057 | 110 |
| 802-034 | 113 | 712-059 | 3311 |
| 803-035 | 671 | 825-061 | 1009 |
| 804-036 | 51 | 826-082 | 18165 |
| 811-037 | 613 | 827-063 | 73 |
| 812-038 | 332 | 828-064 | 78 |
| 813-039 | 1454 | 837-065 | 1051 |
| 814-040 | 2441 | 838-066 | 270 |
| 833-014 | 742 | 839-067 | 371 |
| 834-042 | 40 | | |
| 836-044 | 807 | | |
| MEDIAN | 774 | MEDIAN | 950 |
| p VALUE (M-W) | 0.1710 | p VALUE (M-W) | 0.4076 |
| MEAN | 1192 | MEAN | 2199 |
| ST. DEV. | 1299 | ST. DEV. | 4187 |
| % CV | 109 | % CV | 190 |
| p VALUE (t TEST) | 0.1506 | p VALUE (t TEST) | 0.8131 |
| | n=21 | | n=18 |

PASSIVE IMMUNIZATION TREATMENT OF ALZHEIMER'S DISEASE

TECHNICAL FIELD

The invention resides in the technical fields of immunology and medicine.

BACKGROUND OF THE INVENTION

Alzheimer's disease (AD) is a progressive disease resulting in senile dementia. See generally Selkoe, TINS 16, 403–409 (1993); Hardy et al., WO 92/13069; Selkoe, J. Neuropathol. Exp. Neurol. 53, 438–447 (1994); Duff et al., Nature 373, 476–477 (1995); Games et al., Nature 373, 523 (1995). Broadly speaking, the disease falls into two categories: late onset, which occurs in old age (65+years) and early onset, which develops well before the senile period, i.e., between 35 and 60 years. In both types of disease, the pathology is the sarre but the abnormalities tend to be more severe and widespread in cases beginning at an earlier age. The disease is characterized by at least two types of lesions in the brain, senile plaques and neurofibrillary tangles. Senile plaques are areas of disorganized neuropil up to 150 μm across with extracellular amyloid deposits at the center visible by microscopic analysis of sections of brain tissue. Neurofibrillary tangles are intracellular deposits of microtubule associated tau protein consisting of two filaments twisted about each other in pairs.

The principal constituent of the plaques is a peptide termed Aβ or β-amyloid peptide. Aβ peptide is an internal fragment of 39–43 amino acids of a precursor protein termed amyloid precursor protein (APP). Several mutations within the APP protein have been correlated with the presence of Alzheimer's disease. See, e.g., Goate et al., Nature 349, 704) (1991) (valine$^{717}$ to isoleucine); Chartier Harlan et al. Nature 353, 844 (1991)) (valine$^{717}$ to glycine); Murrell et al., Science 254, 97 (1991) (valine$^{717}$ to phenylalanine); Mullan et al., Nature Genet. 1, 345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ1–42 and Aβ1–43). Mutations in other genes, such as the presenilin genes, PS1 and PS2, are thought indirectly to affect processing of APP to generate increased amounts of long form Aβ (see Hardy, TINS 20, 154 (1997)). These observations indicate that Aβ, and particularly its long form, is a causative element in Alzheimer's disease.

McMichael, EP 526,511, proposes administration of homeopathic dosages (less than or equal to $10^{-2}$ mg/day) of Aβ to patients with preestablished AD. In a typical human with about 5 liters of plasma, even the upper limit of this dosage would be expected to generate a concentration of no more than 2 pg/ml. The normal concentration of Aβ in human plasma is typically in the range of 50–200 pg/ml (Seubert et al., Nature 359, 325–327 (1992)). Because EP 526,511's proposed dosage would barely alter the level of endogenous circulating Aβ and because EP 526,511 does not recommend use of an adjuvant, as an immunostimulant, it seems implausible that any therapeutic benefit would result.

By contrast, the present invention is directed inter alia to treatment of Alzheimer's and other anyloidogenic diseases by administration of fragments of Aβ, or antibody to certain epitopes within Aβ to a patient under conditions that generate a beneficial immune response in the patient. The invention thus fulfills a longstanding need for therapeutic regimes for preventing or ameliorating the neuropathology and, in some patients, the cognitive impairment associated with Alzheimer's disease.

This application is related to International Application No. PCT/US00/14810 filed May 26, 2000, Publication No. WO 00/72880; U.S. application Ser. No. 322,289, filed May 28 1999; PCT/US98/25386, filed Nov. 30, 1998, Publication No. WO 99/27944; U.S. application Ser. No. 09/201,430, filed Nov. 30, 1998; U.S. Application No. 60/067,740, filed Dec. 2, 1997; and, U.S. Application No., filed Apr. 7, 1998; each of which is incorporated by reference in its entirety for all purposes.

SUMMARY OF THE CLAIMED INVENTION

In one aspect, the invention provides methods of preventing or treating a disease associated with amyloid deposits of Aβ in the brain of a patient. Such diseases include Alzheimer's disease, Down's syndrome and cognitive impairment. The latter can occur with or without other characteristics of an amyloidogenic disease. Some methods of the invention entail administering an effective dosage of an antibody that specifically binds to a component of an amyloid deposit to the patient. Such methods are particularly useful for preventing or treating Alzheimer's disease in human patients. Some methods entail administering an effective dosage of an antibody that binds to Aβ. Some methods entail administering an effective dosage of an antibody that specifically binds to an epitope within residues 1–10 of Aβ. In some methods, the antibody specifically binds to an epitope within residues 1–6 of Aβ. In some methods, the antibody specifically binds to an epitope within residues 1–5 of Aβ. In some methods, the antibody specifically binds to an epitope within residues 1–7 of Aβ. In some methods, the antibody specifically binds to an epitope within residues 3–7 of Aβ. In some methods, the antibody specifically binds to an epitope within residues 1–3 of Aβ. In some methods, the antibody specifically binds to an epitope within residues 1–4 of Aβ. In some methods, the antibody binds to an epitope comprising a free N-terminal residue of Aβ. In some methods, the antibody binds to an epitope within residues of 1–10 of Aβ wherein residue 1 and/or residue 7 of Aβ is aspartic acid. In some methods, the antibody specifically binds to Aβ peptide without binding to full-length amyloid precursor protein (APP). In some methods, the isotype of the antibody is human IgG1.

In some methods, the antibody binds to an amyloid deposit in the patient and induces a clearing response against the amyloid deposit. For example, such a clearing response can be effected by Fc receptor mediated phagocytosis.

The methods can be used on both asymptomatic patients and those currently showing symptoms of disease. The antibody used in such methods can be a human, humanized, chimeric or nonhuman antibody and can be monoclonal or polyclonal. In some methods, the antibody is prepared from a human immunized with Aβ peptide, which human can be the patient to be treated with antibody.

In some methods, the antibody is administered with a pharmaceutical carrier as a pharmaceutical composition. In some methods, antibody is administered at a dosage of 0.0001 to 100 mg/kg, preferably, at least 1 mg/kg body weight antibody. In some methods, the antibody is administered in multiple dosages over a prolonged period, for example, of at least six months. In some methods, the antibody is administered as a sustained release composition. The antibody can be administered, for example, intraperitoneally, orally, subcutaneously, intracranially, intramuscularly, topically, intranasally or intravenously.

In some methods, the antibody is administered by administering a polynucleotide encoding at least one antibody chain to the patient. The polynucleotide is expressed to produce the antibody chain in the patient. Optionally, the polynucleotide encodes heavy and light chains of the antibody. The polynucleotide is expressed to produce the heavy and light chains in the patient. In some methods, the patient is monitored for level of administered antibody in the blood of the patient.

In another aspect, the invention provides methods of preventing or treating a disease associated with amyloid deposits of Aβ in the brain of patient. For example, the methods can be used to treat Alzheimer's disease or Down's syndrome or cognitive impairment. Such methods entail administering fragments of Aβ or analogs thereof eliciting an immunogenic response against certain epitopes within Aβ. Some methods entail administering to a patient an effective dosage of a polypeptide comprising an N-terminal segment of at least residues 1–5 of Aβ, the first residue of Aβ being the N-terminal residue of the polypeptide, wherein the polypeptide is free of a C-terminal segment of Aβ. Some methods entail administering to a patient an effective dosage of a polypeptide comprising an N-terminal segment of Aβ, the segment beginning at residue 1–3 of Aβ and ending at residues 7–11 of Aβ. Some methods entail administering to a patient an effective dosage of an agent that induces an immunogenic response against an N-terminal segment of Aβ, the segment beginning at residue 1–3 of Aβ and ending at residues 7–11 of Aβ without inducing an immunogenic response against an epitope within residues 12–43 of Aβ43.

In some of the above methods, the N-terminal segment of Aβ is linked at its C-terminus to a heterologous polypeptide. In some of the above methods, the N-terminal segment of Aβ is linked at its N-terminus to a heterologous polypeptide. In some of the above methods, the N-terminal segment of Aβ is linked at its N and C termini to first and second heterologous polypeptides. In some of the above methods, the N-terminal segment of Aβ is linked at its N terminus to a heterologous polypeptide, and at its C-terminus to at least one additional copy of the N-terminal segment. In some of the above methods, the heterologous polypeptide and thereby a B-cell response against the N-terminal segment. In some of the above methods, the polypeptide further comprises at least one additional copy of the N-terminal segment. In some of the above methods, the polypeptide comprises from N-terminus to C-terminus, the N-terminal segment of Aβ, a plurality of additional copies of the N-terminal segment, and the heterologous amino acid segment. In some of the above methods, the N-terminal segment consists of Aβ1–7. In some of the above methods, the N-terminal segment consists of Aβ3–7.

In some methods, the fragment is free of at least the 5 C-terminal amino acids in Aβ43. In some methods, the fragment comprises up to 10 contiguous amino acids from Aβ. Fragments are typically administered at greater than 10 micrograms per dose per patient.

In some methods, the fragment is administered with an adjuvant that enhances the immune response to the Aβ peptide. The adjuvant and fragment can be administered in either order or together as a composition. The adjuvant can be, for example, aluminum hydroxide, aluminum phosphate, MPL™, QS-21 (Stimulon™) or incomplete Freund's adjuvant.

The invention further provides pharmaceutical compositions comprising fragments of Aβ or other agents eliciting immunogenic response to the same epitopes of Aβ, such as described above, and an adjuvant. The invention also provides pharmaceutical compositions comprising any of the antibodies described above and a pharmaceutically acceptable carrier.

In another aspect, the invention provides methods of screening an antibody for activity in treating a disease associated with deposits of Aβ in the brain of a patient (e.g., Alzheimer's disease). Such methods entail contacting the antibody with a polypeptide comprising at least five contiguous amino acids of an N-terminal segment of Aβ beginning at a residue between 1 and 3 of Aβ, the polypeptide being free of a C-terminal segment of Aβ. One then determines whether the antibody specifically binds to the polypeptide, specific binding providing an indication that the antibody has activity in treating the disease.

In another aspect, the invention provides methods of screening an antibody for activity in clearing an antigen-associated biological entity. Such methods entail combining the antigen-associated biological entity and the antibody and phagocytic cells bearing Fc receptors in a medium. The amount of the antigen-associated biological entity remaining in the medium is then monitored. A reduction in the amount of the antigen-associated biological entity indicates the antibody has clearing activity against the antigen-associated biological entity. The antigen can be provided as a tissue sample or in isolated form. For example, the antigen can be provided as a tissue sample from the brain of an Alzheimer's disease patient or a mammal animal having Alzheimer's pathology. Other tissue samples against which antibodies can be tested for clearing activity include cancerous tissue samples, virally infected tissue samples, tissue samples comprising inflammatory cells, nonmalignant abnormal cell growths, or tissue samples comprising an abnormal extracellular matrix.

In another aspect, the invention provides methods of detecting an amyloid deposit in a patient. Such methods entail administering to the patient an antibody that specifically binds to an epitope within amino acids 1–10 of Aβ, and detecting presence of the antibody in the brain of the patient. In some methods, the antibody binds to an epitope within residues 4–10 of Aβ. In some methods, the antibody is labelled with a paramagnetic label and detected by nuclear magnetic resonance tomography.

The invention further provides diagnostic kits suitable for use in the above methods. Such a kit comprises an antibody that specifically binds to an epitope with residues 1–10 of Aβ. Some kits bear a label describing use of the antibody for in vivo diagnosis or monitoring of Alzheimer's disease.

BRIEF DESCRIPTION OF THE DRAWINGS

FIGS. 15 A—E: Aβ levels in the cortex of 12-month old PDAPP mice treated with AN1792 or AN1528 in combination with different adjuvants. The Aβ level for individual mice in each treatment group, and the median, mean, and p values for each treatment group are shown.

FIG. 15A: The values for mice in the PBS-treated control group and the untreated control group.

FIG. 15B: The values for mice in the AN1528/alum and AN1528/MPL-treatment groups.

FIG. 15C: The values for mice in the AN1528/QS21 and AN1792/Freund's adjuvant treatment groups.

FIG. 15D: The values for mice in the AN1792/Thimerosol and AN1792/alum treatment groups.

FIG. 15E: The values for mice in the AN1792/MPL and AN1792/QS21 treatment groups.

DEFINITIONS

Figure 1:
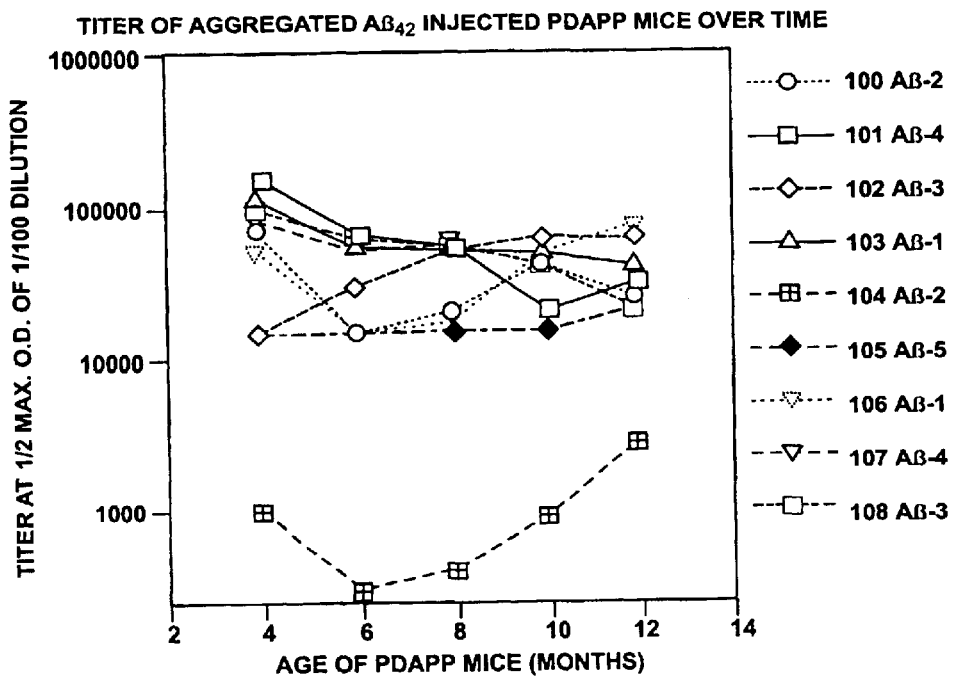
FIG. 1: Antibody titer after injection of transgenic mice with Aβ1–42.

The term "substantial identity" means that two peptide sequences, when optimally aligned, such as by the programs GAβ or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of algorithm that is suitable for determining percent sequence identity and sequence similarity is the BLAST algorithm, which is described in Altschul et al., *J. Mol. Biol.* 215:403410 (1990). Software for performing BLAST analyses is publicly available through the National Center for Biotechnology Information (http://www.ncbi.nlm.nih.gov/). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff& Henikoff, *Proc. Natl. Acad. Sci. USA* 89, 10915 (1989)).

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

Specific binding between two entities means an affinity of at least $10^6$, $10^7$, $10^8$, $10^9 M^{-1}$, or $10^{10} M^{-1}$. Affinities greater than $10^8 M^{-1}$ are preferred.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315–321 (1990); Kostelny et al., *J. Immunol.* 148, 1547–1553 (1992).

$APP^{695}$, $APP^{751}$, and APP770 refer, respectively, to the 695, 751, and 770 amino acid residue long polypeptides encoded by the human APP gene. See Kang et al., *Nature* 325, 773 (1987); Ponte et al., *Nature* 331, 525 (1988); and Kitaguchi et al., *Nature* 331, 530 (1988). Amino acids within the human amyloid precursor protein (APP) are assigned numbers according to the sequence of the APP770 isoform. Terms such as Aβ39, Aβ40, Aβ41, Aβ42 and Aβ43 refer to an Aβ peptide containing amino acid residues 1–39, 1–40, 1–41, 1–42 and 1–43.

An "antigen" is an entity to which an antibody specifically binds.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8–10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13–15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf. Dis.* 170, 1110–19 (1994)), by antigen-dependent killing (cytotoxic T lymphocyte assay, Tigges et al., *J. Immunol.* 156, 3901–3910) or by cytokine secretion.

The term "immunological" or "immune" response is the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays ($CD4^+$ T cells) or CTL (cytotoxic T lymphocyte) assays (see Burke, supra; Tigges, supra). The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "patient" includes human and other mammalian subjects that receive either prophylactic or therapeutic treatment.

Disaggregated or monomeric Aβ means soluble, monomeric peptide units of Aβ. One method to prepare monomeric Aβ is to dissolve lyophilized peptide in neat DMSO with sonication. The resulting solution is centrifuged to remove any insoluble particulates. Aggregated Aβ is a mixture of oligomers in which the monomeric units are held together by noncovalent bonds.

Competition between antibodies is determined by an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242–253 (1983)); solid phase direct biotin-avidin EIA (see Kirkland et al., J. Immunol. 137:3614–3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., Molec. Immunol. 25(1):7–15 (1988)); solid phase direct biotin-avidin EIA (Cheung et al., Virology 176:546–552 (1990)); and direct labeled RIA (Moldenhauer et al., Scand. J. Immunol. 32:77–82 (1990)). Typically, such an assay involves the use of purified antigen bound to a solid surface or cells bearing either of these, an unlabelled test immunoglobulin and a labelled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

Compositions or methods "comprising" one or more recited elements may include other elements not specifically recited. For example, a composition that comprises Aβ peptide encompasses both an isolated Aβ peptide and Aβ peptide as a component of a larger polypeptide sequence.

DETAILED DESCRIPTION

I. General

Several amyloidogenic diseases and conditions are characterized by presence of deposits of Aβ peptide aggregated to an insoluble mass in the brain of a patient. Such diseases include Alzheimer's disease, Down's syndrome and cognitive impairment. The latter is a symptom of Alzheimer's disease and Down's syndrome but can also without other characteristics of either of these diseases. For example, mild cognitive impairment or age-associated memory loss occurs in some patient who have not yet developed, or may never develop full Alzheimer's disease. Mild cognitive impairment can be defined by score on the Mini-Mental State Exam in accordance with convention. Such diseases are characterized by aggregates of Aβ that have a β-pleated sheet structure and stain with Congo Red dye. The basic approach of preventing or treating Alzheimer's disease or other amyloidogenic diseases by generating an immunogenic response to a component of the amyloid deposit in a patient is described in WO 99/27944 (incorporated by reference). The present application reiterates and confirms the efficacy of the basic approach. The present application is, however, principally directed to improved reagents and methods. These improvements are premised, in part, on the present inventors having localized the preferred epitopes within Aβ against which an immunogenic response should be directed. The identification of preferred epitopes within Aβ results in agents and methods having increased efficacy, reduced potential for side effects, and/or greater ease of manufacture, formulation and administration.

II. Therapeutic Agents

An immunogenic response can be active, as when an immunogen is administered to induce antibodies reactive with Aβ in a patient, or passive, as when an antibody is administered that itself binds to Aβ in a patient.

1. Agents Inducing Active Immune Response

Therapeutic agents induce an immunogenic response specifically directed to certain epitopes within Aβ peptides. Preferred agents are the Aβ peptide itself and segments thereof. Variants of such segments, analogs and mimetics of natural Aβ peptide that induce and/or crossreact with antibodies to the preferred epitopes of Aβ peptide can also be used.

Aβ, also known as β-amyloid peptide, or A4 peptide (see U.S. Pat. No. 4,666,829; Glenner & Wong, Biochem. Biophys. Res. Commun. 120, 1131 (1984)), is a peptide of 39–43 amino acids, which is the principal component of characteristic plaques of Alzheimer's disease. Aβ is generated by processing of a larger protein APP by two enzymes, termed β and γ secretases (see Hardy, TINS 20, 154 (1997)). Known mutations in APP associated with Alzheimer's disease occur proximate to the site of β or γ secretase, or within Aβ. For example, position 717 is proximate to the site of γ-secretase cleavage of APP in its processing to Aβ, and positions 670/671 are proximate to the site of β-secretase cleavage. It is believed that the mutations cause AD by interacting with the cleavage reactions by which Aβ is formed so as to increase the amount of the 42/43 amino acid form of Aβ generated.

Aβ has the unusual property that it can fix and activate both classical and alternate complement cascades. In particular, it binds to Clq and ultimately to C3bi. This association facilitates binding to macrophages leading to activation of B cells. In addition, C3bi breaks down further and then binds to CR2 on B cells in a T cell dependent manner leading to a 10,000 increase in activation of these cells. This mechanism causes Aβ to generate an immune response in excess of that of other antigens.

Aβ has several natural occurring forms. The human forms of Aβ are referred to as Aβ39, Aβ40, Aβ41, Aβ42 and Aβ43. The sequences of these peptides and their relationship to the APP precursor are illustrated by FIG. 1 of Hardy et al., TINS 20, 155–158 (1997). For example, Aβ42 has the sequence:

H$_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-OH (SEQ ID NO:42).

Aβ41, Aβ40 and Aβ39 differ from Aβ42 by the omission of Ala, Ala-lie, and Ala-fle-Val respectively from the C-terminal end. Aβ43 differs from Aβ42 by the presence of a threonine residue at the C-terminus.

Immunogenic fragments of Aβ are advantageous relative to the intact molecule in the present methods for several reasons. First, because only certain epitopes within Aβ induce a useful immunogenic response for treatment of Alzheimer's disease, an equal dosage of mass of a fragment containing such epitopes provides a greater molar concentration of the useful immunogenic epitopes than a dosage of intact Aβ. Second, certain immunogenic fragments of Aβ generate an immunogenic response against amyloid deposits without generating a significant immunogenic response against APP protein from which Aβ derives. Third, fragments of Aβ are simpler to manufacture than intact Aβ due to their shorter size. Fourth, fragments of Aβ do not aggregate in the same manner as intact Aβ, simplifying preparation of pharmaceutical compositions and administration thereof.

Some immunogenic fragments of Aβ have a sequence of at least 2, 3, 5, 6, 10 or 20 contiguous amino acids from a natural peptide. Some immunogenic fragments have no more than 10, 9, 8, 7, 5 or 3 contiguous residues from Aβ. Fragments from the N-terminal half of Aβ are preferred.

Preferred immunogenic fragments include Aβ1–5, 1–6, 1–7, 1–10, 3–7, 1–3, and 1–4. The designation Aβ1–5 for example, indicates a fragment including residues 1–5 of Aβ and lacking other residues of Aβ. Fragments beginning at residues 1–3 of Aβ and ending at residues 7–11 of Aβ are particularly preferred. The fragment Aβ1–12 can also be used but is less preferred. In some methods, the fragment is an N-terminal fragment other than Aβ1–10. Other less preferred fragments include Aβ13–28, 17–28, 1–28, 25–35, 35–40 and 35–42. These fragments require screening for activity in clearing or preventing amyloid deposits as described in the Examples before use. Fragments lacking at least one, and sometimes at least 5 or 10 C-terminal amino acid present in a naturally occurring forms of Aβ are used in some methods. For example, a fragment lacking 5 amino acids from the C-terminal end of Aβ43 includes the first 38 amino acids from the N-terminal end of Aβ. Other components of amyloid plaques, for example, synuclein, and epitopic fragments thereof can also be used to induce an immunogenic response.

Unless otherwise indicated, reference to Aβ includes the natural human amino acid sequences indicated above as well as analogs including allelic, species and induced variants. Analogs typically differ from naturally occurring peptides at one, two or a few positions, often by virtue of conservative substitutions. Analogs typically exhibit at least 80 or 90% sequence identity with natural peptides. Some analogs also include unnatural amino acids or modifications of N or C terminal amino acids at a one, two or a few positions. For example, the natural aspartic acid residue at position 1 and/or 7 of Aβ can be replaced with iso-aspartic acid. Examples of unnatural amino acids are D-amino acids, α,α-disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and isoaspartic acid. Fragments and analogs can be screened for prophylactic or therapeutic efficacy in transgenic animal models in comparison with untreated or placebo controls as described below.

Aβ, its fragments, and analogs can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., *Molecular Cloning: A Laboratory Manual* (C.S.H.P. Press, NY 2d ed., 1989). Some forms of Aβ peptide are also available commercially (e.g., American Peptides Company, Inc., Sunnyvale, Claif. and California Peptide Research, Inc. Napa, Calif.).

Therapeutic agents also include longer polypeptides that include, for example, an active fragment of Aβ peptide, together with other amino acids. For example, preferred agents include fusion proteins comprising a segment of Aβ fused to a heterologous amino acid sequence that induces a helper T-cell response against the heterologous amino acid sequence and thereby a B-cell response against the Aβ segment. Such polypeptides can be screened for prophylactic or therapeutic efficacy in animal models in comparison with untreated or placebo controls as described below. The Aβ peptide, analog, active fragment or other polypeptide can be administered in associated or multimeric form or in dissociated form Therapeutic agents also include multimers of monomeric immunogenic agents.

In a further variation, an immunogenic peptide, such as a fragment of Aβ, can be presented by a virus or a bacteria as part of an immunogenic composition. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outer surface protein of a virus or a transmembrane protein of a bacteria so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus, and other rhabdo viruses, vaccinia and fowl pox. Suitable bacteria include Salmonella and Shigella. Fusion of an immunogenic peptide to HBsAg of HBV is particularly suitable. Therapeutic agents also include peptides and other compounds that do not necessarily have a significant amino acid sequence similarity with Aβ but nevertheless serve as mimetics of Aβ and induce a similar immune response. For example, any peptides and proteins forming β-pleated sheets can be screened for suitability. Anti-idiotypic antibodies against monoclonal antibodies to Aβ or other amyloidogenic peptides can also be used. Such anti-Id antibodies mimic the antigen and generate an immune response to it (see *Essential Immunology* (Roit ed., Blackwell Scientific Publications, Palo Alto, 6th ed.), p. 181). Agents other than Aβ peptides should induce an immunogenic response against one or more of the preferred segments of Aβ listed above (e.g., 1–10, 1–7, 1–3, and 3–7). Preferably, such agents induce an immunogenic response that is specifically directed to one of these segments without being directed to other segments of Aβ.

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980.

Combinatorial libraries and other compounds are initially screened for suitability by determining their capacity to bind to antibodies or lymphocytes (B or T) known to be specific for Aβ or other amyloidogenic peptides. For example, initial screens can be performed with any polyclonal sera or monoclonal antibody to Aβ or a fragment thereof. Compounds can then be screened for binding to a specific epitope within Aβ (e.g., 1–10, 1–7, 1–3, 1–4, 1–5 and 3–7). Compounds can be tested by the same procedures described for mapping antibody epitope specificities. Compounds identified by such screens are then further analyzed for capacity to induce antibodies or reactive lymphocytes to Aβ or fragments thereof. For example, multiple dilutions of sera can be tested on microtiter plates that have been precoated with Aβ or a fragment thereof and a standard ELISA can be performed to test for reactive antibodies to Aβ or the fragment. Compounds can then be tested for prophylactic and therapeutic efficacy in transgenic animals predisposed to an amyloidogenic disease, as described in the Examples. Such animals include, for example, mice bearing a 717 mutation of APP described by Games et al., supra, and mice bearing a 670/671 Swedish mutation of APP such as described by McConlogue et al., U.S. Pat. No. 5,612,486 and Hsiao et al., Science 274, 99 (1996); Staufenbiel et al., Proc. Natl. Acad. Sci. USA 94, 13287–13292 (1997); Sturchler-Pierrat et al., Proc. Natl. Acad. Sci. USA 94, 13287–13292 (1997); Borchelt et al., Neuron 19, 939–945 (1997)). The same screening approach can be used on other potential agents analogs of Aβ and longer peptides including fragments of Aβ, described above.

2. Agents Inducing Passive Immune Response

Therapeutic agents of the invention also include antibodies that specifically bind to Aβ or other component of amyloid plaques. Such antibodies can be monoclonal or polyclonal. Some such antibodies bind specifically to the aggregated form of Aβ without binding to the dissociated form. Some bind specifically to the dissociated form without binding to the aggregated form. Some bind to both aggregated and dissociated forms. Some such antibodies bind to a naturally occurring short form of Aβ (i.e., Aβ39, 40 or 41) without binding to a naturally occurring long form of Aβ (i.e., Aβ42 and Aβ43). Some antibodies bind to a long form without binding to a short form. Some antibodies bind to Aβ without binding to full-length amyloid precursor protein. Antibodies used in therapeutic methods usually have an intact constant region or at least sufficient of the constant region to interact with an Fc receptor. Human isotype IgG1 is preferred because of it having highest affinity of human isotypes for the FcRI receptor on phagocytic cells. Bispecific Fab fragments can also be used, in which one arm of the antibody has specificity for Aβ, and the other for an Fc receptor. Some antibodies bind to Aβ with a binding affinity greater than or equal to about $10^6$, $10^7$, $10^8$, $10^9$, or $10^{10}$ $M^{-1}$.

Polyclonal sera typically contain mixed populations of antibodies binding to several epitopes along the length of Aβ. However, polyclonal sera can be specific to a particular segment of Aβ, such as Aβ1–10. Monoclonal antibodies bind to a specific epitope within Aβ that can be a conformational or nonconformational epitope. Prophylactic and therapeutic efficacy of antibodies can be tested using the transgenic animal model procedures described in the Examples. Preferred monoclonal antibodies bind to an epitope within residues 1–10 of Aβ (with the first N terminal residue of natural Aβ designated 1). Some preferred monoclonal antibodies bind to an epitope within amino acids 1–5, and some to an epitope within 5–10. Some preferred antibodies bind to epitopes within amino acids 1–3, 1–4, 1–5, 1–6, 1–7 or 3–7. Some preferred antibodies bind to an epitope starting at resides 1–3 and ending at residues 7–11 of Aβ. Less preferred antibodies include those binding to epitopes with residues 10–15, 15–20, 25–30, 10–20, 20, 30, or 10–25 of Aβ. It is recommended that such antibodies be screened for activity in the mouse model described in the Examples before use. For example, it has been found that certain antibodies to epitopes within residues 10–18, 16–24, 18–21 and 33–42 lack activity. In some methods, multiple monoclonal antibodies having binding specificities to different epitopes are used. Such antibodies can be administered sequentially or simultaneously. Antibodies to amyloid components other than Aβ can also be used. For example, antibodies can be directed to the amyloid associated protein synuclein.

When an antibody is said to bind to an epitope within specified residues, such as Aβ1–5 for example, what is meant is that the antibody specifically binds to a polypeptide containing the specified residues (i.e., Aβ1–5 in this an example). Such an antibody does not necessarily contact every residue within Aβ1–5. Nor does every single amino acid substitution or deletion with in Aβ1–5 necessarily significantly affect binding affinity. Epitope specificity of an antibody can be determined, for example, by forming a phage display library in which different members display different subsequences of Aβ. The phage display library is then selected for members specifically binding to an antibody under test. A family of sequences is isolated. Typically, such a family contains a common core sequence, and varying lengths of flanking sequences in different members. The shortest core sequence showing specific binding to the antibody defines the epitope bound by the antibody. Antibodies can also be tested for epitope specificity in a competition assay with an antibody whose epitope specificity has already been determined. For example, antibodies that compete with the 3D6 antibody for binding to Aβ bind to the same or similar epitope as 3D6, i.e., within residues Aβ1–5. Likewise antibodies that compete with the 10D5 antibody bind to the same or similar epitope, i.e., within residues Aβ3–6. Screening antibodies for epitope specificity is a useful predictor of therapeutic efficacy. For example, an antibody determined to bind to an epitope within residues 1–7 of Aβ is likely to be effective in preventing and treating Alzheimer's disease.

Monoclonal or polyclonal antibodies that specifically bind to a preferred segment of Aβ without binding to other regions of Aβ have a number of advantages relative to monoclonal antibodies binding to other regions or polyclonal sera to intact Aβ. First, for equal mass dosages, dosages of antibodies that specifically bind to preferred segments contain a higher molar dosage of antibodies effective in clearing amyloid plaques. Second, antibodies specifically binding to preferred segments can induce a clearing response against amyloid deposits without inducing a clearing response against intact APP polypeptide, thereby reducing the potential for side effects.

i. General Characteristics of Immunoglobulins

The basic antibody structural unit is known to comprise a tetramer of subunits. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989), Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of proteins of Immunological Interest* (National Institutes of Health, Bethesda, Md., 1987 and 1991), or Chothia & Lesk, *J. Mol. Biol.* 196:901–917(1987); Chothia et al., *Nature* 342:878–883 (1989).

ii. Production of Nonhuman Antibodies

The production of non-human monoclonal antibodies, e.g., murine, guinea pig, primate, rabbit or rat, can be accomplished by, for example, immunizing the animal with Aβ. A longer polypeptide comprising Aβ or an immunogenic fragment of Aβ or anti-idiotypic antibodies to an antibody to Aβ can also be used. See Harlow & Lane, *Antibodies, A Laboratory Manual* (CSHP NY, 1988) (incorporated by reference for all purposes). Such an immunogen can be obtained from a natural source, by peptide synthesis or by recombinant expression. Optionally, the immunogen can be administered fused or otherwise complexed with a carrier protein, as described below. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to Aβ. Optionally, antibodies are further screened for binding to a specific region of Aβ. The latter screening can be accomplished by determining binding of an antibody to a collection of deletion mutants of an Aβ peptide and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to Aβ. If the test and reference antibodies compete, then they bind to the same epitope or epitopes sufficiently proximal that binding of one antibody interferes with binding of the other. The preferred isotype for such antibodies is mouse isotype IgG2a or equivalent isotype in other species. Mouse isotype IgG2a is the equivalent of human isotype IgG1.

iii. Chimeric and Humanized Antibodies

Chimeric and humanized antibodies have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a mouse-antibody, (referred to as the donor immunoglobulin). See, Queen et al., *Proc. Natl Acad. Sci. USA* 86:10029–10033 (1989) and WO 90/07861, U.S. Pat. Nos. 5,693,762, 5,693,761, 5,585,089, 5,530,101 and Winter, U.S. Pat. No. 5,225,539 (incorporated by reference in their entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 A of a CDR region), or
(4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

iv. Human Antibodies

Human antibodies against Aβ are provided by a variety of techniques described below. Some human antibodies are selected by competitive binding experiments, or otherwise, to have the same epitope specificity as a particular mouse antibody, such as one of the mouse monoclonals described in Example XI. Human antibodies can also be screened for a particular epitope specificity by using only a fragment of Aβ as the immunogen, and/or by screening antibodies against a collection of deletion mutants of Aβ. Human antibodies preferably have isotype specificity human IgG1.

(1) Trioma Methodology

The basic approach and an exemplary cell fusion partner, SPAZ-4, for use in this approach have been described by Oestberg et al., *Hybridoma* 2:361–367 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells—two human and one mouse. Initially, a mouse myeloma line is fused with a human B-lymphocyte to obtain a non-antibody-producing xenogeneic hybrid cell, such as the SPAZ4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The immunized B-lymphocytes are obtained from the blood, spleen, lymph nodes or bone marrow of a human donor. If antibodies against a specific antigen or epitope are desired, it is preferable to use that antigen or epitope thereof for immunization. Immunization can be either in vivo or in vitro. For in vivo immunization, B cells are typically isolated from a human immunized with Aβ, a fragment thereof, larger polypeptide containing Aβ or fragment, or an anti-idiotypic antibody to an antibody to Aβ. In some methods, B cells are isolated from the same patient who is ultimately to be administered antibody therapy. For in vitro immunization, B-lymphocytes are typically exposed to antigen for a period of 7–14 days in a media such as RPMI-1640 (see Engleman, supra) supplemented with 10% human plasma.

The immunized B-lymphocytes are fused to a xenogeneic hybrid cell such as SPAZ4 by well known methods. For example, the cells are treated with 40–50% polyethylene glycol of MW 1000–4000, at about 37 degrees C, for about 5–10 min. Cells are separated from the fusion mixture and propagated in media selective for the desired hybrids (e.g., HAT or AH). Clones secreting antibodies having the required binding specificity are identified by assaying the trioma culture medium for the ability to bind to Aβ or a fragment thereof. Triomas producing human antibodies having the desired specificity are subcloned by the limiting dilution technique and grown in vitro in culture medium. The trioma cell lines obtained are then tested for the ability to bind Aβ or a fragment thereof.

Although triomas are genetically stable they do not produce antibodies at very high levels. Expression levels can be increased by cloning antibody genes from the trioma into one or more expression vectors, and transforming the vector into standard mammalian, bacterial or yeast cell lines.

(2) Transgenic Non-Human Mammals

Human antibodies against Aβ can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., W093/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, *Nature* 148, 1547–1553 (1994), *Nature Biotechnology* 14, 826 (1996), Kucherlapati, WO 91/10741 (1991) (each of which is incorporated by reference in its entirety for all purposes). Transgenic mice are particularly suitable. Anti-Aβ antibodies are obtained by immunizing a transgenic nonhuman mammal, such as described by Lonberg or Kucherlapati, supra, with Aβ or a fragment thereof. Monoclonal antibodies are prepared by, e.g., fusing B-cells from such mammals to suitable myeloma cell lines using conventional Kohler-Milstein technology. Human polyclonal antibodies can also be provided in the form of serum from humans immunized with an immunogenic agent. Optionally, such polyclonal antibodies can be concentrated by affinity purification using Aβ or other amyloid peptide as an affinity reagent.

(3) Phage Display Methods

A further approach for obtaining human anti-Aβ antibodies is to screen a DNA library from human B cells according to the general protocol outlined by Huse et al., *Science* 246:1275–1281 (1989). As described for trioma methodology, such B cells can be obtained from a human immunized with Aβ, fragments, longer polypeptides containing Aβ or fragments or anti-idiotypic antibodies. Optionally, such B cells are obtained from a patient who is ultimately to receive antibody treatment. Antibodies binding to Aβ or a fragment thereof are selected. Sequences encoding such antibodies (or a binding fragments) are then cloned and amplified. The protocol described by Huse is rendered more efficient in combination with phage-display technology. See, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332 (each of which is incorporated by reference in its entirety for all purposes). In these methods, libraries of phage are produced in which members display different antibodies on their outer surfaces. Antibodies are usually displayed as Fv or Fab fragments. Phage displaying antibodies with a desired specificity are selected by affinity enrichment to an Aβ peptide or fragment thereof.

In a variation of the phage-display method, human antibodies having the binding specificity of a selected murine antibody can be produced. See Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for Aβ (e.g., at least $10^8$ and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for Aβ are selected. These phage display the variable regions of completely human anti-Aβ antibodies. These antibodies usually have the same or similar epitope specificity as the murine starting material.

v. Selection of Constant Region

The heavy and light chain variable regions of chimeric, humanized, or human antibodies can be linked to at least a portion of a human constant region. The choice of constant region depends, in part, whether antibody-dependent complement and/or cellular mediated toxicity is desired. For example, isotopes IgG1 and IgG3 have complement activity and isotypes IgG2 and IgG4 do not. Choice of isotype can also affect passage of antibody into the brain. Human isotype IgG1 is preferred. Light chain constant regions can be lambda or kappa. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

vi. Expression of Recombinant Antibodies

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, gel electrophoresis and the like (see generally, Scopes, *Protein Purification* (Springer-Verlag, NY, 1982)).

3. Carrier Proteins

Some agents for inducing an immune response contain the appropriate epitope for inducing an immune response against amyloid deposits but are too small to be immunogenic. In this situation, a peptide immunogen can be linked to a suitable carrier to help elicit an immune response. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. Other carriers include T-cell epitopes that bind to multiple MHC alleles, e.g., at least 75% of all human MHC alleles. Such carriers are sometimes known in the art as "universal T-cell epitopes." Examples of universal T-cell epitopes include:

Influenza Hemagluttinin: $HA_{307-319}$ PKYVKQNTLKLAT (SEQ ID NO:43)

PADRE (common residues bolded) AKXVAAWTL-KAAA (SEQ ID NO:44)

Malaria CS: T3 epitope EKKIAKMEKASSVFNV (SEQ ID NO:45)

Hepatitis B surface antigen: $HBsAg_{19-28}$ FFLLTRILTI (SEQ ID NO:46)

Heat Shock Protein 65: $hsp65_{153-171}$ DQSIGDLIAEAM-DKVGNEG (SEQ ID NO:47)

bacille Calmette-Guerin QVHFQPLPPAVVKL (SEQ ID NO:48)

Tetanus toxoid: $TT_{830-844}$ QYIKANSKFIGITEL (SEQ ID NO:49)

Tetanus toxoid: $TT_{947-967}$ FNNFTVSFWLRVP-KVSASHLE (SEQ ID NO:50)

HIV gp120 T1: KQIINMWQEVGKAMYA (SEQ ID NO:51).

Other carriers for stimulating or enhancing an immune response include cytokines such as IL-1, IL-1 α and β peptides, IL-2, γINF, IL-10, GM-CSF, and chemokines, such as MIP1α and β and RANTES. Immunogenic agents can also be linked to peptides that enhance transport across tissues, as described in O'Mahony, WO 97/17613 and WO 97/17614.

Immunogenic agents can be linked to carriers by chemical crosslinking. Techniques for linking an immunogen to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the ε-amino on a lysine, or other free amino group in other amino acids. A variety of such disulfide/amide-forming agents are described by *Immun. Rev.* 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimidomethyl)cyclohexane-1-carboxylic acid. The carboxyl groups can be activated by combining them with succinimide or 1-hydroxyl-2-nitro-4-sulfonic acid, sodium salt.

Immunogenic peptides can also be expressed as fusion proteins with carriers (i.e., heterologous peptides). The immunogenic peptide can be linked at its amino terminus, its carboxyl terminus, or both to a carrier. Optionally, multiple repeats of the immunogenic peptide can be present in the fusion protein. Optionally, an immunogenic peptide can be linked to multiple copies of a heterologous peptide, for example, at both the N and C termini of the peptide. Some carrier peptides serve to induce a helper T-cell response against the carrier peptide. The induced helper T-cells in turn induce a B-cell response against the immunogenic peptide linked to the carrier peptide.

Some agents of the invention comprise a fusion protein in which an N-terminal fragment of Aβ is linked at its C-terminus to a carrier peptide. In such agents, the N-terminal residue of the fragment of Aβ constitutes the N-terminal residue of the fusion protein. Accordingly, such fusion proteins are effective in inducing antibodies that bind to an epitope that requires the N-terminal residue of Aβ to be in free form. Some agents of the invention comprises a plurality of repeats of an N-terminal segment of Aβ linked at the C-terminus to one or more copy of a carrier peptide. The N-terminal fragment of Aβ incorporated into such fusion proteins sometimes begins at Aβ1–3 and ends at Aβ7–11. Aβ1–7, Aβ1–3, 1–4, 1–5, and 3–7 are preferred N-terminal fragment Aβ. Some fusion proteins comprise different N-terminal segments of Aβ in tandem. For example, a fusion protein can comprise Aβ1–7 followed by Aβ1–3 followed by a heterologous peptide.

In some fusion proteins, an N-terminal segment of Aβ is fused at its N-terminal end to a heterologous carrier peptide. The same variety of N-terminal segments of Aβ can be used as with C-terminal fusions. Some fusion proteins comprise a heterologous peptide linked to the N-terminus of an N-terminal segment of Aβ, which is in turn linked to one or more additional N-terminal segments of Aβ in tandem.

Some examples of fusion proteins suitable for use in the invention are shown below. Some of these fusion proteins comprise segments of Aβ linked to tetanus toxoid epitopes such as described in U.S. Pat. No. 5,196,512, EP 378,881 and EP 427,347. Some fusion proteins comprises segments of Aβ linked to carrier peptides described in U.S. Pat. No. 5,736,142. Some heterologous peptides are universal T-cell epitopes. In some methods, the agent for administration is simply a single fusion protein with an Aβ segment linked to a heterologous segment in linear configuration. In some methods, the agent is multimer of fusion proteins represented by the formula $2^x$, in which x is an integer from 1–5. Preferably x is 1, 2 or 3, with 2 being most preferred. When x is two, such a multimer has four fusion proteins linked in a preferred configuration referred to as MAP4 (see U.S. Pat. No. 5,229,490). Epitopes of Aβ are underlined.

The MAP4 configuration is shown below, where branched structures are produced by initiating peptide synthesis at both the N terminal and side chain amines of lysine. Depending upon the number of times lysine is incorporated into the sequence and allowed to branch, the resulting structure will present multiple N termini. In this example, four identical N termini have been produced on the branched lysine-containing core. Such multiplicity greatly enhances the responsiveness of cognate B cells.

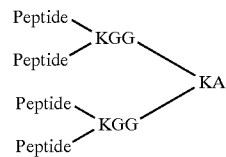

AN90549 (Aβ1–7/Tetanus toxoid 830–844 in a MAP4 configuration):

<u>DAEFRHD</u>QYIKANSKFIGITEL (SEQ ID NO:52)

AN90550 (Aβ1–7/Tetanus toxoid 947–967 in a MAP4 configuration):

<u>DAEFRHD</u>FNNFTVSFWLRVPKVSASHLE (SEQ ID NO:53)

AN90542 (Aβ1–7/Tetanus toxoid 830–844+947–967 in a linear configuration):

<u>DAEFRHD</u>QYIKANSKFIGITELFNNFTVSFWLRV PKVSASHLE (SEQ ID NO:54)

AN90576: (Aβ3–9)/Tetanus toxoid 830–844 in a MAP4 configuration):

<u>EFRHDSG</u>QYIKANSKFIGITEL (SEQ ID NO:55)

Peptide described in U.S. Pat. No. 5,736,142 (all in linear configurations):

AN90562 (Aβ1–7/peptide) AKXVAAWTLKAAA <u>DAEFRHD</u> (SEQ ID NO:56)

AN90543 (Aβ1–7×3/ peptide): <u>DAEFRHDDAEFRHDDAEFRHD</u>AKXVAAWTL KAAA (SEQ ID NO:57)

Other examples of fusion proteins (immunogenic epitope of Aβ bolded) include

AKXVAAWTLKAAA-DAEFRHD-DAEFRHD-DAEFRHD DAEFRHD-AKXVAAWTLKAAA (SEQ ID NO:59)

DAEFRHD-ISQAVHAAHAEINEAGR (SEQ ID NO:60)

FRHDSGY-ISQAVHAAHAEINEAGR (SEQ ID NO:61)

EFRHDSG-ISQAVHAAHAEINEAGR (SEQ ID NO:62)

PKYVKQNTLKLAT-DAEFRHD-DAEFRHD-DAEFRHD (SEQ ID NO:63)

DAEFRHD-PKYVKQNTLKLAT-DAEFRHD (SEQ ID NO:64)

DAEFRHD-DAEFRHD-DAEFRHD-PKYVKQNTLKLAT (SEQ ID NO:65)

DAEFRHD-DAEFRHD-PKYVKQNTLKLAT (SEQ ID NO:66)

DAEFRHD-PKYVKQNTLKLAT-EKKIAKMEKASSVFNV-QYIKANSKFIGITEL-FNNFTVSFWLRVPKVSASHLE-DAEFRHD (SEQ ID NO:67)

DAEFRHD-DAEFRHD-DAEFRHD-QYIKANSKFIGITEL-FNNFTVSFWLRVPKVSASHLE (SEQ ID NO:68)

DAEFRHD-QYIKANSKFIGITELCFNNFTVSFWL-RVPKVSASHLE (SEQ ID NO:69)

DAEFRHD-QY KANSKFIGITELCFNNFTVSFWLRVPKVSASHLE-DAEFRHD (SEQ ID NO:70)

DAEFRHD-QYIKANSKFIGITEL on a 2 branched resin (SEQ ID NO:77)

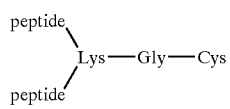

EQVTNVGGAISQAVHAAHAEINEAGR (SEQ ID NO:71) (Synuclein fusion protein in MAP4 configuration).

The same or similar carrier proteins and methods of linkage can be used for generating immunogens to be used in generation of antibodies against Aβ for use in passive immunization. For example, Aβ or a fragment linked to a carrier can be administered to a laboratory animal in the production of monoclonal antibodies to Aβ.

4. Nucleic Acid Encoding Therapeutic Agents

Immune responses against amyloid deposits can also be induced by administration of nucleic acids encoding segments of Aβ peptide, and fragments thereof, other peptide immunogens, or antibodies and their component chains used for passive immunization. Such nucleic acids can be DNA or RNA. A nucleic acid segment encoding an immunogen is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see, e.g., Lawrie and Tumin, *Cur. Opin. Genet. Develop.* 3, 102–109 (1993)); adenoviral vectors (see, e.g., Bett et al., *J. Virol.* 67, 5911 (1993)); adeno-associated virus vectors (see, e.g., Zhou et al., *J. Exp. Med* 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70, 508–519 (1996)), Venezuelan equine encephalitis virus (see U.S. Pat. No. 5,643,576) and rhabdoviruses, such as vesicular stomatitis virus (see WO 96/34625)and papillomaviruses (Ohe et al., *Human Gene Therapy* 6, 325–333 (1995); Woo et al., WO 94/12629 and Xiao & Brandsma, *Nucleic Acids. Res.* 24, 2630–2622 (1996)).

DNA encoding an immunogen, or a vector containing the same, can be packaged into liposomes. Suitable lipids and related analogs are described by U.S. Pat. Nos. 5,208,036, 5,264,618, 5,279,833 and 5,283,185. Vectors and DNA encoding an immunogen can also be adsorbed to or associated with particulate carriers, examples of which include polymethyl methacrylate polymers and polylactides and poly(lactide-co-glycolides), see, e.g., McGee et al., *J. Micro Encap.* (1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). Such vectors can further include facilitating agents such as bupivacine (U.S. Pat. No. 5,593,970). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see WO 95/05853).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

III. Screening Antibodies for Clearing Activity

The invention provides methods of screening an antibody for activity in clearing an amyloid deposit or any other antigen, or associated biological entity, for which clearing activity is desired. To screen for activity against an amyloid deposit, a tissue sample from a brain of a patient with Alzheimer's disease or an animal model having characteristic Alzbeimer's pathology is contacted with phagocytic cells bearing an Fc receptor, such as microglial cells, and the antibody under test in a medium in vitro. The pagocytic cells can be a primary culture or a cell line, such as BV-2, C8-B4, or THP-1. In some methods, the components are combined on a microscope slide to facilitate microscopic monitoring. In some methods, multiple reactions are performed in parallel in the wells of a microtiter dish. In such a format, a separate miniature microscope slide can be mounted in the separate wells, or a nonmicroscopic detection format, such as ELISA detection of Aβ can be used. Preferably, a series of measurements is made of the amount of amyloid deposit in the in vitro reaction mixture, starting from a baseline value before the reaction has proceeded, and one or more test values during the reaction. The antigen can be detected by staining, for example, with a fluorescently labelled antibody to Aβ or other component of amyloid plaques. The antibody used for staining may or may not be the same as the antibody being tested for clearing activity. A reduction relative to baseline during the reaction of the amyloid deposits indicates that the antibody under test has clearing activity. Such antibodies are likely to be useful in preventing or treating Alzheimer's and other amyloidogenic diseases.

Analogous methods can be used to screen antibodies for activity in clearing other types of biological entities. The assay can be used to detect clearing activity against virtually any kind of biological entity. Typically, the biological entity has some role in human or animal disease. The biological entity can be provided as a tissue sample or in isolated form. If provided as a tissue sample, the tissue sample is preferably unfixed to allow ready access to components of the tissue sample and to avoid perturbing the conformation of the components incidental to fixing. Examples of tissue samples that can be tested in this assay include cancerous tissue, precancerous tissue, tissue containing benign growths such as warts or moles, tissue infected with pathogenic microorganisms, tissue infiltrated with inflammatory cells, tissue bearing pathological matrices between cells (e.g., fibrinous pericarditis), tissue bearing aberrant antigens, and scar tissue. Examples of isolated biological entities that can be used include Aβ, viral antigens or viruses, proteoglycans, antigens of other pathogenic microorganisms, tumor antigens, and adhesion molecules. Such antigens can be obtained from natural sources, recombinant expression or chemical synthesis, among other means. The tissue sample or isolated biological entity is contacted with phagocytic cells bearing Fc receptors, such as monocytes or microglial cells, and an antibody to be tested in a medium. The antibody can be directed to the biological entity under test or to an antigen associated with the entity In the latter situation, the object is to test whether the biological entity is vicariously phagocytosed with the antigen. Usually, although not necessarily, the antibody and biological entity (sometimes with an associated antigen) are contacted with each other before adding the phagocytic cells. The concentration of the biological entity and/or the associated antigen, if present, remaining in the medium is then monitored. A reduction in the amount or concentration of antigen or the associated biological entity in the medium indicates the antibody has a clearing response against the antigen and/or associated biological entity in conjunction with the phagocytic cells (see, e.g., Example 14).

IV. Patients Amenable to Treatment

Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are especially useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and A$\beta$42 levels. Elevated tau and decreased A$\beta$42 levels signify the presence of AD. Individuals suffering from Alzheimer's disease can also be diagnosed by ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to the therapeutic agent (e.g., A$\beta$ peptide) over time. If the response falls, a booster dosage is indicated. In the case of potential Down's syndrome patients, treatment can begin antenatally by administering therapeutic agent to the mother or shortly after birth.

V. Treatment Regimes

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. In some methods, administration of agent reduces or eliminates myocognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy. The amount of immunogen depends on whether adjuvant is also administered, with higher dosages being required in the absence of adjuvant. The amount of an immunogen for administration sometimes varies from 1–500 $\mu$g per patient and more usually from 5–500 $\mu$g per injection for human administration. Occasionally, a higher dose of 1–2 mg per injection is used. Typically about 10, 20, 50 or 100 $\mu$g is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for microgram of immunogen. The timing of injections can vary significantly from once a day, to once a year, to once a decade. On any given day that a dosage of immunogen is given, the dosage is greater than 1 $\mu$g/patient and usually greater than 10 $\mu$g/ patient if adjuvant is also administered, and greater than 10 $\mu$g/patient and usually greater than 100 $\mu$g/patient in the absence of adjuvant. A typical regimen consists of an immunization followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1–10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to Aβ in the patient. In some methods, dosage is adjusted to achieve a plasma antibody concentration of 1–1000 ug/ml and in some methods 25–300 ug/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 μg to 10 mg, or 30–300 μg DNA per patient. Doses for infectious viral vectors vary from 10–100, or more, virions per dose.

Agents for inducing an immune response can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection on intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treatment of amyloidogenic disease. In the case of Alzheimer's and Down's syndrome, in which amyloid deposits occur in the brain, agents of the invention can also be administered in conjunction with other agents that increase passage of the agents of the invention across the blood-brain barrier.

Immunogenic agents of the invention, such as peptides, are sometimes administered in combination with an adjuvant. A variety of adjuvants can be used in combination with a peptide, such as Aβ, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in Vaccine Design: *The Subunit and Adjuvant Approach* (eds. Powell & Newman, Plenum Press, NY, 1995); U.S. Pat. No. 5,057,540),(Aquila BioPhannaceuticals, Framingham, Mass.). Other adjuvants are oil in water emulsions (such as squalene or peanut oil), optionally in combination with immune stimulants, such as monophosphoryl lipid A (see Stoute et al., *N. Engl. J. Med.* 336, 86–91 (1997)). Another adjuvant is CpG (WO 98/40100). Alternatively, Aβ can be coupled to an adjuvant. However, such coupling should not substantially change the conformation of Aβ so as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as aluminum hydroxide, aluminum phosphate, aluminum sulfate. Such adjuvants can be used with or without other specific immunostimulating agents such as MPL or 3-DMP, QS-21, polymeric or monomeric amino acids such as polyglutamic acid or polylysine: Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton, Mont.) containing 2% squalene, 0.2% Tween 80, and one or more bacterial cell wall components from the group consisting of monophosphoryllipid A (MPL), trehalose dimycolate (TDM), and cell wall skeleton (CWS), preferably MPL+CWS (Detox™). Another class of preferred adjuvants is saponin adjuvants, such as Stimulon™ (QS-21, Aquila, Framingham, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, and alum, QS-21 and MPL together. Also, Incomplete Freund's adjuvant can be used (Chang et al., *Advanced Drug Delivery Reviews* 32, 173–186 (1998)), optionally in combination with any of alum, QS-21, and MPL and all combinations thereof.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized sepharose(™), agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles priorto injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97–119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%–2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%–95% of active ingredient, preferably 25%–70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., *Eur. J. Immunol.* 25, 3521–24 (1995); Cevc et al., *Biochem. Biophys. Acta* 1368, 201–15 (1998)).

VI. Methods of Diagnosis

The invention provides methods of detecting an immune response against Aβ peptide in a patient suffering from or susceptible to Alzheimer's disease. The methods are particularly useful for monitoring a course of treatment being administered to a patient. The methods can be used to monitor both therapeutic treatment on symptomatic patients and prophylactic treatment on asymptomatic patients. The methods are useful for monitoring both active immunization (e.g., antibody produced in response to administration of immunogen) and passive immunization (e.g., measuring level of administered antibody).

1. Active Immunization

Some methods entail determining a baseline value of an immune response in a patient before administering a dosage of agent, and comparing this with a value for the immune response after treatment. A significant increase (i.e., greater than the typical margin of experimental error in repeat measurements of the same sample, expressed as one standard deviation from the mean of such measurements) in value of the immune response signals a positive treatment outcome (i.e., that administration of the agent has achieved or augmented an immune response). If the value for immune response does not change significantly, or decreases, a negative treatment outcome is indicated. In general, patients undergoing an initial course of treatment with an immunogenic agent are expected to show an increase in immune response with successive dosages, which eventually reaches a plateau. Administration of agent is generally continued while the immune response is increasing. Attainment of the plateau is an indicator that the administered of treatment can be discontinued or reduced in dosage or frequency.

In other methods, a control value (i.e., a mean and standard deviation) of immune response is determined for a control population. Typically the individuals in the control population have not received prior treatment. Measured values of immune response in a patient after administering a therapeutic agent are then compared with the control value. A significant increase relative to the control value (e.g., greater than one standard deviation from the mean) signals a positive treatment outcome. A lack of significant increase or a decrease signals a negative treatment outcome. Administration of agent is generally continued while the immune response is increasing relative to the control value. As before, attainment of a plateau relative to control values in an indicator that the administration of treatment can be discontinued or reduced in dosage or frequency.

In other methods, a control value of immune response (e.g., a mean and standard deviation) is determined from a control population of individuals who have undergone treatment with a therapeutic agent and whose immune responses have plateaued in response to treatment. Measured values of immune response in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment regime, for example, use of a different adjuvant may be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucous or cerebrospinal fluid from the patient. The sample is analyzed for indication of an immune response to any form of $A\beta$ peptide, typically $A\beta42$. The immune response can be determined from the presence of, e.g., antibodies or T-cells that specifically bind to $A\beta$ peptide. ELISA methods of detecting antibodies specific to $A\beta$ are described in the Examples section. Methods of detecting reactive T-cells have been described above (see Definitions). In some methods, the immune response is determined using a clearing assay, such as described in Section III above. In such methods, a tissue sample from a patient being tested is contacted with amyloid deposits (e.g., from a PDAPP mouse) and phagocytic cells bearing Fc receptors. Subsequent clearing of the amyloid deposit is then monitored. The existence and extent of clearing response provides an indication of the existence and level of antibodies effective to clear $A\beta$ in the tissue sample of the patient under test.

2. Passive Immunization

In general, the procedures for monitoring passive immunization are similar to those for monitoring active immunization described above. However, the antibody profile following passive immunization typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to $A\beta$ in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

3. Diagnostic Kits

The invention further provides diagnostic kits for performing the diagnostic methods described above. Typically, such kits contain an agent that specifically binds to antibodies to $A\beta$. The kit can also include a label. For detection of antibodies to $A\beta$, the label is typically in the form of labelled anti-idiotypic antibodies. For detection of antibodies, the agent can be supplied prebound to a solid phase, such as to the wells of a microtiter dish. Kits also typically contain labeling providing directions for use of the kit. The labeling may also include a chart or other correspondence regime correlating levels of measured label with levels of antibodies to $A\beta$. The term labeling refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

The invention also provides diagnostic kits for performing in vivo imaging. Such kits typically contain an antibody binding to an epitope of $A\beta$, preferably within residues 1–10. Preferably, the antibody is labelled or a secondary labeling reagent is included in the kit. Preferably, the kit is labelled with instructions for performing an in vivo imaging assay.

VII. In Vivo Imaging

The invention provides methods of in vivo imaging amyloid deposits in a patient. Such methods are useful to diagnose or confirm diagnosis of Alzheimer's disease, or susceptibility thereto. For example, the methods can be used on a patient presenting with symptoms of dementia. If the patient has abnormal amyloid deposits, then the patient is likely suffering from Alzheimer's disease. The methods can also be used on asymptomatic patients. Presence of abnormal deposits of amyloid indicates susceptibility to future symptomatic disease. The methods are also useful for monitoring disease progression and/or response to treatment in patients who have been previously diagnosed with Alzheimer's disease.

The methods work by administering a reagent, such as antibody, that binds to $A\beta$ in the patient, and then detecting the agent after it has bound. Preferred antibodies bind to $A\beta$ deposits in a patient without binding to full length APP polypeptide. Antibodies binding to an epitope of Aβ within amino acids 1–10 are particularly preferred. In some methods, the antibody binds to an epitope within amino acids 7–10 of Aβ. Such antibodies typically bind without inducing a substantial clearing response. In other methods, the antibody binds to an epitope within amino acids 1–7 of Aβ. Such antibodies typically bind and induce a clearing response to Aβ. However, the clearing response can be avoided by using antibody fragments lacking a full length constant region, such as Fabs. In some methods, the same antibody can serve as both a treatment and diagnostic reagent. In general, antibodies binding to epitopes C-terminal of residue 10 of Aβ do not show as strong signal as antibodies binding to epitopes within residues 1–10, presumably because the C-terminal epitopes are inaccessible in amyloid deposits. Accordingly, such antibodies are less preferred.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labelled, although in some methods, the primary reagent with affinity for Aβ is unlabelled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size and/or intensity of labelled loci to corresponding base line values. The base line values can represent the mean levels in a population of undiseased individuals. Base line values can also represent previous levels determined in the same patient. For example, base line values can be determined in a patient before beginning treatment, and measured values thereafter compared with the base line values. A decrease in values relative to base line signals a positive response to treatment.

EXAMPLES

1. Prophylactic Efficacy of Aβ Against AD

These examples describe administration of Aβ42 peptide to transgenic mice overexpressing APP with a mutation at position 717 (APP$_{717v \to F}$) that predisposes them to develop Alzheimer's-like neuropathology. Production and characteristics of these mice (PDAPP mice) is described in Games et al., *Nature*, supra. These animals, in their heterozygote form, begin to deposit Aβ at six months of age forward. By fifteen months of age they exhibit levels of Aβ deposition equivalent to that seen in Alzheimer's disease. PDAPP mice were injected with aggregated Aβ$_{42}$ (aggregated Aβ$_{42}$) or phosphate buffered saline. Aggregated Aβ$_{42}$ was chosen because of its ability to induce antibodies to multiple epitopes of Aβ.

A. Methods

1. Source of Mice

Thirty PDAPP heterogenic female mice were randomly divided into the following groups: 10 mice to be injected with aggregated Aβ42 (one died in transit), 5 mice to be injected with PBS/adjuvant or PBS, and 10 uninjected controls. Five mice were injected with peptides derived from the sequence of serum amyloid protein (SAP).

2. Preparation of Immunogens

Preparation of aggregated Aβ42: two milligrams of Aβ42 (U.S. Peptides Inc, lot K-42-12) was dissolved in 0.9 ml water and made up to 1 ml by adding 0.1 ml 10 ×PBS. This was vortexed and allowed to incubate overnight 37° C., under which conditions the peptide aggregated. Any unused Aβ was stored as a dry lyophilized powder at −20° C. until the next injection.

3. Preparation of Injections

For each injection, 100 μg of aggregated Aβ42 in PBS per mouse was emulsified 1:1 with Complete Freund's adjuvant (CFA) in a final volume of 400 μl emulsion for the first immunization, followed by a boost of the same amount of immunogen in Incomplete Freund's adjuvant (IFA) at 2 weeks. Two additional doses in IFA were given at monthly intervals. The subsequent immunizations were done at monthly intervals in 500 μl of PBS. Injections were delivered intraperitoneally (i.p.).

PBS injections followed the same schedule and mice were injected with a 1:1 mix of PBS/ Adjuvant at 400 μl per mouse, or 500 μl of PBS per mouse. SAP injections likewise followed the same schedule using a dose of 100 μg per injection.

4. Titration of Mouse Bleeds, Tissue Preparation and Immunohistochemistry

The above methods are described infra in General Materials and Methods.

B. Results

PDAPP mice were injected with either aggregated Aβ42 (aggregated Aβ42), SAP peptides, or phosphate buffered saline. A group of PDAPP mice were also left as uninjected, positive controls. The titers of the mice to aggregated Aβ42 were monitored every other month from the fourth boost until the mice were one year of age. Mice were sacrificed at 13 months. At all time points examined, eight of the nine aggregated Aβ42 mice developed a high antibody titer, which remained high throughout the series of injections (titers greater than 1/10000). The ninth mouse had a low, but measurable titer of approximately 1/1000 (FIG. 1, Table 1). SAPP-injected mice had titers of 1:1,000 to 1:30,000 for this immunogen with only a single mouse exceeding 1:10,0000.

The PBS-treated mice were titered against aggregated Aβ42 at six, ten and twelve months. At a 1/100 dilution the PBS mice, when titered against aggregated Aβ42, only exceeded 4 times background at one data point, otherwise, they were less than 4 times background at all time points (Table 1). The SAP-specific response was negligible at these time points with all titers less than 300.

Seven out of the nine mice in the aggregated Aβ1–42 treated group had no detectable amyloid in their brains. In contrast, brain tissue from mice in the SAP and PBS groups contained numerous amyloid deposits in the hippocampus, as well as in the frontal and cingulate cortices. The pattern of deposition was similar to that of untreated controls, with characteristic involvement of vulnerable subregions, such as the outer molecular layer of the hippocampal dentate gyrus. One mouse from the Aβ1–42-injected group had a greatly reduced amyloid burden, confined to the hippocampus. An isolated plaque was identified in another Aβ1–42-treated mouse.

Figure 2:
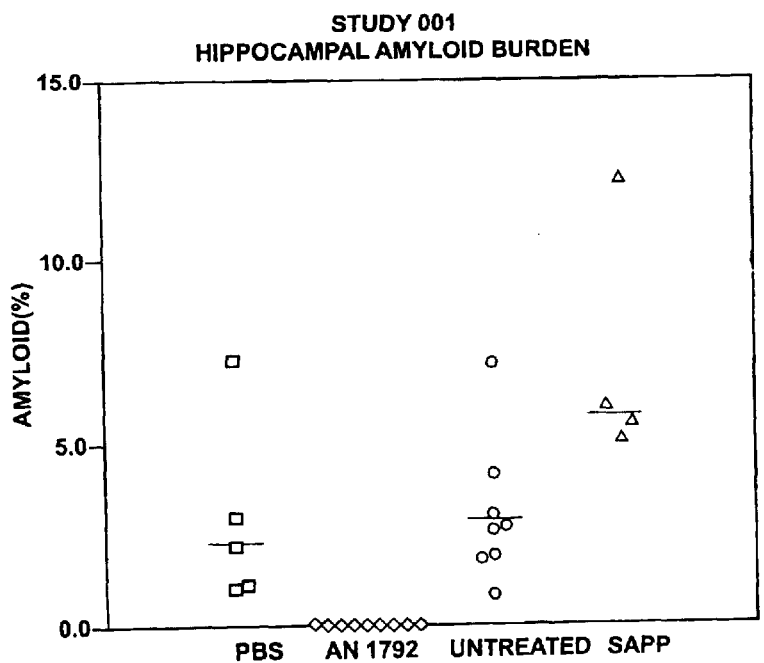
FIG. 2: Amyloid burden in the hippocampus. The percentage of the area of the hippocampal region occupied by amyloid plaques, defined by reactivity with the Aβ-specific monoclonal antibody 3D6, was determined by computer-assisted quantitative image analysis of immunoreacted brain sections. The values for individual mice are shown sorted by treatment group. The horizontal line for each grouping indicates the median value of the distribution.

Quantitative image analyses of the amyloid burden in the hippocampus verified the dramatic reduction achieved in the Aβ42(AN1792)-treated animals (FIG. 2). The median values of the amyloid burden for the PBS group (2.22%), and for the untreated control group (2.65%) were significantly greater than for those immunized with AN1792 (0.00%, p=0.0005). In contrast, the median value for the group immunized with SAP peptides (SAPP) was 5.74%. Brain tissue from the untreated, control mice contained numerous Aβ amyloid deposits visualized with the A P-specific monoclonal antibody (mAb) 3D6 in the hippocampus, as well as in the retrosplenial cortex. A similar pattern of amyloid deposition was also seen in mice immunized with SAPP or PBS (FIG. 2). In addition, in these latter three groups there was a characteristic involvement of vulnerable subregions of the brain classically seen in Aβ, such as the outer molecular layer of the hippocampal dentate gyrus, in all three of these groups.

Figure 3:
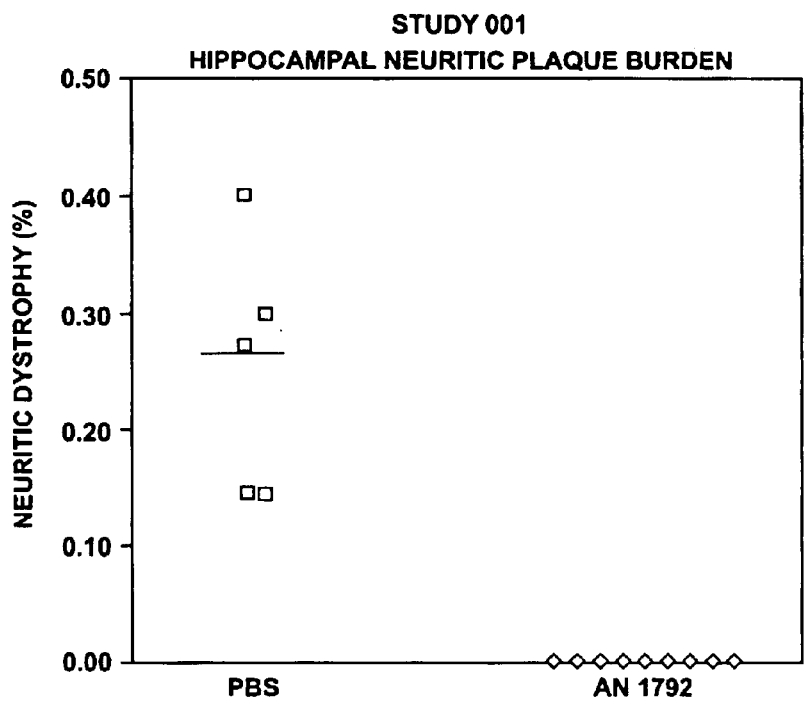
FIG. 3: Neuritic dystrophy in the hippocampus. The percentage of the area of the hippocampal region occupied by dystrophic neurites, defined by their reactivity with the human APP-specific monoclonal 8E5, was determined by quantitative computer-assisted image analysis of immunoreacted brain sections. The values for individual mice are shown for the AN1792-treated group and the PBS-treated control group. The horizontal line for each grouping indicates the median value of the distribution.

The brains that contained no Aβ deposits were also devoid of neuritic plaques that are typically visualized in PDAPP mice with the human APP antibody 8E5. All of brains from the remaining groups (SAP-injected, PBS and uninjected mice) had numerous neuritic plaques typical of untreated PDAPP mice. A small number of neuritic plaques were present in one mouse treated with AN1792, and a single cluster of dystrophic neurites was found in a second mouse treated with AN1792. Image analyses of the hippocampus, and shown in FIG. 3, demonstrated the virtual elimination of dystrophic neurites in AN1792-treated mice (median 0.00%) compared to the PBS recipients (median 0.28%, p=0.0005).

Astrocytosis characteristic of plaque-associated inflammation was also absent in the brains of the Aβ1–42 injected group. The brains from the mice in the other groups contained abundant and clustered GFAP-positive astrocytes typical of Aβ plaque-associated gliosis. A subset of the GFAP-reacted slides were counter-stained with Thioflavin S to localize the Aβ deposits. The GFAP-positive astrocytes were associated with Aβ plaques in the SAP, PBS and untreated controls. No such association was found in the plaque-negative Aβ1–42 treated mice, while minimal plaque-associated gliosis was identified in one mouse treated with AN1792.

Figure 4:
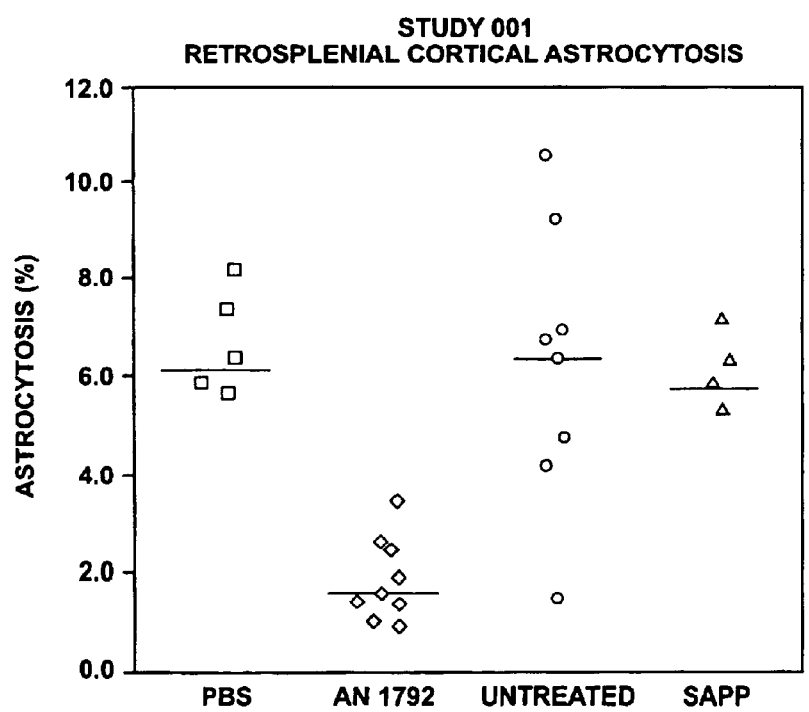
FIG. 4: Astrocytosis in the retrosplenial cortex. The percentage of the area of the cortical region occupied by glial fibrillary acidic protein (GFAP)-positive astrocytes was determined by quantitative computer-assisted image analysis of immunoreacted brain sections. The values for individual mice are shown sorted by treatment group and median group values are indicated by horizontal lines.

Image analyses, shown in FIG. 4 for the retrosplenial cortex, verified that the reduction in astrocytosis was significant with a median value of 1.56% for those treated with AN1792 versus median values greater than 6% for groups immunized with SAP peptides, PBS or untreated (p=0.0017).

Evidence from a subset of the Aβ1–42- and PBS-injected mice indicated plaque-associated MHC II immunoreactivity was absent in the Aβ1–42 injected mice, consistent with lack of an Aβ-related inflammatory response.

Sections of the mouse brains were also reacted with a mAb specific with a monoclonal antibody specific for MAC-1, a cell surface protein. MAC-1 (CD11b) is an integrin family member and exists as a heterodimer with CD18. The CD11b/CD18 complex is present on monocytes, macrophages, neutrophils and natural killer cells (Mak and Simard). The resident MAC-1-reactive cell type in the brain is likely to be microglia based on similar phenotypic morphology in MAC-1 immunoreacted sections. Plaque-associated MAC-1 labeling was lower in the brains of mice treated with AN1792 compared to the PBS control group, a finding consistent with the lack of an Aβ-induced inflammatory response.

C. Conclusion

The lack of Aβ plaques and reactive neuronal and gliotic changes in the brains of the Aβ1–42-injected mice indicate that no or extremely little amyloid was deposited in their brains, and pathological consequences, such as gliosis and neuritic pathology, were absent. PDAPP mice treated with Aβ1–42 show essentially the same lack of pathology as control nontransgenic mice. Therefore, Aβ1–42 injections are highly effective in the prevention of deposition or clearance of human Aβ from brain tissue, and elimination of subsequent neuronal and inflammatory degenerative changes. Thus, administration of Aβ peptide can have both preventative and therapeutic benefit in prevention of Aβ.

II. Dose Response Study

Groups of five-week old, female Swiss Webster mice (N=6 per group) were immunized with 300, 100, 33, 11, 3.7, 1.2, 0.4, or 0.13 ug of Aβ formulated in CFA/IFA administered intraperitoneally. Three doses were given at biweekly intervals followed by a fourth dose one month later. The first dose was emulsified with CFA and the remaining doses were emulsified with IFA. Animals were bled 4–7 days following each immunization starting after the second dose for measurement of antibody titers. Animals in a subset of three groups, those immunized with 11, 33, or 300 ug of antigen, were additionally bled at approximately monthly intervals for four months following the fourth immunization to monitor the decay of the antibody response across a range of doses of immunogenic formulations. These animals received a final fifth immunization at seven months after study initiation. They were sacrificed one week later to measure antibody responses to AN1792 and to perform toxicological analyses.

Figure 5:
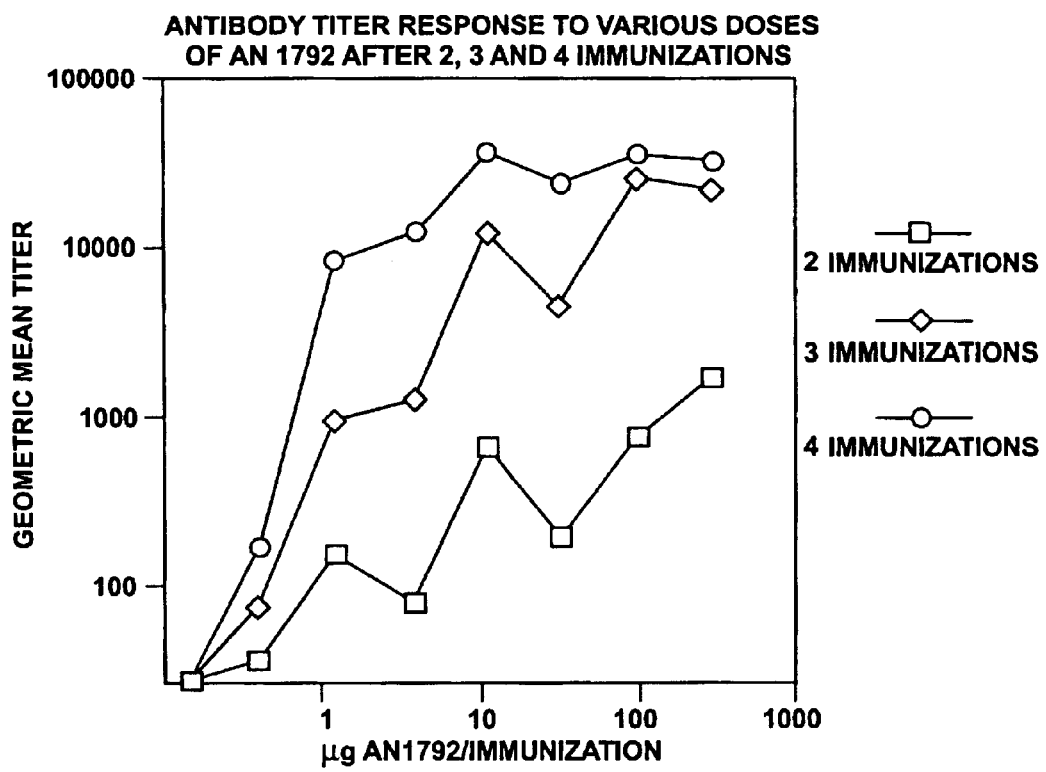
FIG. 5: Geometric mean antibody titers to Aβ1–42 following immunization with a range of eight doses of AN1792 containing 0.14, 0.4, 1.2, 3.7, 11, 33, 100, or 300 µg.

A declining dose response was observed from 300 to 3.7 μg with no response at the two lowest doses. Mean antibody titers are about 1:1000 after 3 doses and about 1:10,000 after 4 doses of 11–300 μg of antigen (see FIG. 5).

Antibody titers rose dramatically for all but the lowest dose group following the third immunization with increases in GMTs ranging from 5- to 25-fold. Low antibody responses were then detectable for even the 0.4 μg recipients. The 1.2 and 3.7 μg groups had comparable titers with GMTs of about 1000 and the highest four doses clustered together with GMTs of about 25,000, with the exception of the 33 ug dose group with a lower GMT of 3000. Following the fourth immunization, the titer increase was more modest for most groups. There was a clear dose response across the lower antigen dose groups from 0.14 μg to 11 μg ranging from no detectable antibody for recipients of 0.14 μg to a GMT of 36,000 for recipients of 11 μg. Again, titers for the four highest dose groups of 11 to 300 μg clustered together. Thus following two immunizations, the antibody titer was dependent on the antigen dose across the broad range from 0.4 to 300 μg. By the third immunization, titers of the highest four doses were all comparable and they remained at a plateau after an additional immunization.

Figure 6:
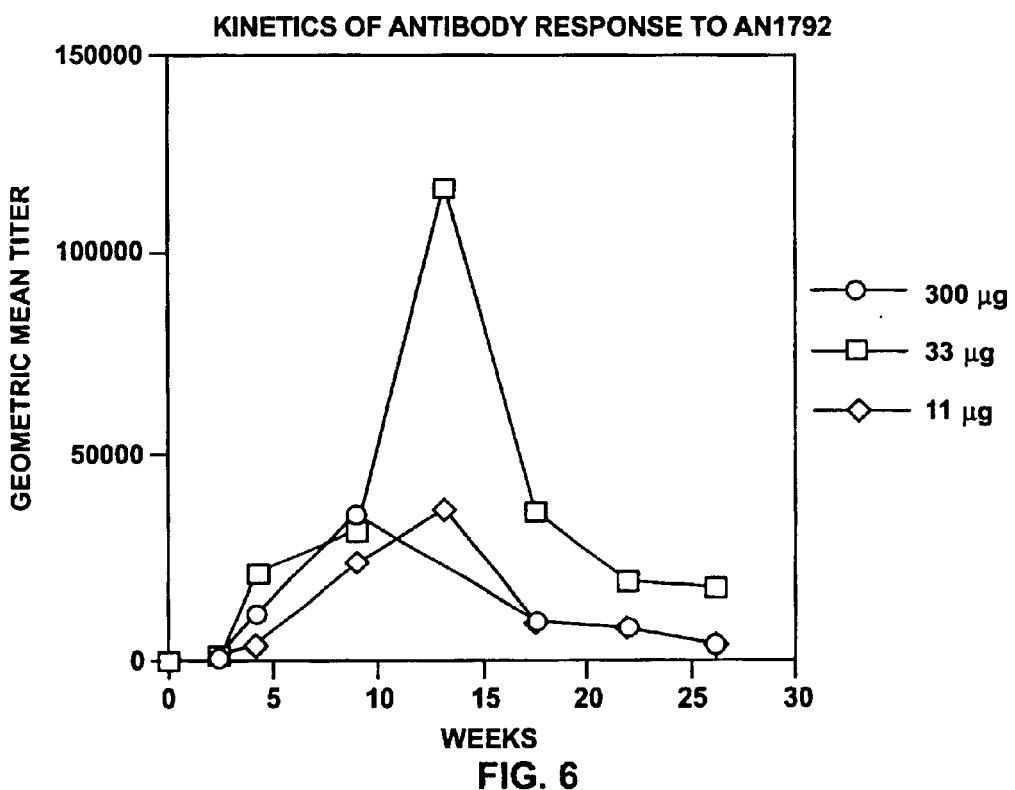
FIG. 6: Kinetics of antibody response to AN1792 immunization. Titers are expressed as geometric means of values for the 6 animals in each group.

One month following the fourth immunization, titers were 2- to 3-fold higher in the 300 μg group than those measured from blood drawn five days following the immunization (FIG. 6). This observation suggests that the peak anamnestic antibody response occurred later than 5 days post-immunization. A more modest (50%) increase was seen at this time in the 33 μg group. In the 300 μg dose group at two months following the last dose, GMTs declined steeply by about 70%. After another month, the decline was less steep at 45% (100 μg) and about 14% for the 33 and 11 μg doses. Thus, the rate of decline in circulating antibody titers following cessation of immunization appears to be biphasic with a steep decline the first month following peak response followed by a more modest rate of decrease thereafter.

The antibody titers and the kinetics of the response of these Swiss Webster mice are similar to those of young heterozygous PDAPP transgenic mice immunized in a parallel manner. Dosages effective to induce an immune response in humans are typically similar to dosages effective in mice.

III. Screen for Therapeutic Efficacy Against Established AD

This assay is designed to test immunogenic agents for activity in arresting or reversing neuropathologic characteristics of Aβ in aged animals. Immunizations with 42 amino acid long Aβ (AN1792) were begun at a time point when amyloid plaques are already present in the brains of the PDAPP mice.

Over the time course used in this study, untreated PDAPP mice develop a number of neurodegenerative changes that resemble those found in Aβ (Games et al., supra and Johnson-Wood et al., *Proc. Natl. Acad. Sci. USA* 94, 1550–1555 (1997)). The deposition of Aβ into amyloid plaques is associated with a degenerative neuronal response consisting of aberrant axonal and dendritic elements, called dystrophic neurites. Amyloid deposits that are surrounded by and contain dystrophic neurites called neuritic plaques. In both Aβ and the PDAPP mouse, dystrophic neurites have a distinctive globular structure, are immunoreactive with a panel of antibodies recognizing APP and cytoskeletal components, and display complex subcellular degenerative changes at the ultrastructural level. These characteristics allow for disease-relevant, selective and reproducible measurements of neuritic plaque formation in the PDAPP brains. The dystrophic neuronal component of PDAPP neuritic plaques is easily visualized with an antibody specific for human APP (monoclonal antibody 8E5), and is readily measurable by computer-assisted image analysis. Therefore, in addition to measuring the effects of AN1792 on amyloid plaque formation, we monitored the effects of this treatment on the development of neuritic dystrophy.

Astrocytes and microglia are non-neuronal cells that respond to and reflect the degree of neuronal injury. GFAP-positive astrocytes and MHC II-positive microglia are commonly observed in AD, and their activation increases with the severity of the disease. Therefore, we also monitored the development of reactive astrocytosis and microgliosis in the AN1792-treated mice.

A. Materials and Methods

Forty-eight, heterozygous female PDAPP mice, 11 to 11.5 months of age, obtained from Charles River, were randomly divided into two groups: 24 mice to be immunized with 100 μg of AN1792 and 24 mice to be immunized with PBS, each combined with Freund's adjuvant. The AN1792 and PBS groups were again divided when they reached ~15 months of age. At 15 months of age approximately half of each group of the AN1792- and PBS-treated animals were euthanized (n=10 and 9. respectively), the remainder continued to receive immunizations until termination at ~18 months (n=9 and 12, respectively). A total of 8 animals (5 AN1792, 3 PBS) died during the study. In addition to the immunized animals, one-year old (n=10), 15-month old (n=10) and 18-month old (n=10) untreated PDAPP mice were included for comparison in the ELISAs to measure Aβ and APP levels in the brain; the one-year old animals were also included in the immunohistochemical analyses.

Methodology was as in Example 1 unless otherwise indicated. US Peptides lot 12 and California Peptides lot ME0339 of AN1792 were used to prepare the antigen for the six immunizations administered prior to the 15-month time point. California Peptides lots ME0339 and ME0439 were used for the three additional immunizations administered between 15 and 18 months.

For immunizations, 100 μg of AN1792 in 200 μl PBS or PBS alone was emulsified 1:1 (vol:vol) with Complete Freund's adjuvant (CFA) or Incomplete Freund's adjuvant (IFA) or PBS in a final volume of 400 μl. The first immunization was delivered with CFA as adjuvant, the next four doses were given with IFA and the final four doses with PBS alone without added adjuvant. A total of nine immunizations were given over the seven-month period on a two-week schedule for the first three doses followed by a four-week interval for the remaining injections. The four-month treatment group, euthanized at 15 months of age, received only the first 6 immunizations.

B. Results

1. Effects of AN1792 Treatment on Amyloid Burden

Figure 7:
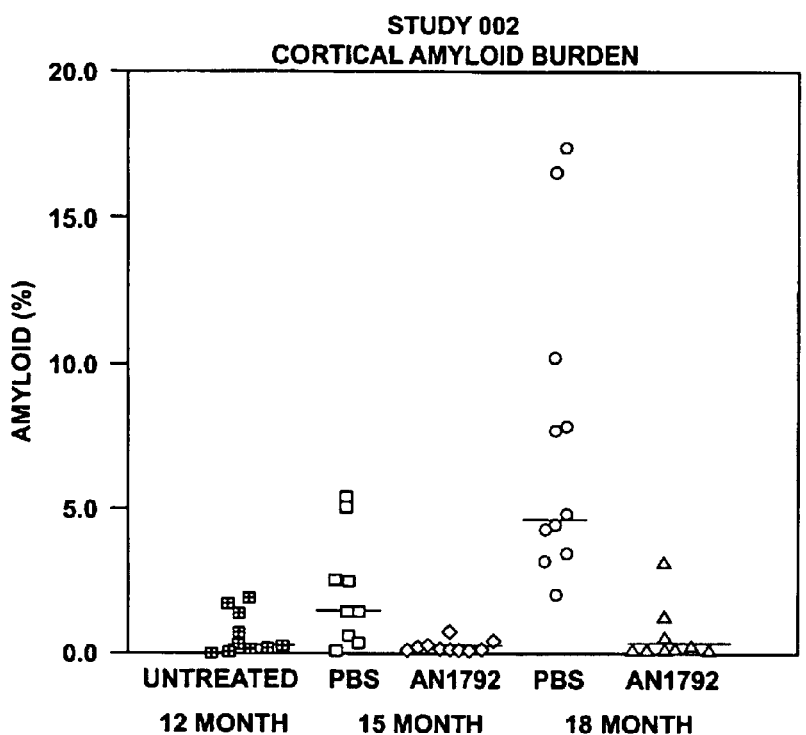
FIG. 7: Quantitative image analysis of the cortical amyloid burden in PBS- and AN1792-treated mice.

The results of AN1792 treatment on cortical amyloid burden determined by quantitative image analysis are shown in FIG. 7. The median value of cortical amyloid burden was 0.28% in a group of untreated 12-month old PDAPP mice, a value representative of the plaque load in mice at the study's initiation. At 18 months, the amyloid burden increased over 17-fold to 4.87% in PBS-treated mice, while AN1792-treated mice had a greatly reduced amyloid burden of only 0.01%, notably less than the 12-month untreated and both the 15- and 18-month PBS-treated groups. The amyloid burden was significantly reduced in the AN1792 recipients at both 15 (96% reduction; p=0.003) and 18 (>99% reduction; p=0.0002) months.

Typically, cortical amyloid deposition in PDAPP mice initiates in the frontal and retrosplenial cortices (RSC) and progresses in a ventral-lateral direction to involve the temporal and entorhinal cortices (EC). Little or no amyloid was found in the EC of 12 month-old mice, the approximate age at which AN1792 was first administered. After 4 months of AN1792 treatment, amyloid deposition was greatly diminished in the RSC, and the progressive involvement of the EC was entirely eliminated by AN1792 treatment. The latter observation showed that AN1792 completely halted the progression of amyloid that would normally invade the temporal and ventral cortices, as well as arrested or possibly reversed deposition in the RSC.

The profound effects of AN1792 treatment on developing cortical amyloid burden in the PDAPP mice are further demonstrated by the 18-month group, which had been treated for seven months. A near complete absence of cortical amyloid was found in the AN1792-treated mouse, with a total lack of diffuse plaques, as well as a reduction in compacted deposits.

2. AN1792 Treatment-associated Cellular and Morphological Changes

A population of Aβ-positive cells was found in brain regions that typically contain amyloid deposits. Remarkably, in several brains from AN1792 recipients, very few or no extracellular cortical amyloid plaques were found. Most of the Aβ immunoreactivity appeared to be contained within cells with large lobular or clumped soma. Phenotypically, these cells resembled activated microglia or monocytes. They were immunoreactive with antibodies recognizing ligands expressed by activated monocytes and microglia (MHC II and CD11b) and were occasionally associated with the wall or lumen of blood vessels. Comparison of near-adjacent sections labeled with Aβ and MHC II-specific antibodies revealed that similar patterns of these cells were recognized by both classes of antibodies. Detailed examination of the AN1792-treated brains revealed that the MHC II-positive cells were restricted to the vicinity of the limited amyloid remaining in these animals. Under the fixation conditions employed, the cells were not immunoreactive with antibodies that recognize T cell (CD3, CD3e) or B cell (CD45RA, CD45RB) ligands or leukocyte common antigen (CD45), but were reactive with an antibody recognizing leukosialin (CD43) which cross-reacts with monocytes. No such cells were found in any of the PBS-treated mice.

PDAPP mice invariably develop heavy amyloid deposition in the outer molecular layer of the hippocampal dentate gyrus. The deposition forms a distinct streak within the perforant pathway, a subregion that classically contains amyloid plaques in AD. The characteristic appearance of these deposits in PBS-treated mice resembled that previously characterized in untreated PDAPP mice. The amyloid deposition consisted of both diffuse and compacted plaques in a continuous band. In contrast, in a number of brains from AN1792-treated mice this pattern was drastically altered. The hippocampal amyloid deposition no longer contained diffuse amyloid, and the banded pattern was completely disrupted. Instead, a number of unusual punctate structures were present that are reactive with anti-Aβ antibodies, several of which appeared to be amyloid-containing cells.

MHC II-positive cells were frequently observed in the vicinity of extracellular amyloid in AN1792-treated animals. The pattern of association of Aβ-positive cells with amyloid was very similar in several brains from AN1792-treated mice. The distribution of these monocytic cells was restricted to the proximity of the deposited amyloid and was entirely absent from other brain regions devoid of Aβ plaques. Confocal microscopy of MHCII- and Aβ-labelled sections revealed that plaque material was contained within many of the monocytic cells.

Quantitative image analysis of MHC II and MAC I-labeled sections revealed a trend towards increased immunoreactivity in the RSC and hippocampus of AN1792-treated mice compared to the PBS group which reached significance with the measure of MAC 1 reactivity in hippocampus.

These results are indicative of active, cell-mediated clearance of amyloid in plaque-bearing brain regions.

3. AN1792 Effects on Aβ Levels: ELISA Determinations (a) Cortical Levels

PBS groups were compared (Table 2), representing a 72% reduction in the Aβ that would otherwise be present. Similar results were obtained when cortical levels of Aβ42 were compared, namely that the AN1792-treated group contained much less Aβ42, but in this case the differences between the AN1792 and PBS groups were significant at both 15 months ($p=0.04$) and 18 months ($p=0.0001$, Table 2).

TABLE 2

Median Aβ Levels (ng/g) in Cortex

| Age | UNTREATED | | | PBS | | | AN1792 | | |
|---|---|---|---|---|---|---|---|---|---|
| | Total | Aβ42 | (n) | Total | Aβ42 | (n) | Total | Aβ42 | (n) |
| 12 | 1,600 | 1,300 | (10) | | | | | | |
| 15 | 8,700 | 8,300 | (10) | 8,600 | 7,200 | (9) | 1,600 | 1,300* | (10) |
| 18 | 22,200 | 18,500 | (10) | 19,000 | 15,900 | (12) | 5,200** | 4,000** | (9) |

*p = 0.0412
**p = 0.0001

(b) Hippocampal Levels

In untreated PDAPP mice, median hippocampal levels of total Aβ at twelve months of age were 15,000 ng/g which increased to 51,000 ng/g at 15 months and further to 81,000 ng/g at 18 months (Table 3). Similarly, PBS immunized mice showed values of 40,000 ng/g and 65,000 ng/g at 15 months and 18 months, respectively. AN1792 immunized animals exhibited less total Aβ, specifically 25,000 ng/g and 51,000 ng/g at the respective 15-month and 18-month timepoints. The 18-month AN1792-treated group value was significantly lower than that of the PBS treated group ($p=0.0105$; Table 3). Measurement of Aβ42 gave the same pattern of results, namely that levels in the AN1792-treated group were significantly lower than in the PBS group (39,000 ng/g vs. 57,000 ng/g, respectively; $p=0.002$) at the 18-month evaluation (Table 3).

TABLE 3

Median Aβ Levels (ng/g) in Hippocampus

| Age | UNTREATED | | | PBS | | | AN1792 | | |
|---|---|---|---|---|---|---|---|---|---|
| | Total | Aβ42 | (n) | Total | Aβ42 | (n) | Total | Aβ42 | (n) |
| 12 | 15,500 | 11,100 | (10) | | | | | | |
| 15 | 51,500 | 44,400 | (10) | 40,100 | 35,70 | (9) | 24,50 | 22,100 | (10) |
| 18 | 80,000 | 64,200 | (10) | 65,400 | 57,10 | (12) | 50,90 | 38,900** | (9) |

*p = 0.0105
**p = 0.0022

In untreated PDAPP mice, the median level of total Aβ in the cortex at 12 months was 1,600 ng/g, which increased to 8,700 ng/g by 15 months (Table 2). At 18 months the value was 22,000 ng/g, an increase of over 10-fold during the time course of the experiment. PBS-treated animals had 8,600 ng/g total Aβ at 15 months which increased to 19,000 ng/g at 18 months. In contrast, AN1792-treated animals had 81% less total Aβ at 15 months (1,600 ng/g) than the PBS-immunized group. Significantly less ($p=0.0001$) total Aβ (5,200 ng/g) was found at 18 months when the AN11792 and (c) Cerebellar Levels In 12-month untreated PDAPP mice, the median cerebellar level of total Aβ was 15 ng/g (Table 4). At 15 months, this median increased to 28 ng/g and by 18 months had risen to 35 ng/g. PBS-treated animals displayed median total Aβ values of 21 ng/g at 15 months and 43 ng/g at 18 months. AN1792-treated animals were found to have 22 ng/g total Aβ at 15 months and significantly less ($p=0.002$) total Aβ at 18 months (25 ng/g) than the corresponding PBS group (Table 4).

TABLE 4

Median Aβ Levels (ng/g) in Cerebellum

| | UNTREATED | | PBS | | AN1792 | |
|---|---|---|---|---|---|---|
| Age | Total Aβ | (n) | Total Aβ | (n) | Total Aβ | (n) |
| 12 | 15.6 | (10) | | | | |
| 15 | 27.7 | (10) | 20.8 | (9) | 21.7 | (10) |
| 18 | 35.0 | (10) | 43.1 | (12) | 24.8* | (9) |

*p = 0.0018

4. Effects of AN1792 Treatment on APP Levels

APP-α and the full-length APP molecule both contain all or part of the Aβ sequence and thus could be potentially impacted by the generation of an AN1792-directed immune response. In studies to date, a slight increase in APP levels has been noted as neuropathology increases in the PDAPP mouse. In the cortex, levels of either APP-α/FL (full length) or APP-α were essentially unchanged by treatment with the exception that APP-α was reduced by 19% at the 18-month timepoint in the AN1792-treated vs. the PBS-treated group. The 18-month AN1792-treated APP values were not significantly different from values of the 12-month and 15-month untreated and 15-month PBS groups. In all cases the APP values remained within the ranges that are normally found in PDAPP mice.

5. Effects of AN1792 Treatment on Neurodegenerative and Gliotic Pathology

Figure 8:
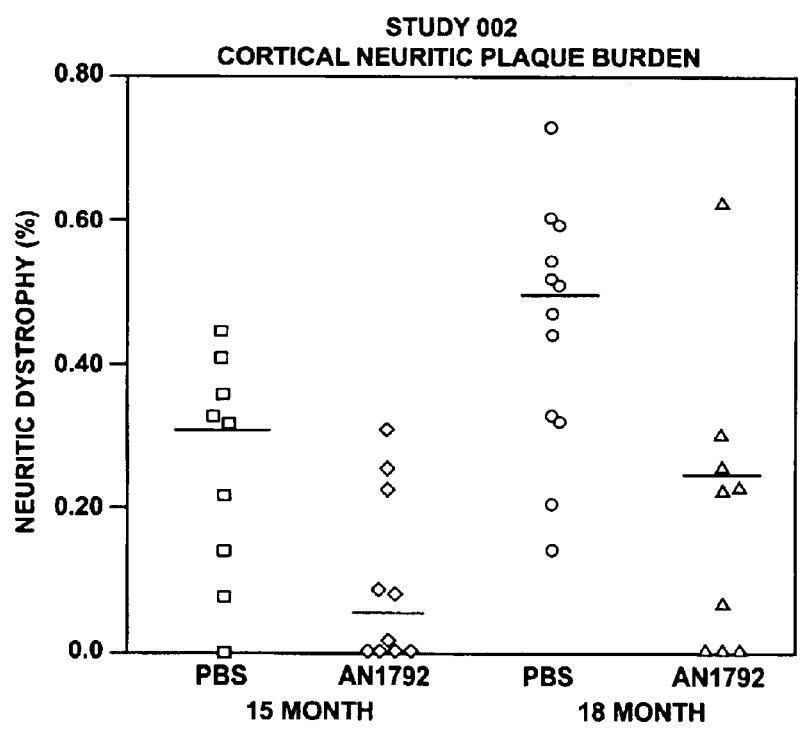
FIG. 8: Quantitative image analysis of the neuritic plaque burden in PBS- and AN1792-treated mice.

Neuritic plaque burden was significantly reduced in the frontal cortex of AN1792-treated mice compared to the PBS group at both 15 (84%; p=0.$^{03}$) and 18 (55%; p=0.01) months of age (FIG. 8). The median value of the neuritic plaque burden increased from 0.32% to 0.49% in the PBS group between 15 and 18 months of age. This contrasted with the greatly reduced development of neuritic plaques in the AN1792 group, with median neuritic plaque burden values of 0.05% and 0.22%, in the 15 and 18 month groups, respectively.

Figure 9:
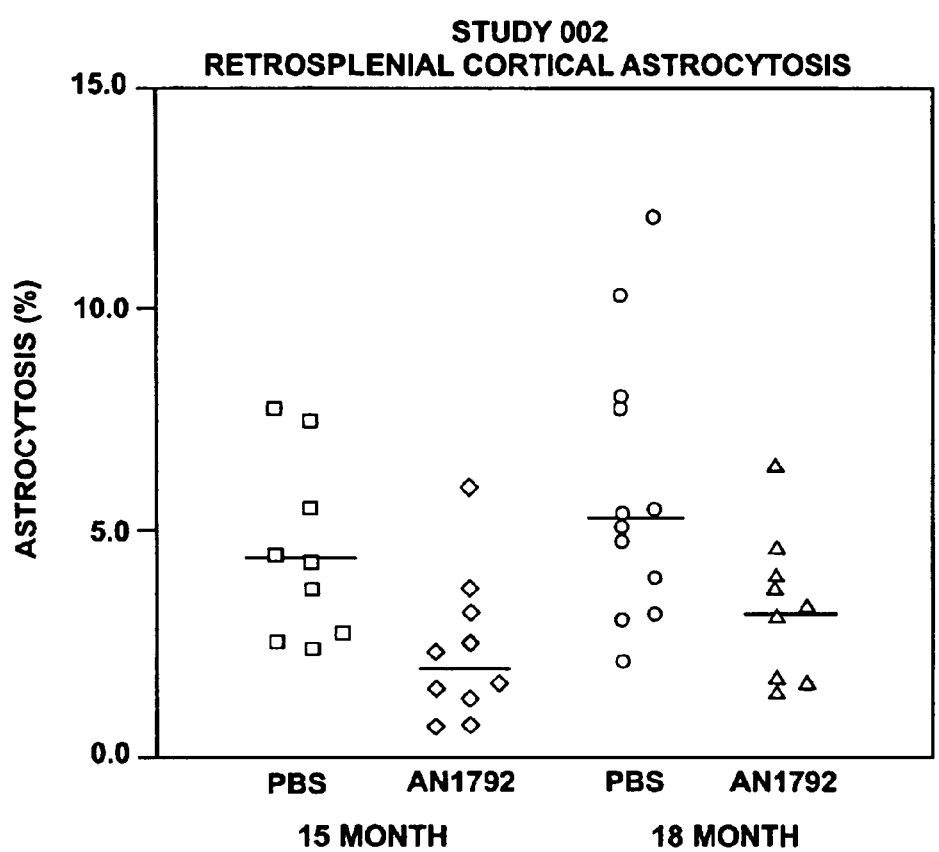
FIG. 9: Quantitative image analysis of the percent of the retrosplenial cortex occupied by astrocytosis in PBS- and AN1792-treated mice.

Immunizations with AN1792 seemed well tolerated and reactive astrocytosis was also significantly reduced in the RSC of AN1792-treated mice when compared to the PBS group at both 15 (56%; p=0.01 1) and 18 (39%; p=0.028) months of age (FIG. 9). Median values of the percent of astrocytosis in the PBS group increased between 15 and 18 months from 4.26% to 5.21%. AN1792-treatment suppressed the development of astrocytosis at both time points to 1.89% and 3.2%, respectively. This suggests the neuropil was not being damaged by the clearance process.

6. Antibody Responses

As described above, eleven-month old, heterozygous PDAPP mice (N=24) received a series of 5 immunizations of 100 μg of AN1792 emulsified with Freund's adjuvant and administered intraperitoneally at weeks 0, 2, 4, 8, and 12, and a sixth immunization with PBS alone (no Freund's adjuvant) at week 16. As a negative control, a parallel set of 24 age-matched transgenic mice received immunizations of PBS emulsified with the same adjuvants and delivered on the same schedule. Animals were bled within three to seven days following each immunization starting after the second dose. Antibody responses to AN1792 were measured by ELISA. Geometric mean titers (GMT) for the animals that were immunized with AN1792 were approximately 1,900, 7,600, and 45,000 following the second, third and last (sixth) doses respectively. No Aβ-specific antibody was measured in control animals following the sixth immunization.

Approximately one-half of the animals were treated for an additional three months, receiving immunizations at about 20, 24 and 27 weeks. Each of these doses was delivered in PBS vehicle alone without Freund's adjuvant. Mean antibody titers remained unchanged over this time period. In fact, antibody titers appeared to remain stable from the fourth to the eighth bleed corresponding to a period covering the fifth to the ninth injections.

To determine if the Aβ-specific antibodies elicited by immunization that were detected in the sera of AN1792-treated mice were also associated with deposited brain amyloid, a subset of sections from the AN1792- and PBS-treated mice were reacted with an antibody specific for mouse IgG. In contrast to the PBS group, Aβ plaques in AN1792-treated brains were coated with endogenous IgG. This difference between the two groups was seen in both 15-and 18-month groups. Particularly striking was the lack of labeling in the PBS group, despite the presence of a heavy amyloid burden in these mice. These results show that immunization with a synthetic Aβ protein generates antibodies that recognize and bind in vivo to the Aβ in amyloid plaques.

7. Cellular-Mediated Immune Responses

Figure 10A:
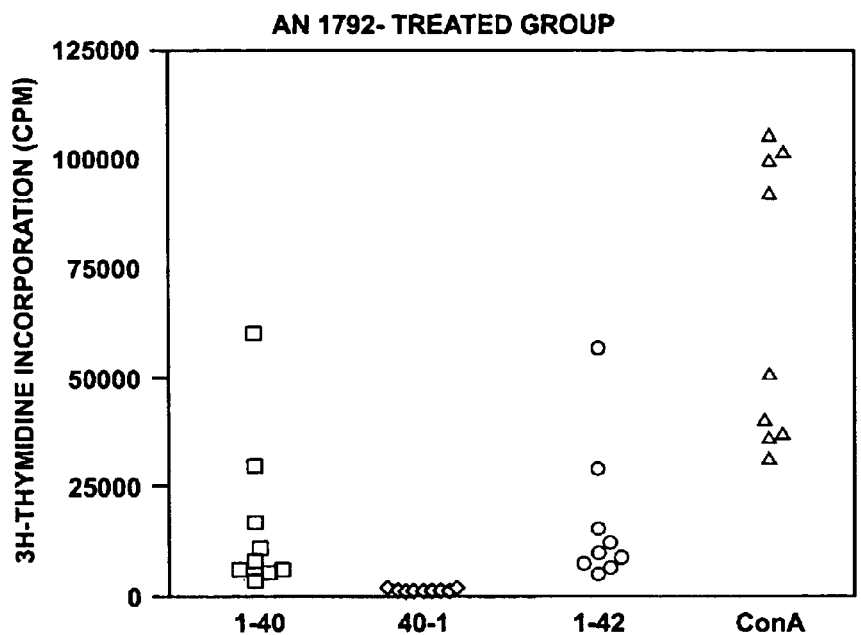
FIG. 10: Lymphocyte Proliferation Assay on spleen cells from AN1792-treated (FIG. 10A) or PBS-treated (FIG. 10B).
Figure 10B:
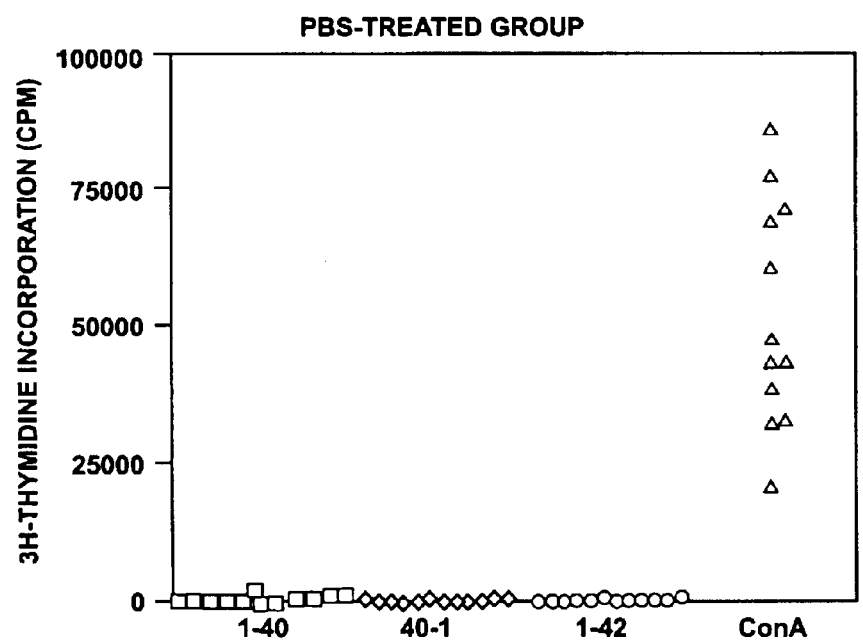

Spleens were removed from nine AN1792-immunized and 12 PBS-immunized 18-month old PDAPP mice 7 days after the ninth immunization. Splenocytes were isolated and cultured for 72 h in the presence of Aβ40, Aβ42, or Aβ40-1 (reverse order protein). The mitogen Con A served as a positive control. Optimum responses were obtained with>1.7 μM protein. Cells from all nine AN1792-treated animals proliferated in response to either Aβ1–40 or Aβ1–42 protein, with equal levels of incorporation for both proteins (FIG. 10A. There was no response to the Aβ40-1 reverse protein. Cells from control animals did not respond to any of the Aβ proteins (FIG. 10B).

C. Conclusion

The results of this study show that AN1792 immunization of PDAPP mice possessing existing amyloid deposits slows and prevents progressive amyloid deposition and retard consequential neuropathologic changes in the aged PDAPP mouse brain. Immunizations with AN1792 essentially halted amyloid developing in structures that would normally succumb to amyloidosis. Thus, administration of Aβ peptide has therapeutic benefit in the treatment of AD.

IV. Screen of Aβ Fragments

100 PDAPP mice age 9–11 months were immunized with 9 different regions of APP and, A to determine which epitopes convey the efficacious response. The 9 different immunogens and one control are injected i.p. as described above. The immunogens include four human Aβ peptide conjugates 1–12, 13–28, 32–42, 1–5, all coupled to sheep anti-mouse IgG via a cystine link; an APP polypeptide amino acids 592–695, aggregated human Aβ1–40, and aggregated human Aβ25–35, and aggregated rodent Aβ42. Aggregated Aβ42 and PBS were used as positive and negative controls, respectively. Ten mice were used per treatment group. Titers were monitored as above and mice were euthanized at the end of 4 months of injections. Histochemistry, Aβ levels, and toxicology analysis was determined post mortem.

A. Materials and Methods

1. Preparation of Immunogens

Preparation of coupled Aβ peptides: four human Aβ peptide conjugates (amino acid residues 1–5, 1–12, 13–28, and 33–42, each conjugated to sheep anti-mouse IgG) were prepared by coupling through an artificial cysteine added to the Aβ peptide using the crosslinking reagent sulfo-EMCS. The Aβ peptide derivatives were synthesized with the following final amino acid sequences. In each case, the location of the inserted cysteine residue is indicated by underlining. The Aβ13–28 peptide derivative also had two glycine residues added prior to the carboxyl terminal cysteine as indicated.

| | |
|---|---|
| Aβ1-12 peptide | NH2-DAEFRHDSGYEV<u>C</u>-COOH (SEQ ID NO:72) |
| Aβ1-5 peptide | NH2-DAEFR<u>C</u>-COOH (SEQ ID NO:73) |
| Aβ33-42 peptide | NH2-<u>C</u>-amino-heptanoic acid-GLMVGGVVIA-COOH (SEQ ID NO:74) |
| Aβ13-28 peptide | Ac-NH-HHQKLVFFAEDVGSNKGG<u>C</u>-COOH (SEQ ID NO:75) |

To prepare for the coupling reaction, ten mg of sheep anti-mouse IgG (Jackson ImmunoResearch Laboratories) was dialyzed overnight against 10 mM sodium borate buffer, pH 8.5. The dialyzed antibody was then concentrated to a volume of 2 mL using an Amicon Centriprep tube. Ten mg sulfo-EMCS [N (ε-maleimidocuproyloxy) succinimide] (Molecular Sciences Co.) was dissolved in one mL deionized water. A 40-fold molar excess of sulfo-EMCS was added dropwise with stirring to the sheep anti-mouse IgG and then the solution was stirred for an additional ten min. The activated sheep anti-mouse IgG was purified and buffer exchanged by passage over a 10 mL gel filtration column (Pierce Presto Column, obtained from Pierce Chemicals) equilibrated with 0.1 M NaPO4, 5 mM EDTA, pH 6.5. Antibody containing fractions, identified by absorbance at 280 nm, were pooled and diluted to a concentration of approximately 1 mg/mL, using 1.4 mg per OD as the extinction coefficient. A 40-fold molar excess of Aβ peptide was dissolved in 20 mL of 10 mM NaPO4, pH 8.0, with the exception of the Aβ33–42 peptide for which 10 mg was first dissolved in 0.5 mL of DMSO and then diluted to 20 mL with the 10 mM NaPO4 If buffer. The peptide solutions were each added to 10 mL of activated sheep anti-mouse IgG and rocked at room temperature for 4 hr. The resulting conjugates were concentrated to a final volume of less than 10 mL using an Amicon Centriprep tube and then dialyzed against PBS to buffer exchange the buffer and remove free peptide. The conjugates were passed through 0.22 μm-pore size filters for sterilization and then aliquoted into fractions of 1 mg and stored frozen at −20° C. The concentrations of the conjugates were determined using the BCA protein assay (Pierce Chemicals) with horse IgG for the standard curve. Conjugation was documented by the molecular weight increase of the conjugated peptides relative to that of the activated sheep anti-mouse IgG. The Aβ1–5 sheep anti-mouse conjugate was a pool of two conjugations, the rest were from a single preparation. 2. Preparation of aggregated Aβ peptides Human 1–40 (AN1528; California Peptides Inc., Lot ME0541), human 1–42 (AN1792; California Peptides Inc., Lots ME0339 and ME0439), human 25–35, and rodent 1j42 (California Peptides Inc., Lot ME0218) peptides were freshly solubilized for the preparation of each set of injections from lyophilized powders that had been stored desiccated at −20° C. For this purpose, two mg of peptide were added to 0.9 ml of deionized water and the mixture was vortexed to generate a relatively uniform solution or suspension. Of the four, AN1528 was the only peptide soluble at this step. A 100 μl aliquot of 10×PBS (1×PBS: 0.15 M NaCl, 0.01 M sodium phosphate, pH 7.5) was then added at which point AN1528 began to precipitate. The suspension was vortexed again and incubated overnight at 37° C. for use the next day.

Preparation of the pBx6 protein: An expression plasmid encoding pBx6, a fusion protein consisting of the 100-amino acid bacteriophage MS-2 polymerase N-terminal leader sequence followed by amino acids 592–695 of APP (βAPP) was constructed as described by Oltersdorf et al., J. Biol. Chem. 265, 4492–4497 (1990). The plasmid was transfected into E. coli and the protein was expressed after induction of the promoter. The bacteria were lysed in 8M urea and pBx6 was partially purified by preparative SDS PAGE. Fractions containing pBx6 were identified by Western blot using a rabbit anti-pBx6 polyclonal antibody, pooled, concentrated using an Amicon Centriprep tube and dialysed against PBS. The purity of the preparation, estimated by Coomassie Blue stained SDS PAGE, was approximately 5 to 10%.

B. Results and Discussion

1. Study Design

One hundred male and female, nine- to eleven-month old heterozygous PDAPP transgenic mice were obtained from Charles River Laboratory and Taconic Laboratory. The mice were sorted into ten groups to be immunized with different regions of Aβ or APP combined with Freund's adjuvant. Animals were distributed to match the gender, age, parentage and source of the animals within the groups as closely as possible. The immunogens included four Aβ peptides derived from the human sequence, 1–5, 1–12, 13–28, and 33–42, each conjugated to sheep anti-mouse IgG; four aggregated Aβ peptides, human 1–40 (AN1528), human 142 (AN1792), human 25–35, and rodent 1–42; and a fusion polypeptide, designated as pBx6, containing APP amino acid residues 592–695. A tenth group was immunized with PBS combined with adjuvant as a control.

For each immunization, 100 μg of each Aβ peptide in 200 μl PBS or 200 μg of the APP derivative pBx6 in the same volume of PBS or PBS alone was emulsified 1:1 (vol:vol) with Complete Freund's adjuvant (CFA) in a final volume of 400 μl for the first immunization, followed by a boost of the same amount of immunogen in Incomplete Freund's adjuvant (IFA) for the subsequent four doses and with PBS for the final dose. Immunizations were delivered intraperitoneally on a biweekly schedule for the first three doses, then on a monthly schedule thereafter. Animals were bled four to seven days following each immunization starting after the second dose for the measurement of antibody titers. Animals were euthanized approximately one week after the final dose.

2. Aβ and APP Levels in the Brain

Following about four months of immunization with the various Aβ peptides or the APP derivative, brains were removed from saline-perfused animals. One hemisphere was prepared for immunohistochemical analysis and the second was used for the quantitation of Aβ and APP levels. To measure the concentrations of various forms of beta amyloid peptide and amyloid precursor protein, the hemisphere was dissected and homogenates of the hippocampal, cortical, and cerebellar regions were prepared in 5 M guanidine. These were diluted and the level of amyloid or APP was quantitated by comparison to a series of dilutions of standards of Aβ peptide or APP of known concentrations in an ELISA format.

The median concentration of total Aβ for the control group immunized with PBS was 5.8-fold higher in the hippocampus than in the cortex (median of 24,318 ng/g hippocampal tissue compared to 4,221 ng/g for the cortex). The median level in the cerebellum of the control group (23.4 ng/g tissue) was about 1,000-fold lower than in the hippocampus. These levels are similar to those that we have previously reported for heterozygous PDAPP transgenic mice of this age (Johnson-Woods et al., 1997, supra).

Figure 11:
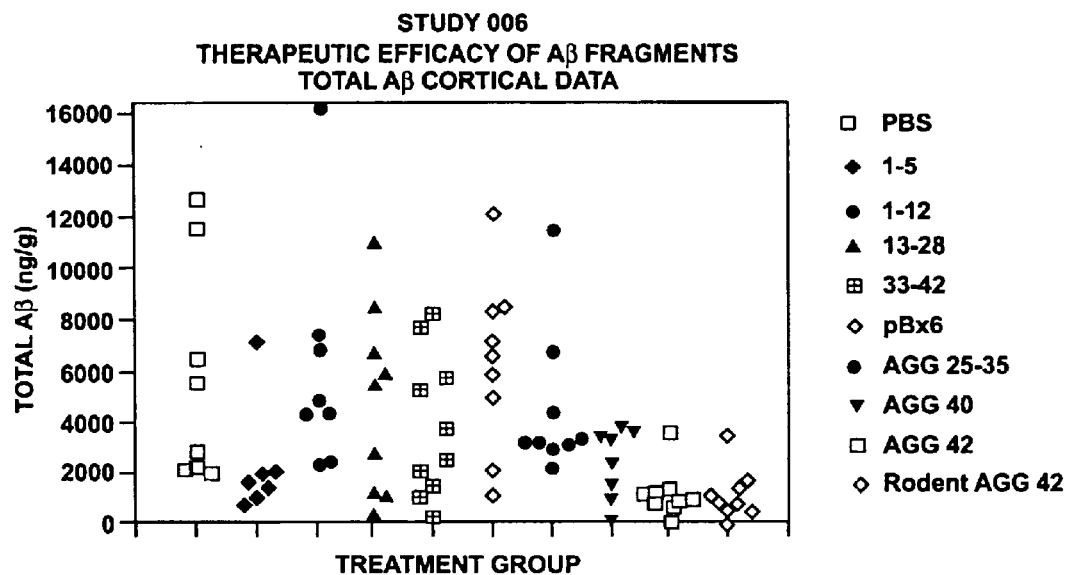
FIG. 11: Total Aβ levels in the cortex. A scatterplot of individual Aβ profiles in mice immunized with Aβ or APP derivatives combined with Freund' adjuvant.

For the cortex, a subset of treatment groups had median total Aβ and A—1–42 levels which differed significantly from those of the control group (p<0.05), those animals receiving AN1792, rodent Aβ1–42 or the Aβ1–5 peptide conjugate as shown in FIG. 11. The median levels of total Aβ were reduced by 75%, 79% and 61%, respectively, compared to the control for these treatment groups. There were no discernable correlations between Aβ-specific antibody titers and Aβ levels in the cortical region of the brain for any of the groups.

In the hippocampus, the median reduction of total Aβ associated with AN1792 treatment (46%, p=0.0543) was not as great as that observed in the cortex (75%, p=0.0021). However, the magnitude of the reduction was far greater in the hippocampus than in the cortex, a net reduction of 11,186 ng/g tissue in the hippocampus versus 3,171 ng/g tissue in the cortex. For groups of animals receiving rodent Aβ42 or Aβ1–5, the median total Aβ levels were reduced by 36% and 26%, respectively. However, given the small group sizes and the high variability of the amyloid peptide levels from animal to animal within both groups, these reductions were not significant. When the levels of Aβ142 were measured in the hippocampus, none of the treatment-induced reductions reached significance. Thus, due to the smaller Aβ burden in the cortex, changes in this region are a more sensitive indicator of treatment effects. The changes in Aβ levels measured by ELISA in the cortex are similar, but not identical, to the results from the immunohistochemical analysis (see below).

Total Aβ was also measured in the cerebellum, a region typically minimally affected with Aβ pathology. None of the median Aβ concentrations of any of the groups immunized with the various Aβ peptides or the APP derivative differed from that of the control group in this region of the brain. This result suggests that non-pathological levels of Aβ are unaffected by treatment.

APP concentration was also determined by ELISA in the cortex and cerebellum from treated and control mice. Two different APP assays were utilized. The first, designated APP-α/FL, recognizes both APP-alpha (α, the secreted form of APP which has been cleaved within the Aβ sequence), and full-length forms (FL) of APP, while the second recognizes only APP-α. In contrast to the treatment-associated diminution of Aβ in a subset of treatment groups, the levels of APP were unchanged in all of the treated compared to the control animals. These results indicate that the immunizations with Aβ peptides are not depleting APP; rather the treatment effect is specific to Aβ.

In summary, total Aβ and Aβ1–42 levels were significantly reduced in the cortex by treatment with AN1792, rodent Aβ1–42 or Aβ1–5 conjugate. In the hippocampus, total Aβ was significantly reduced only by AN1792 treatment. No other treatment-associated changes in Aβ or APP levels in the hippocampal, cortical or cerebellar regions were significant.

2. Histochemical Analyses

Figure 12:
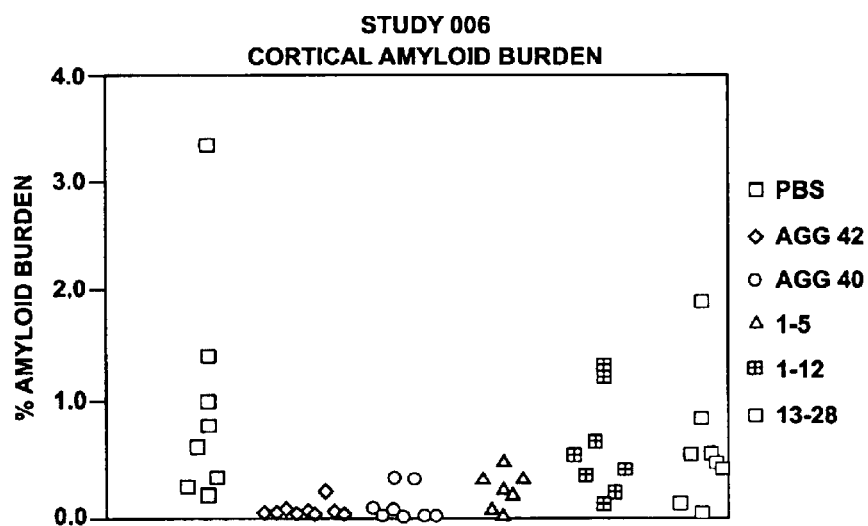
FIG. 12: Amyloid burden in the cortex was determined by quantitative image analysis of immunoreacted brain sections for mice immunized with the Aβ peptide conjugates Aβ1–5, Aβ1–12, and Aβ13–28; the full length Aβ aggregates AN1792 (Aβ1–42) and AN1528 (Aβ1–40) and the PBS-treated control group.

Brains from a subset of six groups were prepared for immunohistochemical analysis, three groups immunized with the Aβ peptide conjugates Aβ1–5, Aβ1–12, and Aβ13–28; two groups immunized with the full length Aβ aggregates AN1792 and AN15228and the PBS-treated control group. The results of image analyses of the amyloid burden in brain sections from these groups are shown in FIG. 12. There were significant reductions of amyloid burden in the cortical regions of three of the treatment groups versus control animals. The greatest reduction of amyloid burden was observed in the group receiving AN1792 where the mean value was reduced by 97% (p=0.001). Significant reductions were also observed for those animals treated with AN1528 (95%, p=0.005) and the Aβ1–5 peptide conjugate (67%, p=0.02).

The results obtained by quantitation of total Aβ or Aβ1–42 by ELISA and amyloid burden by image analysis differ to some extent. Treatment with AN1528 had a significant impact on the level of cortical amyloid burden when measured by quantitative image analysis but not on the concentration of total Aβ in the same region when measured by ELISA. The difference between these two results is likely to be due to the specificities of the assays. Image analysis measures only insoluble Aβ aggregated into plaques. In contrast, the ELISA measures all forms of Aβ, both soluble and insoluble, monomeric and aggregated. Since the disease pathology is thought to be associated with the insoluble plaque-associated form of Aβ, the image analysis technique may have more sensitivity to reveal treatment effects. However since the ELISA is a more rapid and easier assay, it is very useful for screening purposes. Moreover it may reveal that the treatment-associated reduction of Aβ is greater for plaque-associated than total Aβ.

To determine if the Aβ-specific antibodies elicited by immunization in the treated animals reacted with deposited brain amyloid, a subset of the sections from the treated animals and the control mice were reacted with an antibody specific for mouse IgG. In contrast to the PBS group, Aβ-containing plaques were coated with endogenous IgG for animals immunized with the Aβ peptide conjugates Aβ1–5, Aβ1–12, and Aβ13–28; and the full length Aβ aggregates AN1792 and AN1528. Brains from animals immunized with the other Aβ peptides or the APP peptide pBx6 were not analyzed by this assay.

3. Measurement of Antibody Titers

Figure 13:
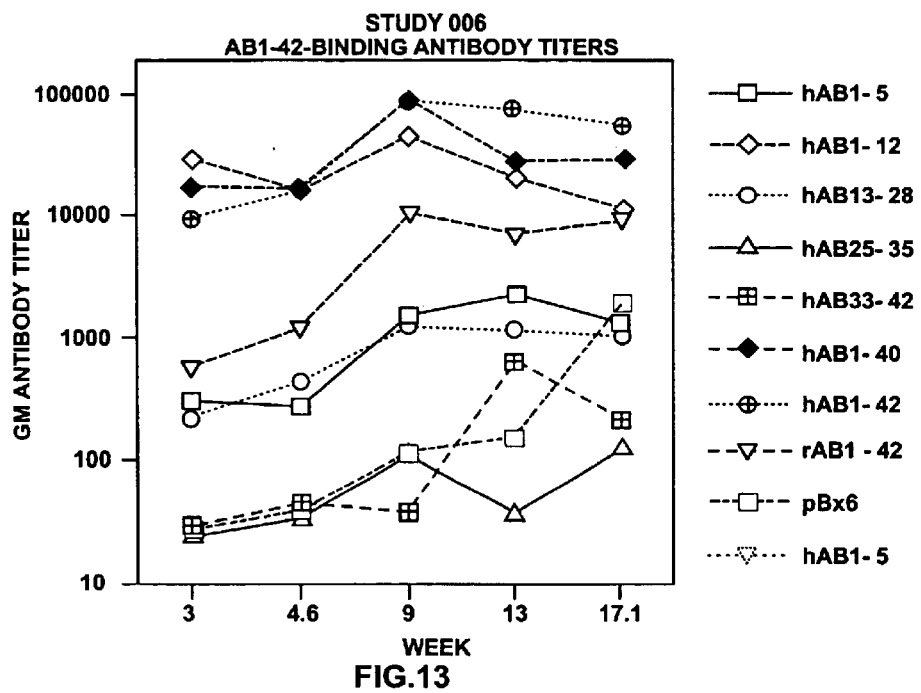
FIG. 13: Geometric mean titers of Aβ-specific antibody for groups of mice immunized with Aβ or APP derivatives combined with Freund's adjuvant.

Mice were bled four to seven days following each immunization starting after the second immunization, for a total of five bleeds. Antibody titers were measured as Aβ1–42-binding antibody using a sandwich ELISA with plastic multi-well plates coated with Aβ1–42. As shown in FIG. 13, peak antibody titers were elicited following the fourth dose for those four immunogenic formulations which elicited the highest titers of AN1792-specific antibodies: AN1792 (peak GMT: 94,647), AN1528 (peak GMT: 88,231), Aβ1–12 conjugate (peak GMT: 47,216)and rodent Apt-42 (peak GMT: 10,766). Titers for these groups declined somewhat following the fifth and sixth doses. For the remaining five immunogens, peak titers were reached following the fifth or the sixth dose and these were of much lower magnitude than those of the four highest titer groups: Aβ1–5 conjugate (peak GMT: 2,356), pBx6 (peak GMT: 1,986), Aβ13–28 conjugate (peak GMT: 1,183), Aβ3342 conjugate (peak GMT: 658), Aβ25–35 (peak GMT: 125). Antibody titers were also measured against the homologous peptides using the same ELISA sandwich format for a subset of the immunogens, those groups immunized with Aβ1–5, Aβ13–28, Aβ25–35, Aβ33–42 or rodent Aβ1–42. These titers were about the same as those measured against Aβ1–42 except for the rodent Aβ1–42 immunogen in which case antibody titers against the homologous immnunogen were about two-fold higher. The magnitude of the AN1792-specific antibody titer of individual animals or the mean values of treatment groups did not correlate with efficacy measured as the reduction of Aβ in the cortex.

4. Lymphoproliferative Responses

Aβ-dependent lymphoproliferation was measured using spleen cells harvested approximately one week following the final, sixth, immunization. Freshly harvested cells, 105 per well, were cultured for 5 days in the presence of Aβ1–40 at a concentration of 5 μM for stimulation. Cells from a subset of seven of the ten groups were also cultured in the presence of the reverse peptide, Aβ40–1. As a positive control, additional cells were cultured with the T cell mitogen, PHA, and, as a negative control, cells were cultured without added peptide.

Lymphocytes from a majority of the animals proliferated in response to PHA. There were no significant responses to the Aβ40–1 reverse peptide. Cells from animals immunized with the larger aggregated Aβ peptides, AN1792, rodent Aβ1–42 and AN1528 proliferated robustly when stimulated with Aβ1–40 with the highest cpm in the recipients of AN1792. One animal in each of the groups immunized with Aβ1–12 conjugate, Aβ13–28 conjugate and Aβ25–35 proliferated in response to Aβ1–40. The remaining groups receiving Aβ1–5 conjugate, Aβ33–42 conjugate pBx6 or PBS had no animals with an Aβ-stimulated response. These results are summarized in Table 5 below.

TABLE 5

| Immunogen | Conjugate | Aβ Amino Acids | Responders |
|---|---|---|---|
| Aβ1-5 | Yes | 5-mer | 0/7 |
| Aβ1-12 | Yes | 12-mer | 1/8 |
| Aβ13-28 | Yes | 16-mer | 1/9 |
| Aβ25-35 | | 11-mer | 1/9 |
| Aβ33-42 | Yes | 10-mer | 0/10 |
| Aβ1-40 | | 40-mer | 5/8 |
| Aβ1-42 | | 42-mer | 9/9 |
| r Aβ1-42 | | 42-mer | 8/8 |
| pBx6 | | | 0/8 |
| PBS | | 0-mer | 0/8 |

These results show that AN1792 and AN1528 stimulate strong T cell responses, most likely of the CD4+phenotype. The absence of an Aβ-specific T cell response in animals immunized with Aβ1–5 is not surprising since peptide epitopes recognized by CD4+T cells are usually about 15 amino acids in length, although shorter peptides can sometimes function with less efficiency. Thus the majority of helper T cell epitopes for the four conjugate peptides are likely to reside in the IgG conjugate partner, not in the Aβ region. This hypothesis is supported by the very low incidence of proliferative responses for animals in each of these treatment groups. Since the Aβ1-5 conjugate was effective at significantly reducing the level of Aβ in the brain, in the apparent absence of Aβ-specific T cells, the key effector immune response induced by immunization with this peptide appears to be antibody.

Lack of T-cell and low antibody response from fusion peptide pBx6, encompassing APP amino acids 592–695 including all of the Aβ residues may be due to the poor immunogenicity of this particular preparation. The poor immunogenicity of the Aβ25–35 aggregate is likely due to the peptide being too small to be likely to contain a good T cell epitope to help the induction of an antibody response. If this peptide were conjugated to a carrier protein, it would probably be more immunogenic.

V. Preparation of Polyclonal Antibodies for Passive Protection 125 non-transgenic mice were immunized with 100 μg Aβ1–42, plus CFA/IFA adjuvant, and euthanized at 4–5 months. Blood was collected from immunized mice. IgG was separated from other blood components. Antibody specific for the immunogen may be partially purified by affinity chromatography. An average of about 0.5–1 mg of immunogen-specific antibody is obtained per mouse, giving a total of 60–120 mg.

VI. Passive Immunization with Antibodies to Aβ

Groups of 7–9 month old PDAPP mice each are injected with 0.5 mg in PBS of polyclonal anti-Aβ or specific anti-β monoclonals as shown below. The cell line designated RB44-10D5.19.21 producing the antibody 10D5 has the ATCC accession number PTA-5129, having been deposited on Apr. 8. 2003. All antibody preparations are purified to have low endotoxin levels. Monoclonals can be prepared against a fragment by injecting the fragment or longer form of Aβ into a mouse, preparing hybridomas and screening the hybridomas for an antibody that specifically binds to a desired fragment of Aβ without binding to other nonoverlapping fragments of Aβ.

TABLE 6

| Antibody | Epitope |
|---|---|
| 2H3 | Aβ1-12 |
| 10D5 | Aβ1-12 |
| 266 | Aβ13-28 |
| 21F12 | Aβ33-42 |
| Mouse polyclonal anti-human Aβ42 | Anti-Aggregated Aβ42 |

Mice were injected ip as needed over a 4 month period to maintain a circulating antibody concentration measured by ELISA titer of greater than 1/1000 defined by ELISA to Aβ42 or other immunogen. Titers were monitored as above and mice were euthanized at the end of 6 months of injections. Histochemistry, Aβ levels and toxicology were performed post mortem. Ten mice were used per group. Additional studies of passive immunization are described in Examples XI and XII below.

VII. Comparison of Different Adjuvants

This example compares CFA, alum, an oil-in water emulsion and MPL for capacity to stimulate an immune response.
A. Materials and Methods
  1. Study Design One hundred female Hartley strain six-week old guinea pigs, obtained from Elm Hill, were sorted into ten groups to be immunized with AN1792 or a palmitoylated derivative thereof combined with various adjuvants. Seven groups received injections of AN1792 (33 μg unless otherwise specified) combined with a) PBS, b) Freund's adjuvant, c) MPL, d) squalene, e) MPL/squalene f) low dose alum, or g) high dose alum (300 μg AN1792). Two groups received injections of a palmitoylated derivative of AN1792 (33 μg) combined with a) PBS or b) squalene. A final, tenth group received PBS alone without antigen or additional adjuvant. For the group receiving Freund's adjuvant, the first dose was emulsified with CFA and the remaining four doses with IFA. Antigen was administered at a dose of 33 μg for all groups except the high dose alum group, which received 300 μg of AN1792. Injections were administered intraperitoneally for CFA/IFA and intramuscularly in the hind limb quadriceps alternately on the right and left side for all other groups. The first three doses were given on a biweekly schedule followed by two doses at a monthly interval). Blood was drawn six to seven days following each immunization, starting after the second dose, for measurement of antibody titers.

2. Preparation of Immunogens

Two mg Aβ42 (California Peptide, Lot ME0339) was added to 0.9 ml of deionized water and the mixture was vortexed to generate a relatively uniform suspension. A 100 μl aliquot of 10×PBS (1×PBS, 0.15 M NaCl, 0.01 M sodium phosphate, pH 7.5) was added. The suspension was vortexed again and incubated overnight at 37° C. for use the next day. Unused Aβ142 was stored with desiccant as a lyophilized powder at −20° C.

A palmitoylated derivative of AN1792 was prepared by coupling palmitic anhydride, dissolved in dimethyl formamide, to the amino terminal residue of AN1792 prior to removal of the nascent peptide from the resin by treatment with hydrofluoric acid.

To prepare formulation doses with Complete Freund's adjuvant (CFA) (group 2), 33 μg of AN1792 in 200 μl PBS was emulsified 1:1 (vol:vol) with CFA in a final volume of 400 μl for the first immunization. For subsequent immunizations, the antigen was similarly emulsified with Incomplete Freund's adjuvant (IFA).

To prepare formulation doses with MPL for groups 5 and 8, lyophilized powder (Ribi ImmunoChem Research, Inc., Hamilton, Mont.) was added to 0.2% aqueous triethylamine to a final concentration of 1 mg/ml and vortexed. The mixture was heated to 65 to 70° C. for 30 sec to create a slightly opaque uniform suspension of micelles. The solution was freshly prepared for each set of injections. For each injection in group 5, 33 μg of AN1792 in 16.5 μl PBS, 50 μg of MPL (50 μl) and 162 μl of PBS were mixed in a borosilicate tube immediately before use.

To prepare formulation doses with the low oil-in-water emulsion, AN1792 in PBS was added to 5% squalene, 0.5% Tween 80, 0.5% Span 85 in PBS to reach a final single dose concentration of 33 μg AN1792 in 250 pi (group 6). The mixture was emulsified by passing through a two-chambered hand-held device 15 to 20 times until the emulsion droplets appeared to be about equal in diameter to a 1.0 μm diameter standard latex bead when viewed under a microscope. The resulting suspension was opalescent, milky white. The emulsions were freshly prepared for each series of injections. For group 8, MPL in 0.2% triethylamine was added at a concentration of 50 μg per dose to the squalene and detergent mixture for emulsification as noted above. For the palmitoyl derivative (group 7), 33 μg per dose of palmitoyl-NH-Aβ1–42 was added to squalene and vortexed. Tween 80 and Span 85 were then added with vortexing. This mixture was added to PBS to reach final concentrations of 5% squalene, 0.5% Tween 80, 0.5% Span 85 and the mixture was emulsified as noted above.

To prepare formulation doses with alum (groups 9 and 10), AN1792 in PBS was added to Alhydrogel (aluminum hydroxide gel, Accurate, Westbury, N.Y.) to reach concentrations of 33 μg (low dose, group 9) or 300 μg (high dose, group 10). AN1792 per 5 mg of alum in a final dose volume of 250 μl. The suspension was gently mixed for 4 hr at RT.

3. Measurement of Antibody Titers

Guinea pigs were bled six to seven days following immunization starting after the second immunization for a total of four bleeds. Antibody titers against Aβ42 were measured by ELISA as described in General Materials and Methods.

4. Tissue Preparation

After about 14 weeks, all guinea pigs were euthanized by administering C02. Cerebrospinal fluid was collected and the brains were removed and three brain regions (hippocampus, cortex and cerebellum) were dissected and used to measure the concentration of total Aβ protein using ELISA.

B. Results

1. Antibody Responses

Figure 14:
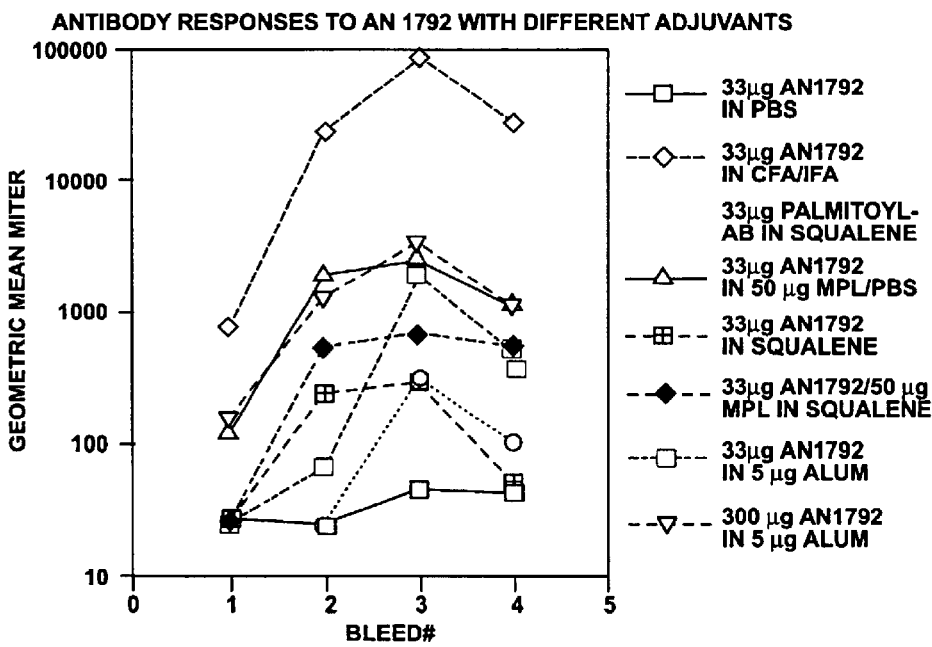
FIG. 14: Geometric mean titers of Aβ-specific antibody for groups of guinea pigs immunized with AN1792, or a palmitoylated derivative thereof, combined with various adjuvants.

There was a wide range in the potency of the various adjuvants when measured as the antibody response to AN1792 following immunization. As shown in FIG. 14, when AN1792 was administered in PBS, no antibody was detected following two or three immunizations and negligible responses were detected following the fourth and fifth doses with geometric mean titers (GMTs) of only about 45. The o/w emulsion induced modest titers following the third dose (GMT 255) that were maintained following the fourth dose (GMT 301) and fell with the final dose (GMT 54). There was a clear antigen dose response for AN1792 bound to alum with 300 μg being more immunogenic at all time points than 33 μg. At the peak of the antibody response, following the fourth immunization, the difference between the two doses was 43% with GMTs of about 1940 (33 μg) and 3400 (300 μg). The antibody response to 33 μg AN1792 plus MPL was very similar to that generated with almost a ten-fold higher dose of antigen (300 μg) bound to alum. The addition of MPL to an o/w emulsion decreased the potency of the formulations relative to that with MPL as the sole adjuvant by as much as 75%. A palmitoylated derivative of AN1792 was completely non-immunogenic when administered in PBS and gave modest titers when presented in an o/w emulsion with GMTs of 340 and 105 for the third and fourth bleeds. The highest antibody titers were generated with Freund's adjuvant with a peak GMT of about 87,000, a value almost 30-fold greater than the GMTs of the next two most potent formulations, MPL and high dose AN1792/alum.

The most promising adjuvants identified in this study are MPL and alum. Of these two, MPL appears preferable because a 10-fold lower antigen dose was required to generate the same antibody response as obtained with alum. The response can be increased by increasing the dose of antigen and /or adjuvant and by optimizing the immunization schedule. The o/w emulsion was a very weak adjuvant for AN1792 and adding an o/w emulsion to MPL adjuvant diminished the intrinsic adjuvant activity of MPL alone.

2. Aβ Levels In The Brain

At about 14 weeks the guinea pigs were deeply anesthetized, the cerebrospinal fluid (CSF) was drawn and brains were excised from animals in a subset of the groups, those immunized with Freund's adjuvant (group 2), MPL (group 5), alum with a high dose, 300 μg, of AN1792 (group 10) and the PBS immunized control group (group 3). To measure the level of Aβ peptide, one hemisphere was dissected and homogenates of the hippocampal, cortical, and cerebellar regions were prepared in 5 M guanidine. These were diluted and quantitated by comparison to a series of dilutions of Aβ standard protein of known concentrations in an ELISA format. The levels of Aβ protein in the hippocampus, the cortex and the cerebellum were very similar for all four groups despite the wide range of antibody responses to Aβ elicited by these formulations. Mean Aβ levels of about 25 ng/g tissue were measured in the hippocampus, 21 ng/g in the cortex, and 12 ng/g in the cerebellum. Thus, the presence of a high circulating antibody titer to Aβ for almost three months in some of these animals did not alter the total Aβ levels in their brains. The levels of Aβ in the CSF were also quite similar between the groups. The lack of large effect of AN1792 immunization on endogenous Aβ indicates that the immune response is focused on pathological formations of Aβ.

VIII. Immune Response to Different Adjuvants in Mice

Six-week old female Swiss Webster mice were used for this study with 10–13 animals per group. Immunizations were given on days 0, 14, 28, 60, 90 and 20 administered subcutaneously in a dose volume of 200 μl. PBS was used as the buffer for all formulations. Animals were bleed seven days following each immunization starting after the second dose for analysis of antibody titers by ELISA. The treatment regime of each group is summarized in Table 7.

TABLE 7

Experimental Design

| Group | N[a] | Adjuvant[b] | Dose | Antigen | Dose (μg) |
|---|---|---|---|---|---|
| 1 | 10 | MPL | 12.5 μg | AN1792 | 33 |
| 2 | 10 | MPL | 25 μg | AN1792 | 33 |
| 3 | 10 | MPL | 50 μg | AN1792 | 33 |
| 4 | 13 | MPL | 125 μg | AN1792 | 33 |
| 5 | 13 | MPL | 50 μg | AN1792 | 150 |
| 6 | 13 | MPL | 50 μg | AN1528 | 33 |
| 7 | 10 | PBS | | AN1792 | 33 |
| 8 | 10 | PBS | | None | |
| 9 | 10 | Squalene emulsified | 5% | AN1792 | 33 |
| 10 | 10 | Squalene admixed | 5% | AN1792 | 33 |
| 11 | 10 | Alum | 2 mg | AN1792 | 33 |
| 12 | 13 | MPL + Alum | 50 μg/2 mg | AN1792 | 33 |
| 13 | 10 | QS-21 | 5 μg | AN1792 | 33 |
| 14 | 10 | QS-21 | 10 μg | AN1792 | 33 |
| 15 | 10 | QS-21 | 25 AN1792 | AN1792 | 33 |
| 16 | 13 | QS-21 | 25 AN1792 | AN1792 | 150 |
| 17 | 13 | QS-21 | 25 AN1792 | AN1528 | 33 |
| 18 | 13 | QS-21 + MPL | 25 μg/50 μg | AN1792 | 33 |
| 19 | 13 | QS-21 + Alum | 25 μg/2 mg | AN1792 | 33 |

Footnotes:
[a]Number of mice in each group at the initiation of the experiment.
[b]The adjuvants are noted. The buffer for all these formulations was PBS. For group 8, there was no adjuvant and no antigen.

The ELISA titers of antibodies against Aβ42 in each group are shown in below.

TABLE 8

Geometric Mean Antibody Titers Week of Bleed

| Treatment Group | 2.9 | 5.0 | 8.7 | 12.9 | 16.7 |
|---|---|---|---|---|---|
| 1 | 248 | 1797 | 2577 | 6180 | 4177 |
| 2 | 598 | 3114 | 3984 | 5287 | 6878 |
| 3 | 1372 | 5000 | 7159 | 12333 | 12781 |
| 4 | 1278 | 20791 | 14368 | 20097 | 25631 |
| 5 | 3288 | 26242 | 13229 | 9315 | 23742 |
| 6 | 61 | 2536 | 2301 | 1442 | 4504 |
| 7 | 37 | 395 | 484 | 972 | 2149 |
| 8 | 25 | 25 | 25 | 25 | 25 |
| 9 | 25 | 183 | 744 | 952 | 1823 |
| 10 | 25 | 89 | 311 | 513 | 817 |
| 11 | 29 | 708 | 2618 | 2165 | 3666 |
| 12 | 198 | 1458 | 1079 | 612 | 797 |
| 13 | 38 | 433 | 566 | 1080 | 626 |
| 14 | 104 | 541 | 3247 | 1609 | 838 |
| 15 | 212 | 2630 | 2472 | 1224 | 1496 |
| 16 | 183 | 2616 | 6680 | 2085 | 1631 |
| 17 | 28 | 201 | 375 | 222 | 1540 |
| 18 | 31699 | 15544 | 23095 | 6412 | 9059 |
| 19 | 63 | 243 | 554 | 299 | 441 |

The table shows that the highest titers were obtained for groups 4, 5 and 18, in which the adjuvants were 125 μg MPL, 50 μg MPL and QS-21 plus MPL.

IX. Therapeutic Efficacy of Different Adjuvants

A therapeutic efficacy study was conducted in PDAPP transgenic mice with a set of adjuvants suitable for use in humans to determine their ability to potentiate immune responses to Aβ and to induce the immune-mediated clearance of amyloid deposits in the brain.

One hundred eighty male and female, 7.5- to 8.5-month old heterozygous PDAPP transgenic mice were obtained from Charles River Laboratories. The mice were stored into nine groups containing 15 to 23 animals per group to be immunized with AN1792 or AN1528 combined with various adjuvants. Animals were distributed to match the gender, age, and parentage of the animals within the groups as closely as possible. The adjuvants included alum, MPL, and QS-21, each combined with both antigens, and Freund's adjuvant (FA) combined with only AN1792. An additional group was immunized with AN1792 formulated in PBS buffer plus the preservative thimerosal without adjuvant. A ninth group was immunized with PBS alone as a negative control.

Preparation of aggregated Aβ peptides: human Aβ1–40 (AN1528; California Peptides Inc., Napa, Calif.; Lot ME0541) and human Aβ1–42 (AN1792; California Peptides Inc., Lot ME0439) peptides were freshly solubilized for the preparation of each set of injections from lyophilized powders that had been stored desiccated at −20° C. For this purpose, two mg of peptide were added to 0.9 ml of deionized water and the mixture was vortexed to generate a relatively uniform solution or suspension. AN1528 was soluble at this step, in contrast to AN1792. A 100 μl aliquot of 10×PBS (1×PBS: 0.15 M NaCl, 0.01 M sodium phosphate, pH 7.5) was then added at which point AN1528 began to precipitate. The suspensions were vortexed again and incubated overnight at 37° C. for use the next day.

To prepare formulation doses with alum (Groups 1 and 5). Aβ peptide in PBS was added to Alhydrogel (two percent aqueous aluminum hydroxide gel, Sargeant, Inc., Clifton, N.J.) to reach concentrations of 100 μg Aβ peptide per 2 mg of alum. 10×PBS was added to a final dose volume of 200 ml in 1×PBS. The suspension was then gently mixed for approximately 4 hr at RT prior to injection.

To prepare formulation doses for with MPL (Groups 2 and 6), lyophilized powder (Ribi ImmunoChem Research, Inc., Hamilton, Mont.; Lot 67039-E0896B) was added to 0.2% aqueous triethylamine to a final concentration of 1 mg/ml and vortexed. The mixture was heated to 65 to 70° C. for 30 sec to create a slightly opaque uniform suspension of micelles. The solution was stored at 4° C. For each set of injections, 100 μg of peptide per dose in 50 μl PBS, 50 μg of MPL per dose (50 pi) and 100 μl of PBS per dose were mixed in a borosilicate tube immediately before use.

To prepare formulation doses with QS-21 (Groups 3 and 7), lyophilized powder (Aquila, Framingham, MA; Lot A7018R) was added to PBS, pH 6.6–6.7 to a final concentration of 1 mg/ml and vortexed. The solution was stored at −20° C. For each set of injections, 100 μg of peptide per dose in 50 μl PBS, 25 μg of QS-21 per dose in 25 μl PBS and 125 μl of PBS per dose were mixed in a borosilicate tube immediately before use.

To prepare formulation doses with Freund's Adjuvant (Group 4), 100 g of AN1792 in 200 μl PBS was emulsified 1:1 (vol:vol) with Complete Freund's Adjuvant (CFA) in a final volume of 400 μl for the first immunization. For subsequent immunizations, the antigen was similarly emulsified with Incomplete Freund's Adjuvant (IFA). For the formulations containing the adjuvants alum, MPL or QS21, 100 g per dose of AN1792 or AN1528 was combined with alum (2 mg per dose) or MPL (50 g per dose) or QS21 (25 g per dose) in a final volume of 200 μl PBS and delivered by subcutaneous inoculation on the back between the shoulder blades. For the group receiving FA, 100 g of AN1792 was emulsified 1:1 (vol:vol) with Complete Freund's adjuvant (CFA) in a final volume of 400 μl and delivered intraperitoneally for the first immunization, followed by a boost of the same amount of immunogen in Incomplete Freund's adjuvant (IFA) for the subsequent five doses. For the group receiving AN1792 without adjuvant, 10 g AN1792 was combined with 5 g thimerosal in a final volume of 50 µl PBS and delivered subcutaneously. The ninth, control group received only 200 PBS delivered subcutaneously. Immunizations were given on a biweekly schedule for the first three doses, then on a monthly schedule thereafter on days 0, 16, 28, 56, 85 and 112. Animals were bled six to seven days following each immunization starting after the second dose for the measurement of antibody titers. Animals were euthanized approximately one week after the final dose. Outcomes were measured by ELISA assay of Aβ and APP levels in brain and by immunohistochemical evaluation of the presence of amyloid plaques in brain sections. In addition, Aβ-specific antibody titers, and Aβ-dependent proliferative and cytokine responses were determined.

Table 9 shows that the highest antibody titers to Aβ1–42 were elicited with FA and AN1792, titers which peaked following the fourth immunization (peak GMT: 75,386) and then declined by 59% after the final, sixth immunization. The peak mean titer elicited by MPL with AN1792 was 62% lower than that generated with FA (peak GMT: 28,867) and was also reached early in the immunization scheme, after 3 doses, followed by a decline to 28% of the peak value after the sixth immunization. The peak mean titer generated with QS-21 combined with AN1792 (GMT: 1,511) was about 5-fold lower than obtained with MPL. In addition, the kinetics of the response were slower, since an additional immunization was required to reach the peak response. Titers generated by alum-bound AN1792 were marginally greater than those obtained with QS-21 and the response kinetics were more rapid. For AN1792 delivered in PBS with thimerosal the frequency and size of titers were barely greater than that for PBS alone. The peak titers generated with MPL and AN1528 (peak GMT 3099) were about 9-fold lower than those with AN1792. Alum-bound AN1528 was very poorly immunogenic with low titers generated in only some of the animals. No antibody responses were observed in the control animals immunized with PBS alone.

TABLE 9

Geometric Mean Antibody Titers[a]
Week of Bleed

| Treatment | 3.3 | 5.0 | 9.0 | 13.0 | 17.0 |
|---|---|---|---|---|---|
| Alum/ | 102 | 1,081 | 2,366 | 1,083 | 572 |
| AN1792 | (12/21)[b] | (17/20) | (21/21) | (19/21) | (18/21) |
| MPL/ | 6241 | 28,867 | 1,1242 | 5,665 | 8,204 |
| AN1792 | (21/21) | (21/21) | (21/21) | (20/20) | (20/20) |
| QS-21/ | 30 | 227 | 327 | 1,511 | 1,188 |
| AN1792 | (1/20) | (10/19) | (10/19) | (17/18) | (14/18) |
| CFA/ | 10,076 | 61,279 | 75,386 | 41,628 | 30,574 |
| AN1792 | (15/15) | (15/15) | (15/15) | (15/15) | (15/15) |
| Alum/ | 25 | 33 | 39 | 37 | 31 |
| AN1528 | (0/21) | (1/21) | (3/20) | (1/20) | (2/20) |
| MPL/ | 184 | 2,591 | 1,653 | 1,156 | 3,099 |
| AN1528 | (15/21) | (20/21) | (21/21) | (20/20) | (20/20) |
| QS-21/ | 29 | 221 | 51 | 820 | 2,994 |
| AN1528 | (1/22) | (13/22) | (4/22) | (20/22) | (21/22) |
| PBS plus | 25 | 33 | 39 | 37 | 47 |
| Thimerosal | (0/16) | (2/16) | (4/16) | (3/16) | (4/16) |
| PBS | 25 | 25 | 25 | 25 | 25 |
|  | (0/16) | (0/16) | (0/15) | (0/12) | (0/16) |

Footnotes:
[a]Geometric mean antibody titers measured against Aβ1-42
[b]Number of responders per group The results of AN1792 or AN1592 treatment with various adjuvants, or thimerosal on cortical amyloid burden in 12-month old mice determined by ELISA are shown in FIGS. 15A–15E. In PBS control PDAPP mice the median level of total Aβ in the cortex at 12 months was 1,817 ng/g (FIG. 15A). Notably reduced levels of Aβ were observed in mice treated with AN1792 plus CFA/IFA (FIG. 15C), AN1792 plus alum (FIG. 15D), AN1792 plus MPL (FIG. 15E) and QS21 plus AN1792 (FIG. 15E). The reduction reached statistical significance (p<0.05) only for AN1792 plus CFA/IFA (FIG. 15C). However, as shown in Examples I and III, the effects of immunization in reducing Aβ levels become substantially greater in 15 month and: 18 month old mice. Thus, it is expected that at least the AN1792 plus alum, AN1792 plus MPL and AN1792 plus QS21 compositions will achieve statistical significance in treatment of older mice. By contrast, the AN1792 plus the preservative thimerosal (FIG. 15D) showed a median level of A,8 about the same as that in the PBS treated mice. Similar results were obtained when cortical levels of Aβ42 were compared. The median level of Aβ42 in PBS controls was 1624 ng/g. Notably reduced median levels of 403, 1149, 620 and 714 were observed in the mice treated with AN1792 plus CFA/IFA, AN1792 plus alum, AN1792 plus MPL and AN1792 plus QS21 respectively, with the reduction achieving statistical significance (p=0.05) for the AN1792 CFA/IFAβ treatment group. The median level in the AN1792 thimerosal treated mice was 1619 ng/g A,342.

A further therapeutic adjuvant/immunogen efficacy study was performed in 9–10.5 month old male and female heterozygous PDAPP transgenic mice. The duration of the study was 25 weeks with 29–40 animals per treatment group; therefore the animals were 15–16.5 months old at termination. The treatment groups are identified in Table 10 below.

| | Adjuvant | Immunogen | Dilution Buffer | Administration |
|---|---|---|---|---|
| Group 1: | MPL-SE | AN1792-GCS (75 µg) | PBS | SC (250 µl) |
| Group 2: | ISA 51 | AN1792-GCS (75 µg) | PBS | IP (400 µl) |
| Group 3: | QS21 | AN1792-GCS (75 µg) | PBS | SC (250 µl) |
| Group 4: | QS21 abbrev. | AN1792-GCS (75 µg) | PBS | SC (250 µl) |
| Group 5: | PBS | — | — | SC (250 µl) |

Table 10 abbreviations: MAP - multi-antigenic peptide; TT - tetanus toxoid t-cell epitope (830–844); SQ - subcutaneous; IP - intraperitoneally; PBS - phosphate, buffered saline; ISA-51 is a commercially available adjuvant similar to IFA; GCS is a glycine/citrate/sucrose formulation, MPL-SE is MPL in a stabilized water and oil emulsion.

The immunization schedule was identical for all of the treatment groups except for Group 3, the QS21/AN1792 abbreviated schedule group. The mice were injected on weeks 0, 2, 4, 8, 12, 16, 20, 24, with bleeds on weeks 3, 5, 9, 13, 17, 21 and 25. Groups 1, 2, received eight injections and Group 3 received four injections during the 25-week period of the study. Group 4, the QS21/AN1792 abbreviated schedule, received injections on weeks 0, 2, 4, and 8 only. This group was not injected for the remainder of the study, although they were bled on the same bleed schedule as the rest of the study to follow titer decay. Groups 3 and 5, QS21/AN1792 and PBS respectively, served as the positive and negative controls for this study.

The titers were determined by the anti-Aβ antibody titer assay.

Group 1, the MPL-SE/AN1792 group, raised a peak geometric mean titer (GMT) of 17,100 at 9 weeks falling to a GMT of 10,000 at 25 weeks. Initially, the MPL-SE titers rose at a somewhat higher rate than the QS21/AN1792 control group (Group 4).

Group 2, the ISA 51/AN1792 group, produced high titers throughout the study reaching a GMT of over 100,000 for the last 9 weeks of the study.

Group 3, the QS21/AN1792 control group, reached its peak titer at 17 weeks with a GMT of 16,000. The titer then fell over the next 8 weeks to finish with a GMT of 8,700. One animal in this group failed to raise a titer over the entire course of the experiment.

Group 4, the QS21/AN1792 abbreviated injection schedule group, reached a peak titer of 7,300 at 13 weeks, five weeks after its final injection. The titer then fell to a GMT of 2,100 at the final bleed (25 weeks). As in the control group, one animal failed to raise a detectable titer, while another animal lost all titer by the end of the decay period.

Group 5, the PBS alone group, had no titers.

To evaluate the cortical Aβ levels, total Aβ and Aβ1–42 were measured by ELISA. Briefly, one brain hemisphere was dissected for cortical, hippocampal, and cerebellar tissue followed by homogenization in 5M guanidine buffer and assayed for brain Aβ. The cortical total Aβ and Aβ42 results are similar. A Mann-Whitney statistical analysis was performed to determine significance between the groups with a p value of 0.05 indicating a significant change in Aβ.

All treatment groups significantly lowered total Aβ levels as compared to the PBS control group (see Table 11). The MPL-SE/AN1792 group, showed the greatest change in AB, and it is significantly better than the other treatment groups. The QS21/AN1792 abbreviated group, was similar in its overall change of Aβ to the QS21 control group that received all eight injections. The Aβ levels in the ISA 51/AN1792 group, were similarly lowered compared to the CFA/IFA:MAP(Aβ1-7) group.

TABLE 11

Cortical Aβ levels

|  | PBS | MPL-SE | ISA | QS-21 | QS-21 (4) |
|---|---|---|---|---|---|
| MEDIAN (ng/g tissue) | 7,335 | 1,236 | 3,026 | 2,389 | 2,996 |
| RANGE (ng/g tissue) | 550–18,358 | 70–3,977 | 23–9,777 | 210–11,167 | 24–16,834 |
| p value | — | <0.0001 | <0.0001 | <0.0001 | <0.0001 |
| N | 38 | 29 | 36 | 34 | 40 |

In conclusion, MPL-SE, ISA-51 and QS21 adjuvants combined with AN1792 are effective in inducing a sufficient immune response significantly to retard Aβ deposition in the cortex.

X. Toxicity Analysis

Tissues were collected for histopathologic examination at the termination of studies described in Examples 2, 3 and 7. In addition, hematology and clinical chemistry were performed on terminal blood samples from Examples 3 and 7. Most of the major organs were evaluated, including brain, pulmonary, lymphoid, gastrointestinal, liver, kidney, adrenal and gonads. Although sporadic lesions were observed in the study animals, there were no obvious differences, either in tissues affected or lesion severity, between AN1792 treated and untreated animals. There were no unique histopathological lesions noted in AN-1528-immunized animals compared to PBS-treated or untreated animals. There were also no differences in the clinical chemistry profile between adjuvant groups and the PBS treated animals in Example 7. Although there were significant increases in several of the hematology parameters between animals treated with AN1792 and Freund's adjuvant in Example 7 relative to PBS treated animals, these type of effects are expected from Freund's adjuvant treatment and the accompanying peritonitis and do not indicate any adverse effects from AN1792 treatment. Although not part of the toxicological evaluation, PDAPP mouse brain pathology was extensively examined as part of the efficacy endpoints. No sign of treatment related adverse effect on brain morphology was noted in any of the studies. These results indicate that AN1792 treatment is well tolerated and at least substantially free of side effects.

XI. Therapeutic Treatment With Anti-Aβ Antibodies

This examples tests the capacity of various monoclonal and polyclonal antibodies to Aβ to inhibit accumulation of Aβ in the brain of heterozygotic transgenic mice.

1. Study Design

Sixty male and female, heterozygous PDAPP transgenic mice, 8.5 to 10.5 months of age were obtained from Charles River Laboratory. The mice were sorted into six groups to be treated with various antibodies directed to AII. Animals were distributed to match the gender, age, parentage and source of the animals within the groups as closely as possible. As shown in Table 10, the antibodies included four murine A,6-specific monoclonal antibodies, 2H3 (directed to Aβ residues 1–12), 10D5 (directed to All residues 1–16) (details of the deposit of 10D5 are discussed in Example VI. suvra), 266 (directed to A, residues 13–28 and binds to monomeric but not to aggregated AN1792), 21F12 (directed to A,B residues 33–42). A fifth group was treated, with an A-specific polyclonal antibody fraction (raised by immunization with aggregated AN1792). The negative control group received the diluent, PBS, alone without antibody.

The monoclonal antibodies were injected at a dose of about 10 mg/kg (assuming that the mice weighed 50 g). Injections were administered intraperitoneally every seven days on average to maintain anti-Aβ titers above 1000. Although lower titers were measured for mAb 266 since it does not bind well to the aggregated AN1792 used as the capture antigen in the assay, the same dosing schedule was maintained for this group. The group receiving monoclonal antibody 2H3 was discontinued within the first three weeks since the antibody was cleared too rapidly in vivo. Animals were bled prior to each dosing for the measurement of antibody titers. Treatment was continued over a six-month period for a total of 196 days. Animals were euthanized one week after the final dose.

TABLE 12

EXPERIMENTAL DESIGN

| Treatment Group | N[a] | Treatment Antibody | Antibody Specificity | Antibody Isotype |
|---|---|---|---|---|
| 1 | 9 | none (PBS alone) | NA[b] | NA |
| 2 | 10 | Polyclonal | Aβ1-42 | mixed |
| 3 | 0 | mAb[c]2H3 | Aβ1-12 | IgG1 |
| 4 | 8 | mAb 10D5 | Aβ1-16 | IgG1 |
| 5 | 6 | mAb 266 | Aβ13-28 | IgG1 |
| 6 | 8 | mAb 21F12 | Aβ33-42 | IgG2a |

Footnotes
[a]. Number of mice in group at termination of the experiment. All groups started with 10 animals per group.
[b]. NA: not applicable
[c]. mAb: monoclonal antibody 2. Materials and Methods
  a. Preparation of the Antibodies
  The anti-Aβ polyclonal antibody was prepared from blood collected from two groups of animals. The first group consisted of 100 female Swiss Webster mice, 6 to 8 weeks of age. They were immunized on days 0, 15, and 29 with 100 μg of AN1792 combined with CFA/IFA. A fourth injection was given on day 36 with one-half the dose of AN1792. Animals were exsanguinated upon sacrifice at day 42, serum was prepared and the sera were pooled to create a total of 64 ml. The second group consisted of 24 female mice isogenic with the PDAPP mice but nontransgenic for the human APP gene, 6 to 9 weeks of age. They were immunized on days 0, 14, 28 and 56 with 100 μg of AN1792 combined with CFA/IFA. These animals were also exsanguinated upon sacrifice at day 63, serum was prepared and pooled for a total of 14 ml. The two lots of sera were pooled. The antibody fraction was purified using two sequential rounds of precipitation with 50% saturated ammonium sulfate. The final precipitate was dialyzed against PBS and tested for endotoxin. The level of endotoxin was less than 1 EU/mg.

The anti-Aβ monoclonal antibodies were prepared from ascites fluid. The fluid was first delipidated by the addition of concentrated sodium dextran sulfate to ice-cold ascites fluid by stirring on ice to a reach a final concentration of 0.238%. Concentrated $CaCl_2$ was then added with stirring to reach a final concentration of 64 mM. This solution was centrifuged at 10,000 ×g and the pellet was discarded. The supernatant was stirred on ice with an equal volume of saturated ammonium sulfate added dropwise. The solution was centrifuged again at 10,000 ×g and the supernatant was discarded. The pellet was resuspended and dialyzed against 20 mM Tris-HCl, 0.4 M NaCl, pH 7.5. This fraction was applied to a Pharmacia FPLC Sepharose Q Column and dine. These were serially diluted and the level of amyloid peptide or APP was quantitated by comparison to a series of dilutions of standards of Aβ peptide or APP of known concentrations in an ELISA format.

The levels of total Aβ and of Aβ1–42 measured by ELISA in homogenates of the cortex, and the hippocampus and the level of total Aβ in the cerebellum are shown in Tables 11, 12, and 13, respectively. The median concentration of total Aβ for the control group, inoculated with PBS, was 3.6-fold higher in the hippocampus than in the cortex (median of 63,389 ng/g hippocampal tissue compared to 17,818 ng/g for the cortex). The median level in the cerebellum of the control group (30.6 ng/g tissue) was more than 2,000-fold lower than in the hippocampus. These levels are similar to those that we have previously reported for heterozygous PDAPP transgenic mice of this age (Johnson-Wood et al., 1997).

For the cortex, one treatment group had a median Aβ level, measured as Aβ1–42, which differed significantly from that of the control group (p<0.05), those animals receiving the polyclonal anti-Aβ antibody as shown in Table 13. The median level of Aβ1–42 was reduced by 65%, compared to the control for this treatment group. The median levels of Aβ1–42 were also significantly reduced by 55% compared to the control in one additional treatment group, those animals dosed with the mAb 10D5 (p=0.0433).

TABLE 13

CORTEX

| | | Medians | | | | | Means | |
| --- | --- | --- | --- | --- | --- | --- | --- | --- |
| | | Total Aβ | | | Aβ42 | | Total Aβ | Aβ42 |
| Treatment Group | N[a] | LISA value[b] | P value[c] | % Change | ELISA value | P value | % Change | ELISA value | ELISA value |
| PBS | 9 | 17318 | NA[d] | NA | 13802 | NA | NA | 16150 +/− 7456[e] | 12621 +/− 5738 |
| Polyclonal anti-Aβ42 | 10 | 6160 | 0.0055 | −65 | 4892 | 0.0071 | −65 | 5912 +/− 4492 | 4454 +/− 3347 |
| mAb 10D5 | 8 | 7915 | 0.1019 | −56 | 6214 | 0.0433 | −55 | 9695 +/− 6929 | 6943 +/− 3351 |
| mAb 266 | 6 | 9144 | 0.1255 | −49 | 5481 | 0.1255 | −39 | 9204 +/− 9293 | 7489 +/− 6921 |
| mAb 21F12 | 8 | 15158 | 0.2898 | −15 | 13578 | 0.7003 | −2 | 12481 +/− 7082 | 11005 +/− 6324 |

Footnotes:
[a]Number of animals per group at the end of the experiment
[b]ng/g tissue
[c]Mann Whitney analysis
[d]NA: not applicable
[e]Standard Deviation eluted with a reverse gradient from 0.4 M to 0.275 M NaCl in 20 mM Tris-HCl, pH 7.5.

The antibody peak was identified by absorbance at 280 nm and appropriate fractions were pooled. The purified antibody preparation was characterized by measuring the protein concentration using the BCA method and the purity using SDS-PAGE. The pool was also tested for endotoxin. The level of endotoxin was less than 1 EU/mg. titers, titers less than 100 were arbitrarily assigned a titer value of 25.

3. Aβ and APP Levels in the Brain

Following about six months of treatment with the various anti-Aβ antibody preparations, brains were removed from the animals following saline perfusion. One hemisphere was prepared for immunohistochemical analysis and the second was used for the quantitation of Aβ and APP levels. To measure the concentrations of various forms of beta amyloid peptide and amyloid precursor protein (APP), the hemisphere was dissected and homogenates of the hippocampal, cortical, and cerebellar regions were prepared in 5 M guani- In the hippocampus, the median percent reduction of total Aβ associated with treatment with polyclonal anti-Aβ antibody (50%, p=0.0055) was not as great as that observed in the cortex (65%) (Table 14). However, the absolute magnitude of the reduction was almost 3-fold greater in the hippocampus than in the cortex, a net reduction of 31,683 ng/g tissue in the hippocampus versus 11,658 ng/g tissue in the cortex. When measured as the level of the more amyloidogenic form of Aβ, Aβ1–42, rather than as total Aβ, the reduction achieved with the polyclonal antibody was significant (p=0.0025). The median levels in groups treated with the mAbs 10D5 and 266 were reduced by 33% and 21%, respectively.

TABLE 14

HIPPOCAMPUS

| | | Medians | | | | | | Means | |
| --- | --- | --- | --- | --- | --- | --- | --- | --- | --- |
| | | Total Aβ | | | Aβ42 | | | Total Aβ | Aβ42 |
| Treatment Group | N[a] | ELISA value[b] | P value[c] | % Change | ELISA value | P value | % Change | ELISA value | ELISA value |
| PBS | 9 | 63389 | NA[d] | NA | 54429 | NA | NA | 58351 +/− 13308[e] | 52801 +/− 14701 |
| Polyclonal anti-Aβ42 | 10 | 31706 | 0.0055 | −50 | 27127 | 0.0025 | −50 | 30058 +/− 22454 | 24853 +/− 18262 |
| mAb 10D5 | 8 | 46779 | 0.0675 | −26 | 36290 | 0.0543 | −33 | 44581 +/− 18632 | 36465 +/− 17146 |
| mAb 266 | 6 | 48689 | 0 0990 | −23 | 43034 | 0.0990 | −21 | 36419 +/− 27304 | 32919 +/− 25372 |
| mAb 21F12 | 8 | 51563 | 0.7728 | −19 | 47961 | 0.8099 | −12 | 57327 +/− 28927 | 50305 +/− 23927 |

Footnotes:
[a]Number of animals per group at the end of the experiment
[b]ng/g tissue
[c]Mann Whitney analysis
[d]NA: not applicable
[e]Standard Deviation Total Aβ was also measured in the cerebellum (Table 15). Those groups dosed with the polyclonal anti-Aβ and the 266 antibody showed significant reductions of the levels of total Aβ (43% and 46%, p=0.0033 and p=0.0184, respectively) and that group treated with 10D5 had a near significant reduction (29%, p=0.0675).

TABLE 15

CEREBELLUM

| | | Medians Total Aβ | | | Means |
| --- | --- | --- | --- | --- | --- |
| Treatment Group | N[a] | ELISA value[b] | P value[c] | % Change | Total Aβ ELISA value |
| PBS | 9 | 30.64 | NA[d] | NA | 40.00 +/− 31.89[e] |
| Polyclonal anti-Aβ42 | 10 | 17.61 | 0.0033 | −43 | 18.15 +/− 4.36 |
| mAb 10D5 | 8 | 21.68 | 0.0675 | −29 | 27.29 +/− 19.43 |
| mAb 266 | 6 | 16.59 | 0.0184 | −46 | 19.59 +/− 6.59 |
| mAb 21F12 | 8 | 29.80 | >0.9999 | −3 | 32.88 +/− 9.90 |

Footnotes:
[a]. Number of animals per group at the end of the experiment
[b]. ng/g tissue
[c]. Mann Whitney analysis
[d]. NA: not applicable
[e]. Standard Deviation APP concentration was also determined by ELISA in the cortex and cerebellum from antibody-treated and control, PBS-treated mice. Two different APP assays were utilized. The first, designated APP-α/FL, recognizes both APP-alpha (α, the secreted form of APP which has been cleaved within the Aβ sequence), and full-length forms (FL) of APP, while the second recognizes only APP-α. In contrast to the treatment-associated diminution of Aβ in a subset of treatment groups, the levels of APP were virtually unchanged in all of the treated compared to the control animals. These results indicate that the immunizations with Aβ antibodies deplete Aβ without depleting APP.

In summary, Aβ levels were significantly reduced in the cortex, hippocampus and cerebellum in animals treated with the polyclonal antibody raised against AN1792. To a lesser extent monoclonal antibodies to the amino terminal region of Aβ1–42, specifically amino acids 1–16 and 13–28 also showed significant treatment effects.

4. Histochemical Analyses

The morphology of Aβ-immunoreactive plaques in subsets of brains from mice in the PBS, polyclonal Aβ42, 21F12, 266 and 10D5 treatment groups was qualitatively compared to that of previous studies in which standard immunization procedures with Aβ42 were followed.

The largest alteration in both the extent and appearance of amyloid plaques occurred in the animals immunized with the polyclonal Aβ42 antibody. The reduction of amyloid load, eroded plaque morphology and cell-associated Aβ immunoreactivity closely resembled effects produced by the standard immunization procedure. These observations support the ELISA results in which significant reductions in both total Aβ and A142 were achieved by administration of the polyclonal Aβ42 antibody.

In similar qualitative evaluations, amyloid plaques in the 10D5 group were also reduced in number and appearance, with some evidence of cell-associated Aβ immunoreactivity. Relative to control-treated animals, the polyclonal 1 g fraction against Aβ and one of the monoclonal antibodies (10D5) reduced plaque burden by 93% and 81%, respectively (<0.005). 21F12 appeared to have a relatively modest effect on plaque burden. Micrographs of brain after treatment with pabAβ$_{1-42}$ show diffuse deposits and absence of many of the larger compacted plaques in the pabAβ$_{1-42}$ treated group relative to control treated animals.

5. Measurement of Antibody Titers

Figure 16:
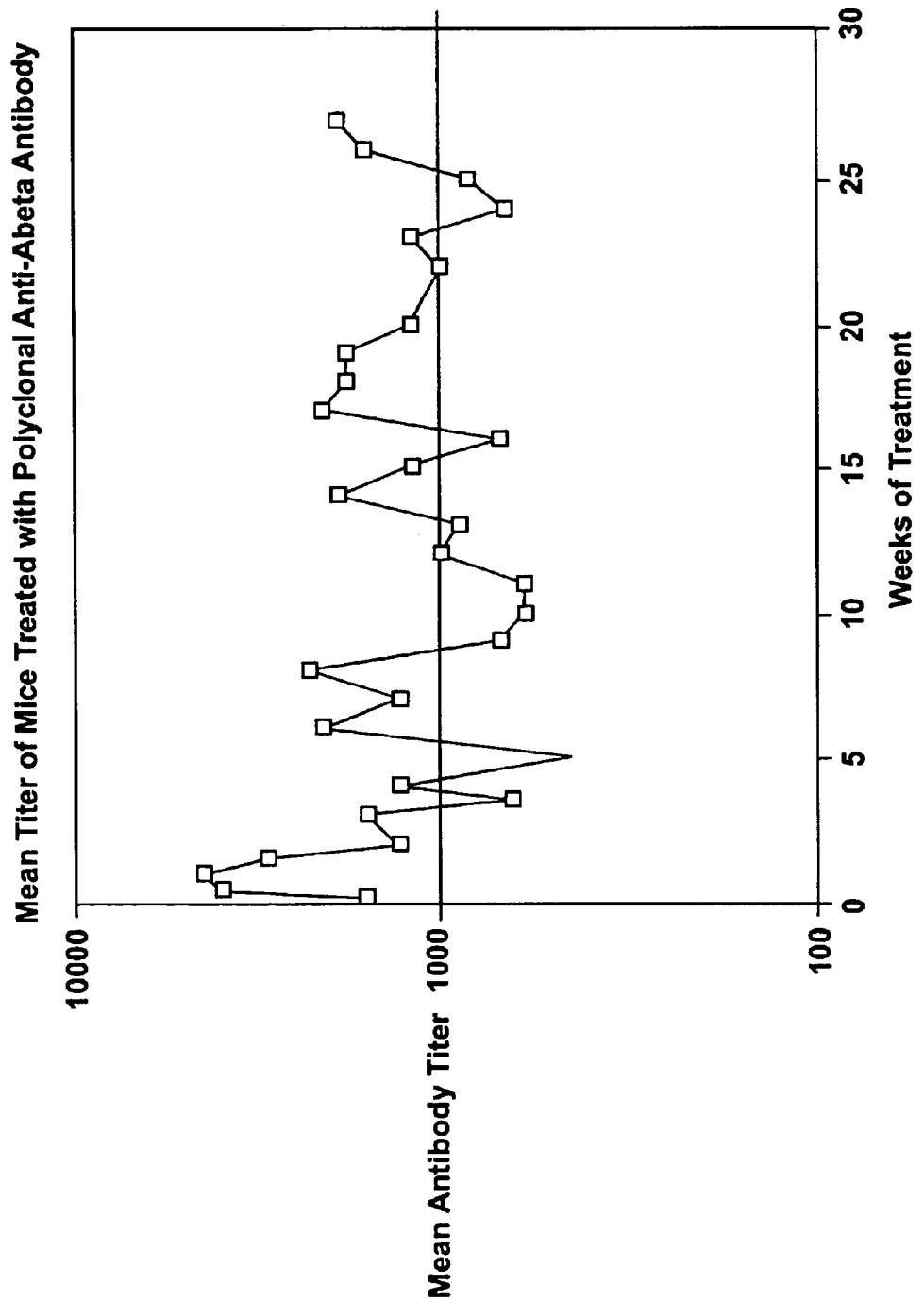
FIG. 16: Mean titer of mice treated with polyclonal antibody to Aβ.
Figure 17:
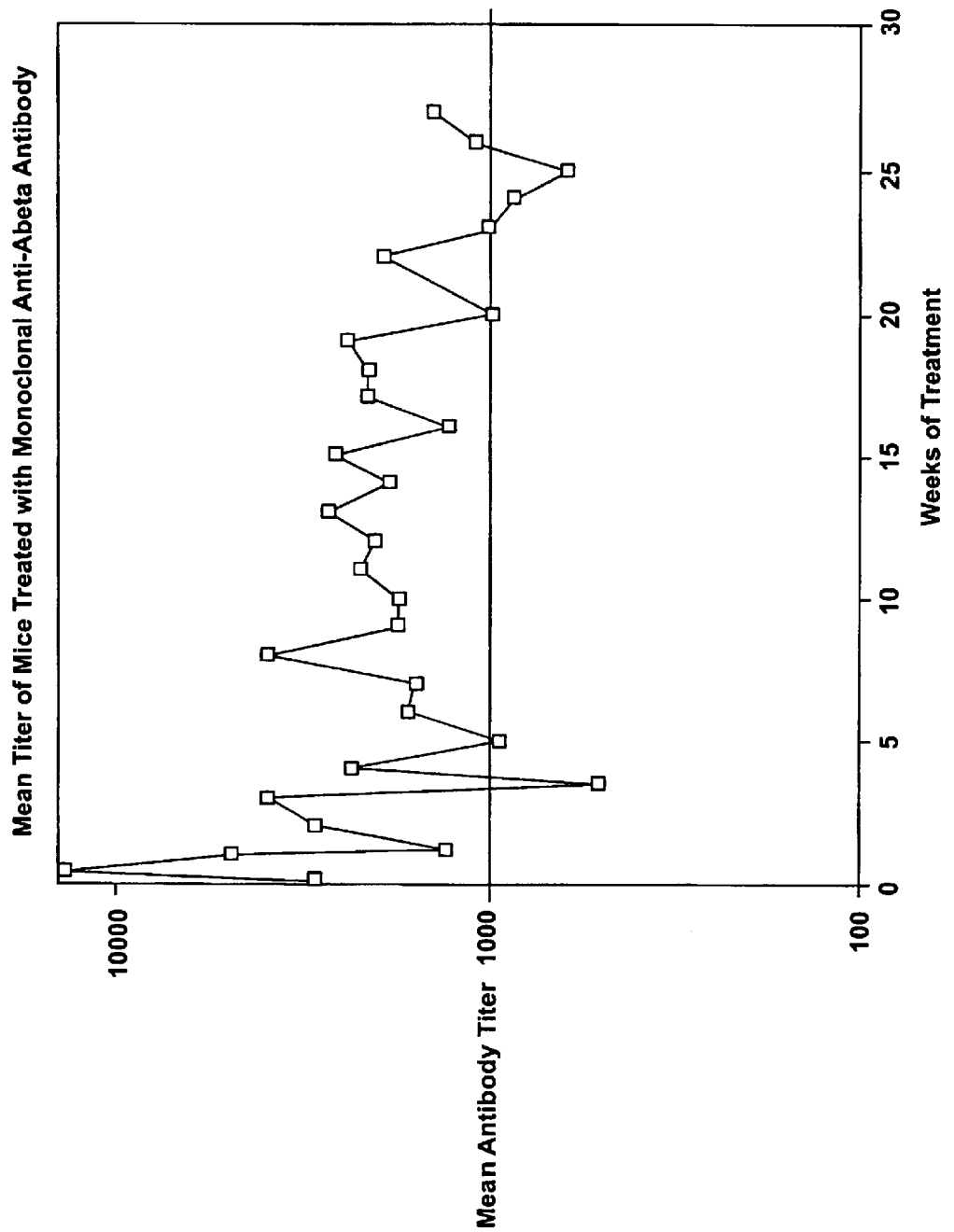
FIG. 17: Mean titer of mice treated with monoclonal antibody 10D5 to Aβ.
Figure 18:
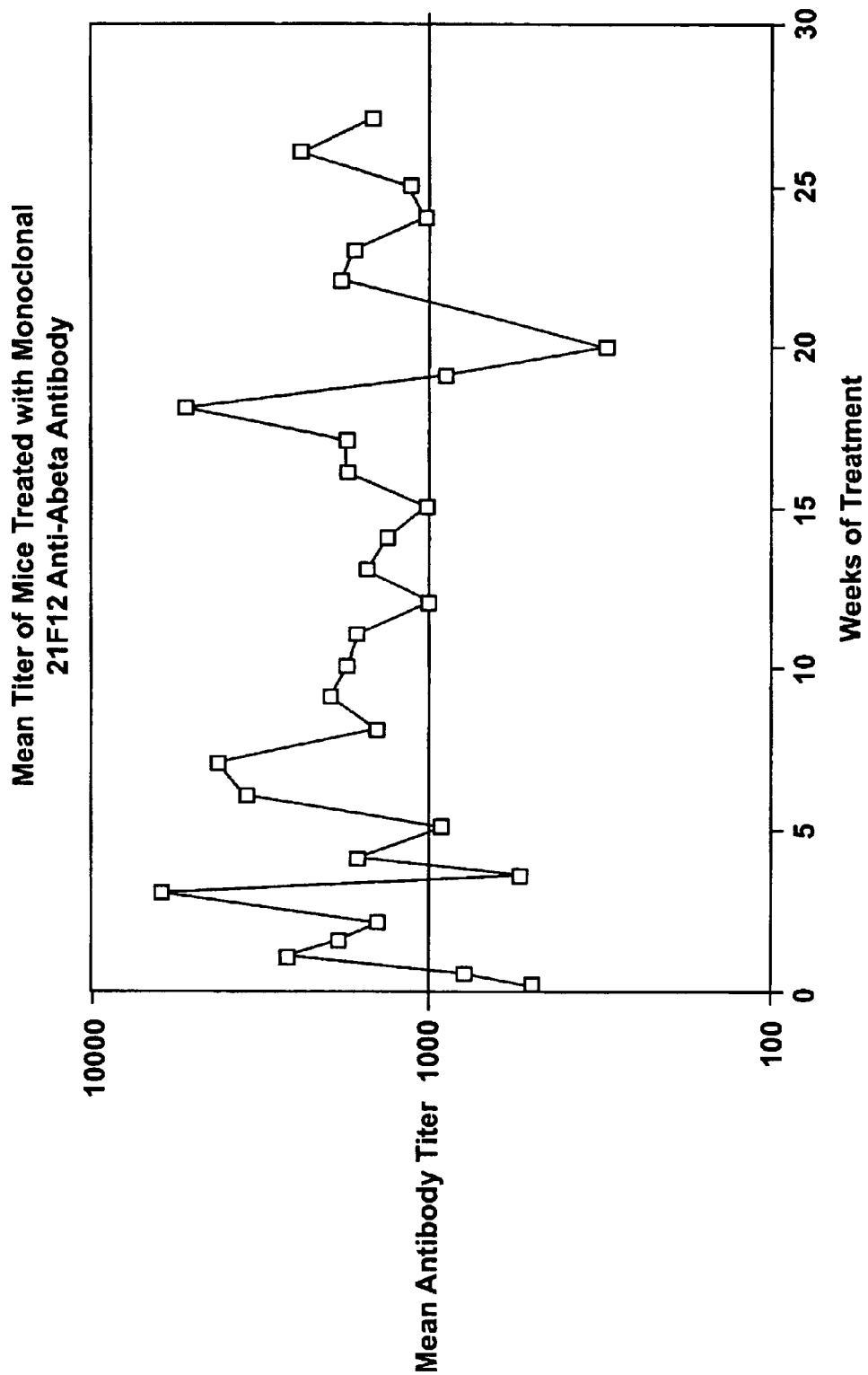
FIG. 18: Mean titer of mice treated with monoclonal antibody 2F12 to Aβ.

A subset of three randomly chosen mice from each group were bled just prior to each intraperitoneal inoculation, for a total of 30 bleeds. Antibody titers were measured as Aβ1–42-binding antibody using a sandwich ELISA with plastic multi-well plates coated with Aβ1–42 as described in detail in the General Materials and Methods. Mean titers for each bleed are shown in FIGS. 16–18 for the polyclonal antibody and the monoclonals 10D5 and 21 F 12, respectively. Titers averaged about 1000 over this time period for the polyclonal antibody preparation and were slightly above this level for the 10D5- and 21 F 12-treated animals.

6. Lymphoproliferative Responses

Aβ-dependent lymphoproliferation was measured using spleen cells harvested eight days following the final antibody infusion. Freshly harvested cells, $10^5$ per well, were cultured for 5 days in the presence of Aβ1–40 at a concentration of 5 FM for stimulation. As a positive control, additional cells were cultured with the T cell mitogen, PHA, and, as a negative control, cells were cultured without added peptide.

Splenocytes from aged PDAPP mice passively immunized with various anti-Aβ antibodies were stimulated in vitro with AN1792 and proliferative and cytokine responses were measured. The purpose of these assays was to determine if passive immunization facilitated antigen presentation, and thus priming of T cell responses specific for AN1792. No AN1792-specific proliferative or cytokine responses were observed in mice passively immunized with the anti-Aβ antibodies.

XII: Further Study of Passive Immunization

In a second study, treatment with 10D5 was repeated and two additional anti-Aβ antibodies were tested, monoclonals 3D6 (Aβ15) and 16C11 (Aβ$_{33-42}$). Control groups received either PBS or an irrelevant isotype-matched antibody (TM2a). The mice were older (11.5–12 month old heterozygotes) than in the previous study, otherwise the experimental design was the same. Once again, after six months of treatment, 10D5 reduced plaque burden by greater than 80% relative to either the PBS or isotype-matched antibody controls (p=0.003). One of the other antibodies against Aβ, 3D6, was equally effective, producing an 86% reduction (p=0.003). In contrast, the third antibody against the peptide, 16C11, failed to have any effect on plaque burden. Similar findings were obtained with Aβ$_{42}$ ELISA measurements. These results demonstrate that an antibody response against Aβ peptide, in the absence of T cell immunity, is sufficient to decrease amyloid deposition in PDAPP mice, but that not all anti-Aβ antibodies are efficacious. Antibodies directed to epitopes comprising amino acids 1–5 or 3–7 of Aβ are particularly efficacious.

In summary, we have shown that passively administered antibodies against Aβ reduced the extent of plaque deposition in a mouse model of Alzheimer's disease. When held at modest serum concentrations (2570 μg/ml), the antibodies gained access to the CNS at levels sufficient to decorate β-amyloid plaques. Antibody entry into the CNS was not due to abnormal leakage of the blood-brain barrier since there was no increase in vascular permeability as measured by Evans Blue in PDAPP mice. In addition, the concentration of antibody in the brain parenchyma of aged PDAPP mice was the same as in non-transgenic mice, representing 0.1% of the antibody concentration in serum (regardless of isotype).

XIII: Monitoring of Antibody Binding

To determine whether antibodies against AS could be acting directly within the CNS, brains taken from saline-perfused mice at the end of the Example XII, were examined for the presence of the peripherally-administered antibodies. Unfixed cryostat brain sections were exposed to a fluorescent reagent against mouse immunoglobulin (goat anti-mouse IgG-Cy3). Plaques within brains of the 10D5 and 3D6 groups were strongly decorated with antibody, while there was no staining in the 16C11 group. To reveal the full extent of plaque deposition, serial sections of each brain were first immunoreacted with an anti-Aβ antibody, and then with the secondary reagent. 10D5 and 3D6, following peripheral administration, gained access to most plaques within the CNS. The plaque burden was greatly reduced in these treatment groups compared to the 16C11 group. These data indicate that peripherally administered antibodies can enter the CNS where they can directly trigger amyloid clearance. It is likely that 16C11 also had access to the plaques but was unable to bind.

XIV: ex Vivo Screening Assay for Activity of an Antibody Against Amyloid Deposits To examine the effect of antibodies on plaque clearance, we established an ex vivo assay in which primary microglial cells were cultured with unfixed cryostat sections of either PDAPP mouse or human AD brains. Microglial cells were obtained from the cerebral cortices of neonate DBA/2N mice (1–3 days). The cortices were mechanically dissociated in HBSS⁻ (Hanks' Balanced Salt Solution, Sigma) with 50 μg/ml DNase I (Sigma). The dissociated cells were filtered with a 100 μm cell strainer (Falcon), and centrifuged at 1000 rpm for 5 minutes. The pellet was resuspended in growth medium (high glucose DMEM, 10%FBS, 25ng/ml rmGM-CSF), and the cells were plated at a density of 2 brains per T-75 plastic culture flask. After 7–9 days, the flasks were rotated on an orbital shaker at 200 rpm for 2h at 37° C. The cell suspension was centrifuged at 1000 rpm and resuspended in the assay medium.

10-μm cryostat sections of PDAPP mouse or human AD brains (post-mortem interval<3hr) were thaw mounted onto poly-lysine coated round glass coverslips and placed in wells of 24-well tissue culture plates. The coverslips were washed twice with assay medium consisting of H-SFM (Hybridoma-serum free medium, Gibco BRL) with 1% FBS, glutamine, penicillin/streptomycin, and 5ng/ml rmGM-CSF (R&D). Control or anti-Aβ antibodies were added at a 2×concentration (5 μg/ml final) for 1 hour. The microglial cells were then seeded at a density of 0.8×10⁶ cells/ml assay medium. The cultures were maintained in a humidified incubator (37° C., 5%CO$_2$) for 24hr or more. At the end of the incubation, the cultures were fixed with 4% paraformaldehyde and permeabilized with 0.1% Triton-X100. The sections were stained with biotinylated 3D6 followed by a streptavidin/Cy3 conjugate (Jackson ImmunoResearch). The exogenous microglial cells were visualized by a nuclear stain (DAPI). The cultures were observed with an inverted fluorescent microscope (Nikon, TE300) and photomicrographs were taken with a SPOT digital camera using SPOT software (Diagnostic instruments). For Western blot analysis, the cultures were extracted in 8M urea, diluted 1:1 in reducing tricine sample buffer and loaded onto a 16% tricine gel (Novex). After transfer onto immobilon, blots were exposed to 5 μg/ml of the pabAβ42 followed by an HRP-conjugated anti-mouse antibody, and developed with ECL (Amersham).

When the assay was performed with PDAPP brain sections in the presence of 16C11 (one of the antibodies against Aβ that was not efficacious in vivo), β-amyloid plaques remained intact and no phagocytosis was observed. In contrast, when adjacent sections were cultured in the presence of 10D5, the amyloid deposits were largely gone and the microglial cells showed numerous phagocytic vesicles containing Aβ. Identical results were obtained with AD brain sections; 10D5 induced phagocytosis of AD plaques, while 16C11 was ineffective. In addition, the assay provided comparable results when performed with either mouse or human microglial cells, and with mouse, rabbit, or primate antibodies against Aβ.

Table 16 shows whether binding and/or phagocytosis was obtained for several different antibody binding specificities. It can be seen that antibodies binding to epitopes within aa 1–7 both bind and clear amyloid deposits, whereas antibodies binding to epitopes within amino acids 4–10 bind without clearing amyloid deposits. Antibodies binding to epitopes C-terminal to residue 10 neither bind nor clear amyloid deposits.

TABLE 16

Analysis of Epitope Specificity

| | Antibody epitope | isotype | Staining | Phagocytosis |
|---|---|---|---|---|
| N-Term | | | | |
| mab | | | | |
| 3D6 | 1–5 | IgG2b | + | + |
| 10D5 | 3–6 | IgG1 | + | + |
| 22C8 | 3–7 | IgG2a | + | + |
| 6E10 | 5–10 | IgG1 | + | – |
| 14A8 | 4–10 | rat IgG1 | + | – |
| 13–28 | | | | |
| 18G11 | 10–18 | rat IgG1 | – | – |
| 266 | 16–24 | IgG1 | – | – |
| 22D12 | 18–21 | IgG2b | – | – |
| C-Term | | | | |
| 2G3 | –40 | IgG1 | – | – |
| 16C11 | –40/–42 | IgG1 | – | – |
| 21F12 | –42 | IgG2a | – | – |
| Immune serum | | | | |
| rabbit (CFA) | 1–6 | | + | + |
| mouse (CFA) | 3–7 | | + | + |
| mouse (QS-21) | 3–7 | | + | + |
| monkey (QS-21) | 1–5 | | + | + |
| mouse (MAP1-7) | | | + | + |

Table 17 shows results obtained with several antibodies against Aβ, comparing their abilities to induce phagocytosis in the ex vivo assay and to reduce in vivo plaque burden in passive transfer studies. Although 16C11 and 21 F12 bound to aggregated synthetic Aβ peptide with high avidity, these antibodies were unable to react with 13-amyloid plaques in unfixed brain sections, could not trigger phagocytosis in the ex vivo assay, and were not efficacious in vivo. 10D5, 3D6, and the polyclonal antibody against Aβ were active by all three measures. The 22C8 antibody binds more strongly to an analog form of natural Aβ in which aspartic acid at positions 1 and 7 is replaced with iso-aspartic acid. These results show that efficacy in vivo is due to direct antibody mediated clearance of the plaques within the CNS, and that the ex vivo assay is predictive of in vivo efficacy.

The same assay has been used to test clearing of an antibody against a fragment of synuclein referred to as NAC. Synuclein has been shown to be an amyloid plaque-associated protein. An antibody to NAC was contacted with a brain tissue sample containing amyloid plaques, an microglial cells, as before. Rabbit serum was used as a control. Subsequent monitoring showed a marked reduction in the number and size of plaques indicative of clearing activity of the antibody.

TABLE 17

The ex vivo assay as predictor of in vivo efficacy.

| Antibody | Isotype | Avidity for aggregated Aβ (pM) | Binding to β-amyloid plaques | Ex vivo efficacy | In vivo efficacy |
|---|---|---|---|---|---|
| monoclonal | | | | | |
| 3D6 | IgG2b | 470 | + | + | + |
| 10D5 | IgG1 | 43 | + | + | + |
| 16C11 | IgG1 | 90 | – | – | – |
| 21F12 | IgG2a | 500 | – | – | – |
| TM2a | IgG1 | — | – | – | – |
| polyclonal | | | | | |
| 1-42 | mix | 600 | + | + | + |

Confocal microscopy was used to confirm that Aβ was internalized during the course of the ex vivo assay. In the presence of control antibodies, the exogenous microglial cells remained in a confocal plane above the tissue, there were no phagocytic vesicles containing Aβ, and the plaques remained intact within the section. In the presence of 10D5, nearly all plaque material was contained in vesicles within the exogenous microglial cells. To determine the fate of the internalized peptide, 10D5 treated cultures were extracted with 8M urea at various time-points, and examined by Western blot analysis. At the one hour time point, when no phagocytosis had yet occurred, reaction with a polyclonal antibody against Aβ revealed a strong 4 kD band (corresponding to the A13 peptide). Aβ immunoreactivity decreased at day 1 and was absent by day 3. Thus, antibody-mediated. phagocytosis of Aβ leads to its degradation.

To determine if phagocytosis in the ex vivo assay was Fc-mediated, F(ab')2 fragments of the anti-Aβ antibody 3D6 were prepared. Although the F(ab')2 fragments retained their full ability to react with plaques, they were unable to trigger phagocytosis by microglial cells. In addition, phagocytosis with the whole antibody could be blocked by a reagent against murine Fc receptors (anti-CD16/32). These data indicate that in vivo clearance of Aβ occurs through Fc-receptor mediated phagocytosis.

XV: Passage of Antibodies Through Blood Brain Barrier

This example determines the concentration of antibody delivered to the brain following intravenous injection into a peripheral tissue of either normal or PDAPP mice. PDAPP or control normal mice were perfused with 0.9% NaCl. Brain regions (hippocampus or cortex) were dissected and rapidly frozen. Brain were homogenized in 0. 1% triton+ protease inhibitors. Immunoglobulin was detected in the extracts by ELISA. Fab'2 Goat Anti-mouse IgG were coated onto an RIA plate as capture reagent. The serum or the brain extracts were incubated for 1 hr. The isotypes were detected with anti-mouse IgG1-HRP or IgG2a-HRP or IgG2b-HRP (Caltag). Antibodies, regardless of isotype, were present in the CNS at a concentration that is 1:1000 that found in the blood. For example, when the concentration of IgG1 was three times that of IgG2a in the blood, it was three times IgG2a in the brain as well, both being present at 0. 1% of their respective levels in the blood. This result was observed in both transgenic and nontransgenic mice-so the PDAPP does not have a uniquely leak blood brain barrier.

XVI: Therapeutic Efficacy of an Aβ Peptide in MAP Configuration

A therapeutic adjuvant/immunogen efficacy study was performed in 9–10.5 month old male and female heterozygous PDAPP transgenic mice to test the efficacy of a fusion protein comprising Aβ1–7 in tetrameric MAP configuration as described above. The duration of the study was 25 weeks with 29–40 animals per treatment group; therefore the animals were 15–16.5 months old at termination. The methodology used in this study is the same as that in the therapeutic study of different adjuvants in Example VIII above. The treatment groups are identified in Table 18 below.

TABLE 18

|  | Adjuvant | Immunogen | Dilution Buffer | Administration |
|---|---|---|---|---|
| Group 1: | CFA/IFA | MAP(Aβ 1-7:TT) (100 μg) | PBS | IP (400 μl) |
| Group 2: | QS21 | AN1792-GCS (75 μg) | PBS | SC (250 μl) |
| Group 3: | PBS | — | — | SC (250 μl) |

Table abbreviations: MAP - multi-antigenic peptide; TT - tetanus toxoid t-cell epitope (830–844); SC - subcutaneous; IP - intraperitoneally; PBS - phosphate buffered saline; GCS is a glycine/citrate/sucrose formulation.

The immunization schedule was identical for all of the treatment groups. The mice were injected on weeks 0, 2, 4, 8, 12, 16, 20, 24, with bleeds on week 3, 5, 9, 13, 17, 21 and 25. Groups 1, 2, 3, 4, and 6 received eight injections Groups 2 and 3, QS21/AN1792 and PBS respectively, served as the positive and negative controls for this study.

The titers were determined by the anti-Aβ antibody titer assay.

Group 1, CFA/IFA:MAP(Aβ1–7:TT) group, had low titer levels. The peak GMT reached was only 1,200 at 13 weeks, falling to a GMT of 600 by week 25. There were 3 of the 30 mice that did not raise any titer and another 7 mice that did not exceed a titer of 400 by the end of the study.

Group 2, the QS21/AN1792 control group, reached its peak titer at 17 weeks with a GMT of 16,000. The titer then fell over the next 8 weeks to finish with a GMT of 8,700. One animal in this group failed to raise a titer over the entire course of the experiment.

Group 3, the PBS alone group, had no titers.

Both treatment groups showed a significant lowing in cortical Aβ levels as compared to the PBS control group (see Table 19). The CFA/IFA:MAP(Aβ1–7) group, significantly lowered Aβ as compared to the PBS control group in spite of the relatively low titers of anti-Aβ antibodies.

TABLE 19

|  | Cortical Aβ levels | | |
|---|---|---|---|
|  | PBS | MAP | QS-21 |
| MEDIAN (ng/g tissue) | 7,335 | 3,692 | 2,389 |
| RANGE (ng/g tissue) | 550–18,358 | 240–10,782 | 210–11,167 |
| p value | — | 0.0003 | <0.0001 |
| N | 38 | 30 | 34 |

In conclusion, the Aβ1–7MAP immunogen is effective in inducing a sufficient immune response significantly to retard Aβ deposition in the cortex.

XVII. Epitope Mapping of Immunogenic Response to Aβ in Monkeys

This example analyzes the response of a primate to immunization with AN1792 (i.e., Aβ1–42). Eleven groups of monkeys (4/sex/group) were immunized with AN1792 (75 or 300 μg/dose) in combination with QS-21 adjuvant (50 or 100 μg/dose) or 5% sterile dextrose in water (D5W, control group). All animals received IM injections on one of three injection schedules as shown in Table 20 for a total of 4, 5 or 8 doses. Serum samples (from 4 monkeys/sex/group) collected on Day 175 of the study and CSF samples (from 3 monkeys/sex/group) collected on Day 176 of the study (at the 6 month necropsy) were evaluated for their ability to bind to Aβ1–40 peptide and APP.

TABLE 20

| Group Assignments and Dose Levels | | | | | |
|---|---|---|---|---|---|
| Group No. | Schedule[a] | # Monkeys (M/F) | AN1792 Dose (μg/dose) | QS-21 Dose (μg/dose) | Dose Route |
| 1[b] | 1 | 4/4 | 0 | 0 | IM |
| 2 | 1 | 4/4 | Vehicle[c] | 50 | IM |
| 3 | 1 | 4/4 | Vehicle | 100 | IM |
| 4 | 1 | 4/4 | 75 | 50 | IM |
| 5 | 1 | 4/4 | 300 | 50 | IM |
| 6 | 1 | 4/4 | 75 | 100 | IM |
| 7 | 1 | 4/4 | 300 | 100 | IM |
| 8 | 2 | 4/4 | 75 | 100 | IM |
| 9 | 2 | 4/4 | 300 | 100 | IM |
| 10 | 3 | 4/4 | 75 | 100 | IM |
| 11 | 3 | 4/4 | 300 | 100 | IM |

[a]. Schedule 1, Dose Days 1, 15, 29, 57, 85, 113, 141, 169; Schedule 2, Dose Days 1, 29, 57, 113, 169; Schedule 3, Dose Days 1, 43, 85, 169
[b]. D5W injection control group
[c]. Vehicle consists of the glycine/citrate/sucrose buffer which is the excipient for AN1792.

The exact array of linear peptides recognized by the antibodies in the serum samples from animals immunized with AN1792 was determined by an ELISA that measured the binding of these antibodies to overlapping peptides that covered the entire Aβ1–42 sequence. Biotinylated peptides with partial sequences of AN1792 were obtained from Chiron Technologies as 10 amino acid peptides with an overlap of 9 residues and a step of one residue per peptide (synthesis No. 5366, No. 5331 and No. 5814). The first 32 peptides (from the eight amino acid position upstream of the N-terminal of AN1792 down to the twenty-fourth amino acid of AN1792) are biotinylated on the C-terminal with a linker of GGK. The last 10 peptides (repeating the thirty-second peptide from the previous series) are biotinylated on the N-terminal with a linker consisting of EGEG (SEQ ID NO:76). The lyophilized biotinylated peptides were dissolved at a concentration of 5 mM in DMSO. These peptide stocks were diluted to 5 μM in TTBS (0.05% Tween 20,25 mM Tris HCl, 137 mM NaCl, 5.1 mM KCl, pH=7.5). 100 μl aliquots of this 5 μM solution were added in duplicate to streptavidin pre-coated 96-well plates (Pierce). Plates were incubated for one hour at room temperature, then washed four times with TTBS. Serum samples were diluted in specimen diluent without azide to normalize titers, and 100 μl was added per well. These plates were incubated one hour at room temperature and then washed four times with TTBS. HRP-conjugated goat anti-human antibody (Jackson ImmunoResearch) was diluted 1:10,000 in specimen diluent without azide and 100 μl was added per well. The plates were again incubated and washed. To develop the color reaction, TMB (Pierce), was added at 100 μl per well and incubated for 15 min prior to the addition of 30 μl of 2 N $H_2SO_4$ to stop the reaction.

The optical density was measured at 450 nm on a Vmax or Spectramax colorimetric plate reader.

Immunization with AN1792 resulted in the production of antibodies in 100% of the animals in all of the dose groups by Day 175. Mean titers in the groups ranged from 14596–56084. There was a trend for titers to be higher within an immunization schedule in the presence of higher antigen and/or higher adjuvant concentration, but no statistically significant differences could be demonstrated due to the high variability in individual animal responses to the immunizations.

Sera which were positive for antibodies to AN1792 were also positive for antibodies to Aβ1–40. Mean titers in the groups ranged from 36867–165991, and as for anti-AN1792 titers, showed no statistically significant differences between groups at Day 175. Binding to AN1792 showed a highly positive correlation (Spearman r=0.8671) with binding to Aβ1–40.

Of the 48 monkeys immunized on various schedules with AN1792, 33 yielded CSF samples of adequate volume and quality for analysis. Thirty-two (97%) of these monkeys had positive titers to AN1792. Titers ranged from 2–246, with a mean of 49.44±21.34. CSF anti-AN1792 levels were 0.18±0.11% of what was measured in the serum and demonstrated a highly positive correlation (Spearman r=0.7840) with serum titers. No differences were seen across groups or between sexes in the percentage of antibody in the CSF. The level of antibody in the CSF is consistent with the passive transfer of peripherally generated antibody across the blood-brain-barrier into the central nervous system.

Testing of a subset of anti-AN1792 positive CSF samples demonstrated that, like the antibody in serum samples, antibody in the CSF cross-reacts with Aβ1–40. Titers to Aβ1–40 showed a high correlation (Spearman r=0.9634) to their respective AN1792 titers. Testing of a subset of CSF samples with the highest titers to AN1792 showed no binding to APP, as for the serum antibodies.

Figure 19:
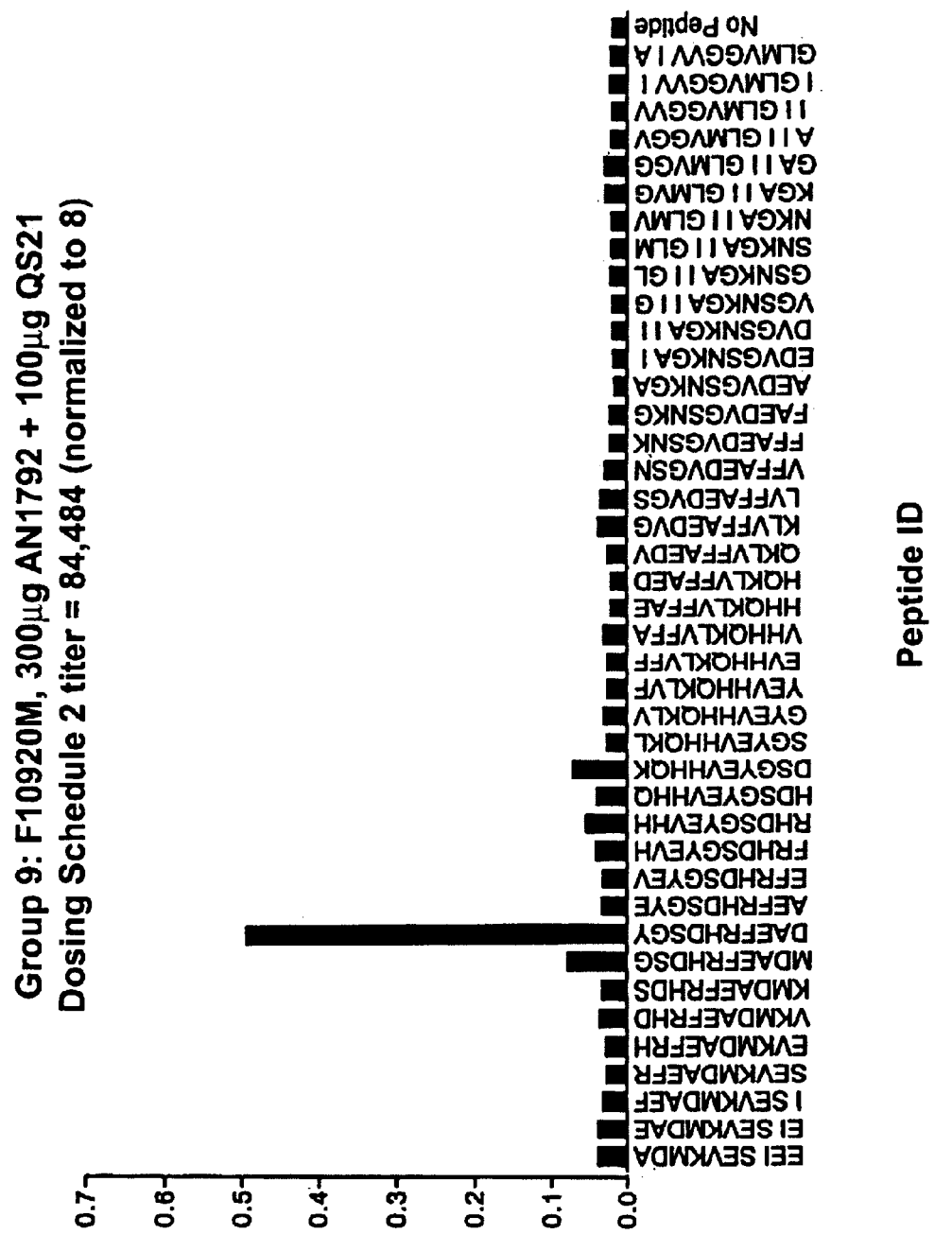
FIG. 19: Epitope Map: Restricted N-terminal Response. Day 175 serum from cynomolgus monkeys was tested by ELISA against a series of 10-mer overlapping peptides (SEQ ID NOS:1–41) covering the complete AN1792 sequence. Animal number F10920M shows a representative N-terminal restricted response to the peptide DAEFRHDSGY (SEQ ID NO:9) which covers amino acids 1–10 of the AN1792 peptide which was used as immunizing antigen.

When sera from Day 175 was tested against a series of overlapping 10-mer peptides, antibodies from all of the monkeys bound to the peptide whose sequence covered amino acids 1–10 of the AN1792 peptide (amino acids 653–672 of APP). In some animals, this was the only peptide to which binding could be measured (see FIG. 19).

Figure 20:
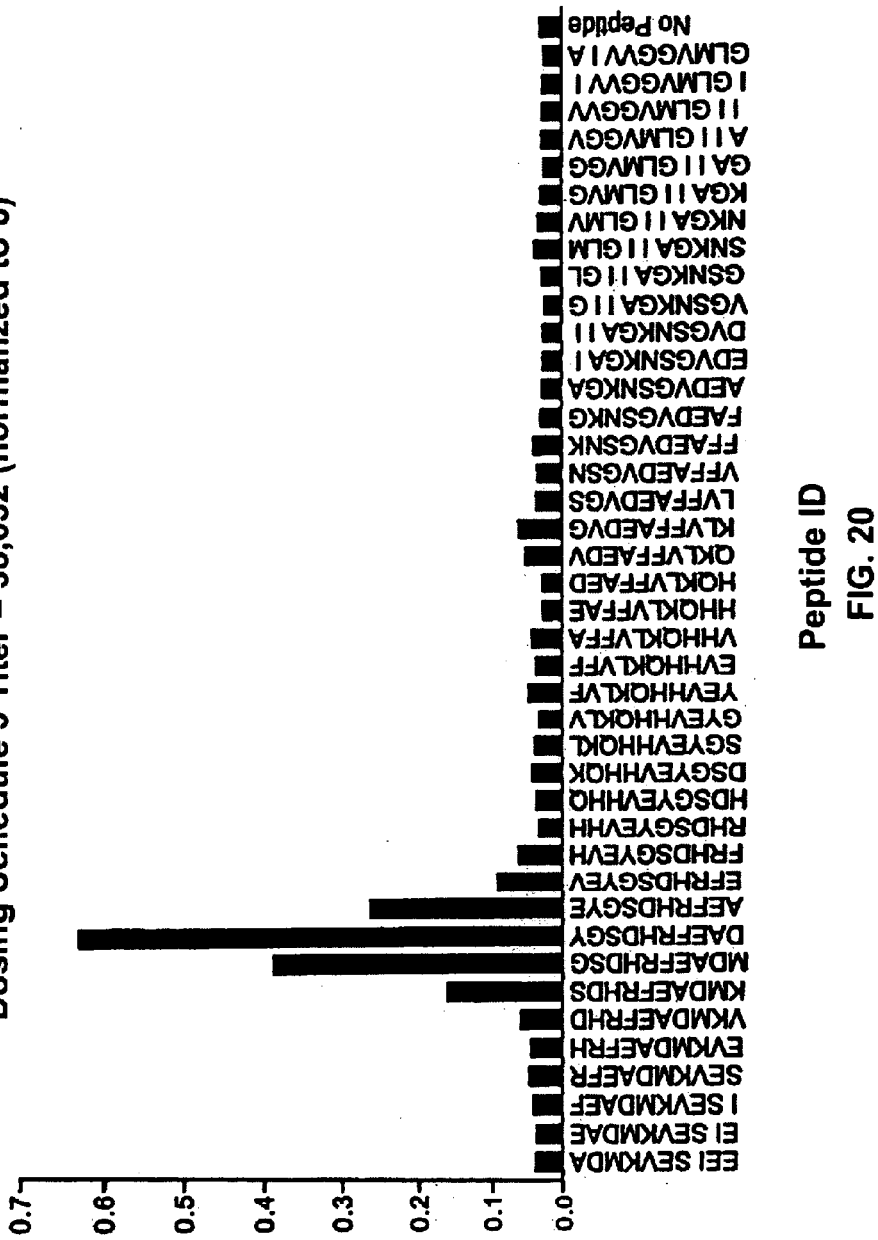
FIG. 20: Epitope Map: Non-restricted N-terminal response. Day 175 serum from cynomolgus monkeys was tested by ELISA against a series of 10-mer overlapping peptides (SEQ ID NOS:1–41) covering the complete AN1792 sequence. Animal number F10975F shows a representative non-restricted N-terminal response. Reactivity is seen against the two peptides N-terminal and one peptide C-terminal to the peptide DAEFRHDSGY (SEQ ID NO:9) which covers amino acids 1–10 of the AN1792 peptide.

In other animals, other reactivities could be measured, but in all cases the reactivity to the N-terminal peptide sequence was the predominant one. The additional reactivities fell into two groups. First and most common, was the binding to peptides centering around the N-terminal 1–10 AN1792 peptide (FIG. 20). Binding of this type was directed to the peptides covering amino acids -1–8, -1–9, and 2–11 of the AN1792 peptide. These reactivities, combined with that to the 1–10 peptide, represent the overwhelming majority of reactivity in all animals. Epitope mapping of individual animals over time indicates that the antibody reactivity to the 1–10 peptide proceeds the spread to the adjacent peptides. This demonstrates a strong biasing of the immune response to the N-terminus of the AN1792 peptide with its free terminal aspartic acid residue. The second minor detectable activity in some animals was binding to peptides located C-terminally to the major area and centered around peptides covering amino acids 7–16, 11–20 and 16–25 of the AN1792 peptide . These reactivities were seen in only 10–30% of the monkeys.

Variability in response between different animals (e.g., whether amino acids 1–10 were the exclusive or predominant reactive epitope) did not correlate with antigen/adjuvant dose, dosing schedule, or antibody titer, and is probably a reflection of each individual animal's genetic make-up.

XVIII. Prevention and Treatment of Human Subjects

A single-dose phase I trial is performed to determine safety in humans. A therapeutic agent is administered in increasing dosages to different patients starting from about 0.01 the level of presumed efficacy, and increasing by a factor of three until a level of about 10 times the effective mouse dosage is reached.

A phase II trial is performed to determine therapeutic efficacy. Patients with early to mid Alzheimer's Disease defined using Alzheimer's disease and Related Disorders Association (ADRDA) criteria for probable Aβ are selected. Suitable patients score in the 12–26 range on the Mini-Mental State Exam (MMSE). Other selection criteria are that patients are likely to survive the duration of the study and lack complicating issues such as use of concomitant medications that may interfere. Baseline evaluations of patient function are made using classic psychometric measures, such as the MMSE, and the ADAS, which is a comprehensive scale for evaluating patients with Alzheimer's Disease status and function. These psychometric scales provide a measure of progression of the Alzheimer's condition. Suitable qualitative life scales can also be used to monitor treatment. Disease progression can also be monitored by MRI. Blood profiles of patients can also be monitored including assays of immunogen-specific antibodies and T-cells responses.

Following baseline measures, patients begin receiving treatment. They are randomized and treated with either therapeutic agent or placebo in a blinded fashion. Patients are monitored at least every six months. Efficacy is determined by a significant reduction in progression of a treatment group relative to a placebo group.

A second phase 11 trial is performed to evaluate conversion of patients from non-Alzheimer's Disease early memory loss, sometimes referred to as age-associated memory impairment (AAMI) or mild cognitive impairment (MCI), to probable Alzheimer's disease as defined as by ADRDA criteria. Patients with high risk for conversion to Alzheimer's Disease are selected from a non-clinical population by screening reference populations for early signs of memory loss or other difficulties associated with pre-Alzheimer's symptomatology, a family history of Alzheimer's Disease, genetic risk factors, age, sex, and other features found to predict high-risk for Alzheimer's Disease. Baseline scores on suitable metrics including the MMSE and the ADAS together with other metrics designed to evaluate a more normal population are collected. These patient populations are divided into suitable groups with placebo comparison against dosing alternatives with the agent. These patient populations are followed at intervals of about six months, and the endpoint for each patient is whether or not he or she converts to probable Alzheimer's Disease as defined by ADRDA criteria at the end of the observation.

XIX. General Materials and Methods

1. Measurement of Antibody Titers

Mice were bled by making a small nick in the tail vein and collecting about 200 μl of blood into a microfuge tube. Guinea pigs were bled by first shaving the back hock area and then using an 18 gauge needle to nick the metatarsal vein and collecting the blood into microfuge tubes. Blood was allowed to clot for one hr at room temperature (RT), vortexed, then centrifuged at 14,000 xg for 10 min to separate the clot from the serum. Serum was then transferred to a clean microfuge tube and stored at 4° C. until titered.

Antibody titers were measured by ELISA. 96-well microtiter plates (Costar EIA plates) were coated with 100 μl of a solution containing either 10 μg/ml either Aβ42 or SAPP or other antigens as noted in each of the individual reports in Well Coating Buffer (0.1 M sodium phosphate, pH 8.5, 0.1% sodium azide) and held overnight at RT. The wells were aspirated and sera were added to the wells starting at a 1/100 dilution in Specimen Diluent (0.014 M sodium phosphate, pH 7.4, 0.15 M NaCl, 0.6% bovine serum albumin, 0.05% thimerosal). Seven serial dilutions of the samples were made directly in the plates in three-fold steps to reach a final dilution of 1/218,700. The dilutions were incubated in the coated-plate wells for one hr at RT. The plates were then washed four times with PBS containing 0.05% Tween 20. The second antibody, a goat anti-mouse Ig conjugated to horseradish peroxidase (obtained from Boehringer Mannheim), was added to the wells as 100 µl of a 1/3000 dilution in Specimen Diluent and incubated for one hr at RT. Plates were again washed four times in PBS, Tween 20. To develop the chromogen, 100 µl of Slow TMB (3,3',5,5'-tetramethyl benzidine obtained from Pierce Chemicals) was added to each well and incubated for 15 min at RT. The reaction was stopped by the addition of 25 µl of 2 M $H_2SO_4$. The color intensity was then read on a Molecular Devices Vmax at (450 nm–650 nm).

Titers were defined as the reciprocal of the dilution of serum giving one half the maximum OD. Maximal OD was generally taken from an initial 1/100 dilution, except in cases with very high titers, in which case a higher initial dilution was necessary to establish the maximal OD. If the 50% point fell between two dilutions, a linear extrapolation was made to calculate the final titer. To calculate geometric mean antibody titers, titers less than 100 were arbitrarily assigned a titer value of 25.

2. Lymphocyte proliferation assay

Mice were anesthetized with isoflurane. Spleens were removed and rinsed twice with 5 ml PBS containing 10% heat-inactivated fetal bovine serum (PBS-FBS) and then homogenized in a 50° Centricon unit (Dako A/S, Denmark) in 1.5 ml PBS-FBS for 10 sec at 100 rpm in a Medimachine (Dako) followed by filtration through a 100 micron pore size nylon mesh. Splenocytes were washed once with 15 ml PBS-FBS, then pelleted by centrifugation at 200 ×g for 5 min. Red blood cells were lysed by resuspending the pellet in 5 mL buffer containing 0.15 M NH4Cl, 1 M KHCO3, 0.1 M NaEDTA, pH 7.4 for five min at RT. Leukocytes were then washed as above. Freshly isolated spleen cells (105 cells per well) were cultured in triplicate sets in 96-well U-bottomed tissue culture-treated microtiter plates (Coming, Cambridge, Mass.) in RPMI1640 medium (JRH Biosciences, Lenexa, Kans.) supplemented with 2.05 mM L glutamine, 1% Penicillin/Streptomycin, and 10% heat-inactivated FBS, for 96 hr at 37° C. Various Aβ peptides, Aβ1–16, Aβ1–40, Aβ1–42 or Aβ40–1 reverse sequence protein were also added at doses ranging from 5 to 0.18 micromolar in four steps. Cells in control wells were cultured with Concanavalin A (Con A) (Sigma, cat. # C-5275, at 1 microgram/ml) without added protein. Cells were pulsed for the final 24 hr with 3H-thymidine (1 µCi/well obtained from Amersham Corp., Arlington Heights Ill.). Cells were then harvested onto UniFilter plates and counted in a Top Count Microplate Scintillation Counter (Packard Instruments, Downers Grove, Ill.). Results are expressed as counts per minute (cpm) of radioactivity incorporated into insoluble macromolecules.

4. Brain Tissue Preparation

After euthanasia, the brains were removed and one hemisphere was prepared for immunohistochemical analysis, while three brain regions (hippocampus, cortex and cerebellum) were dissected from the other hemisphere and used to measure the concentration of various Aβ proteins and APP forms using specific ELISAs (Johnson-Wood et al., supra).

Tissues destined for ELISAs were homogenized in 10 volumes of ice-cold guanidine buffer (5.0 M guanidine-HCl, 50 mM Tris-HCl, pH 8.0). The homogenates were mixed by gentle agitation using an Adams Nutator (Fisher) for three to four hr at RT, then stored at −20° C. prior to quantitation of Aβ and APP. Previous experiments had shown that the analytes were stable under this storage condition, and that synthetic Aβ protein (Bachem) could be quantitatively recovered when spiked into homogenates of control brain tissue from mouse litterrnates (Johnson-Wood et al., supra).

5. Measurement of Aβ Levels

The brain homogenates were diluted 1:10 with ice cold Casein Diluent (0.25% casein, PBS, 0.05% sodium azide, 20 µg/ml aprotinin, 5 mM EDTA pH 8.0, 10 µg/ml leupeptin) and then centrifuged at 16,000 ×g for 20 min at 4° C. The synthetic Aβ protein standards (1–42 amino acids) and the APP standards were prepared to include 0.5 M guanidine and 0.1% bovine serum albumin (BSA) in the final composition. The "total" Aβ sandwich ELISA utilizes monoclonal antibody (mAb) 266, specific for amino acids 13–28 of Aβ (Seubert, et al.), as the capture antibody, and biotinylated mAb 3D6, specific for amino acids 1–5 of Aβ (Johnson-Wood, et al.), as the reporter antibody. The 3D6 mAb does not recognize secreted APP or full-length APP, but detects only Aβ species with an amino-terminal aspartic acid. The cell line producing the antibody 3D6 has the ATCC accession number PTA-5130, having been deposited on Apr. 8, 2003. This assay has a lower limit of sensitivity of 50 ng/ml (II nM) and shows no cross-reactivity to the endogenous murine Aβ protein at concentrations up to 1 ng/ml (Johnson-Wood et al., supra).

The Aβ1–42 specific sandwich ELISA employs mAβ 21F12, specific for amino acids 33–42 of Aβ (Johnson-Wood, et al.), as the capture antibody. Biotinylated mAβ 3D6 is also the reporter antibody in this assay which has a lower limit of sensitivity of about 125 µg/ml (28 µM, Johnson-Wood et al.). For the Aβ ELISAs, 100 µl of either mAβ 266 (at 10 µg/ml) or mAβ 21F12 at (5 µg/ml) was coated into the wells of 96-well immunoassay plates (Costar) by overnight incubation at RT. The solution was removed by aspiration and the wells were blocked by the addition of 200 µl of 0.25% human serum albumin in PBS buffer for at least 1 hr at RT. Blocking solution was removed and the plates were stored desiccated at 4° C. until used. The plates were rehydrated with Wash Buffer [Tris-buffered saline (0.15 M NaCl, 0.01 M Tris-HCl, pH 7.5), plus 0.05% Tween 20] prior to use. The samples and standards were added in triplicate aliquots of 100 µl per well and then incubated overnight at 4° C. The plates were washed at least three times with Wash Buffer between each step of the assay. The biotinylated mAβ3D6, diluted to 0.5 µg/ml in Casein Assay Buffer (0.25% casein, PBS, 0.05% Tween 20, pH 7.4), was added and incubated in the wells for 1 hr at RT. An avidin-horseradish peroxidase conjugate, (Avidin-HRP obtained from Vector, Burlingame, Calif.), diluted 1:4000 in Casein Assay Buffer, was added to the wells for 1 hr at RT. The colorimetric substrate, Slow TMB-ELISA (Pierce), was added and allowed to react for 15 minutes at RT, after which the enzymatic reaction was stopped by the addition of 25 µl 2 N H2SO4. The reaction product was quantified using a Molecular Devices Vmax measuring the difference in absorbance at 450 nm and 650 nm.

6. Measurement of APP Levels

Two different APP assays were utilized. The first, designated APP-α/FL, recognizes both APP-alpha (α) and full-length (FL) forms of APP. The second assay is specific for APP-α. The APP-α/FL assay recognizes secreted APP including the first 12 amino acids of Aβ. Since the reporter antibody (2H3) is not specific to the α-clip-site, occurring between amino acids 612–613 of APP695 (Esch et al., Science 248, 1122–1124 (1990)); this assay also recognizes full length APP (APP-FL). Preliminary experiments using immobilized APP antibodies to the cytoplasmic tail of APP-FL to deplete brain homogenates of APP-FL suggest that approximately 30–40% of the APP-α/FL APP is FL (data not shown). The capture antibody for both the APP-α/FL and APP-α assays is mAb 8E5, raised against amino acids 444 to 592 of the APP695 form (Games et al., supra). The reporter mAb for the APP-α/FL assay is mAb 2H3, specific for amino acids 597–608 of APP695 (Johnson-Wood et al., supra) and the reporter antibody for the APP-α assay is a biotinylated derivative of mAb 16H9, raised to amino acids 605 to 611 of APP. The lower limit of sensitivity of the APP-αFL assay is about 11 ng/ml (150 pM) (Johnson-Wood et al.) and that of the APP-α specific assay is 22 ng/ml (0.3 nM). For both APP assays, mAb 8E5 was coated onto the wells of 96-well EIA plates as described above for mAb 266. Purified, recombinant secreted APP-α was used as the reference standard for the APP-α assay and the APP-α/FL assay (Esch et al., supra). The brain homogenate samples in 5 M guanidine were diluted 1:10 in ELISA Specimen Diluent (0.014 M phosphate buffer, pH 7.4, 0.6% bovine serum albumin, 0.05% thimerosal, 0.5 M NaCl, 0.1% NP40). They were then diluted 1:4 in Specimen Diluent containing 0.5 M guanidine. Diluted homogenates were then centrifuged at 16,000×g for 15 seconds at RT. The APP standards and samples were added to the plate in duplicate aliquots and incubated for 1.5 hr at RT. The biotinylated reporter antibody 2H3 or 16H9 was incubated with samples for 1 hr at RT. Streptavidin-alkaline phosphatase (Boehringer Mannheim), diluted 1:1000 in specimen diluent, was incubated in the wells for 1 hr at RT. The fluorescent substrate 4-methyl-umbellipheryl-phosphate was added for a 30-min RT incubation and the plates were read on a Cytofluor tm 2350 fluorimeter (Millipore) at 365 nm excitation and 450 nm emission.

7. Immunohistochemistry

Brains were fixed for three days at 40C in 4% paraformaldehyde in PBS and then stored from one to seven days at 4° C. in 1% paraformaldehyde, PBS until sectioned. Forty-micron-thick coronal sections were cut on a vibratome at RT and stored in cryoprotectant (30% glycerol, 30% ethylene glycol in phosphate buffer) at −20° C. prior to immunohistochemical processing. For each brain, six sections at the level of the dorsal hippocampus, each separated by consecutive 240 μm intervals, were incubated overnight with one of the following antibodies: (1) a biotinylated anti-Aβ (mAb, 3D6, specific for human Aβ) diluted to a concentration of 2 μg/ml in PBS and 1% horse serum; or (2) a biotinylated mAb specific for human APP, 8E5, diluted to a concentration of 3 μg/ml in PBS and 1.0% horse serum; or (3) a mAb specific for glial fibrillary acidic protein (GFAP; Sigma Chemical Co.) diluted 1:500 with 0.25% Triton X-100 and 1% horse serum, in Tris-buffered saline, pH 7.4 (TBS); or (4) a mAb specific for CD 11 b, MAC-1 antigen, (Chemicon International) diluted 1:100 with 0.25% Triton X-100 and 1% rabbit serum in TBS; or (5) a mAb specific for MHC II antigen, (Pharmingen) diluted 1:100 with 0.25% Triton X-100 and 1% rabbit serum in TBS; or (6) a rat mAb specific for CD 43 (Pharmingen) diluted 1:100 with 1% rabbit serum in PBS or (7) a rat Aβ specific for CD 45RA (Pharmingen) diluted 1:100 with 1% rabbit serum in PBS; or (8) a rat monoclonal Aβ specific for CD 45RB (Pharmingen) diluted 1:100 with 1% rabbit serum in PBS; or (9) a rat monoclonal Aβ specific for CD 45 (Pharmingen) diluted 1:100 with 1% rabbit serum in PBS; or (10) a biotinylated polyclonal hamster Aβ specific for CD3e (Pharmingen) diluted 1:100 with 1% rabbit serum in PBS or (11) a rat mAb specific for CD3 (Serotec) diluted 1:200 with 1% rabbit serum in PBS; or with (12) a solution of PBS lacking a primary antibody containing 1% normal horse serum.

Sections reacted with antibody solutions listed in 1,2 and 6–12 above were pretreated with 1.0% Triton X-100, 0.4% hydrogen peroxide in PBS for 20 min at RT to block endogenous peroxidase. They were next incubated overnight at 4° C. with primary antibody. Sections reacted with 3D6 or 8E5 or CD3e mAbs were then reacted for one hr at RT with a horseradish peroxidase-avidin-biotin-complex with kit components "A" and "B" diluted 1:75 in PBS (Vector Elite Standard Kit, Vector Labs, Burlingame, Calif.). Sections reacted with antibodies specific for CD 45RA, CD 45RB, CD 45, CD3 and the PBS solution devoid of primary antibody were incubated for 1 hour at RT with biotinylated anti-rat IgG (Vector) diluted 1:75 in PBS or biotinylated anti-mouse IgG (Vector) diluted 1:75 in PBS, respectively. Sections were then reacted for one hr at RT with a horseradish peroxidase-avidin-biotin-complex with kit components "A" and "B" diluted 1:75 in PBS (Vector Elite Standard Kit, Vector Labs, Burlingamne, Calif.).

Sections were developed in 0.01% hydrogen peroxide, 0.05% 3,3'-diaminobenzidine (DAB) at RT. Sections destined for incubation with the GFAP-, MAC-1- AND MHC II-specific antibodies were pretreated with 0.6% hydrogen peroxide at RT to block endogenous peroxidase then incubated overnight with the primary antibody at 4° C. Sections reacted with the GFAP antibody were incubated for 1 hr at RT with biotinylated anti-mouse IgG made in horse (Vector Laboratories; Vectastain Elite ABC Kit) diluted 1:200 with TBS. The sections were next reacted for one hr with an avidin-biotin-peroxidase complex (Vector Laboratories; Vectastain Elite ABC Kit) diluted 1:1000 with TBS. Sections incubated with the MAC-1-or MHC II-specific monoclonal antibody as the primary antibody were subsequently reacted for 1 hr at RT with biotinylated anti-rat IgG made in rabbit diluted 1:200 with TBS, followed by incubation for one hr with avidin-biotin-peroxidase complex diluted 1:1000 with TBS. Sections incubated with GFAP-, MAC-1- and MHC II-specific antibodies were then visualized by treatment at RT with 0.05% DAB, 0.01% hydrogen peroxide, 0.04% nickel chloride, TBS for 4 and 11 min, respectively.

Immunolabeled sections were mounted on glass slides (VWR, Superfrost slides), air dried overnight, dipped in Propar (Anatech) and overlaid with coverslips using Permount (Fisher) as the mounting medium.

To counterstain Aβ plaques, a subset of the GFAP-positive sections were mounted on Superfrost slides and incubated in aqueous 1% Thioflavin S (Sigma) for 7 min following immunohistochemical processing. Sections were then dehydrated and cleared in Propar, then overlaid with coverslips mounted with Permount.

8. Image Analysis

A Videometric 150 Image Analysis System (Oncor, Inc., Gaithersburg, Md.) linked to a Nikon Microphot-FX microscope through a CCD video camera and a Sony Trinitron monitor was used for quantification of the immunoreactive slides. The image of the section was stored in a video buffer and a color-and saturation-based threshold was determined to select and calculate the total pixel area occupied by the immunolabeled structures. For each section, the hippocampus was manually outlined and the total pixel area occupied by the hippocampus was calculated. The percent amyloid burden was measured as: (the fraction of the hippocampal area containing Aβ deposits immunoreactive with mAb 3D6)×100. Similarly, the percent neuritic burden was measured as: (the fraction of the hippocampal area containing dystrophic neurites reactive with monoclonal antibody 8E5) ×100. The C-Imaging System (Compix, Inc., Cranberry Township, Pa.) operating the Simple 32 Software Application program was linked to a Nikon Microphot-FX microscope through an Optronics camera and used to quantitate the percentage of the retrospenial cortex occupied by GFAP-positive astrocytes and MAC-1-and MHC II-positive microglia. The image of the immunoreacted section was stored in a video buffer and a monochrome-based threshold was determined to select and calculate the total pixel area occupied by immunolabeled cells. For each section, the retrosplenial cortex (RSC) was manually outlined and the total pixel area occupied by the RSC was calculated. The percent astrocytosis was defined as: (the fraction of RSC occupied by GFAP-reactive astrocytes) X 100. Similarly, percent microgliosis was defined as: (the fraction of the RSC occupied by MAC-1- or MHC II-reactive microglia) X 100.

For all image analyses, six sections at the level of the dorsal hippocampus, each separated by consecutive 240 μm intervals, were quantitated for each animal. In all cases, the treatment status of the animals was unknown to the observer.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

From the foregoing it will be apparent that the invention provides for a number of uses. For example, the invention provides for the use of any of the antibodies to Aβ described above in the treatment, prophylaxis or diagnosis of amyloidogenic disease, or in the manufacture of a medicament or diagnostic composition for use in the same. Likewise, the invention provides for the use of any of the epitopic fragments of Aβ described above for the treatment or prophylaxis of amyloidogenic disease or in the manufacture of a medicament for use in the same.

TABLE 1

TITER AT 50% MAXIMAL O.D.
Aggreated Aβ injected mice

| Age of PDAPP | mouse 100 | mouse 101 | mouse 102 | mouse 103 | mouse 104 | mouse 105 | mouse 106 | mouse 107 | mouse 108 |
|---|---|---|---|---|---|---|---|---|---|
| 4 | 70000 | 150000 | 15000 | 120000 | 1000 | 15000 | 50000 | 80000 | 100000 |
| 6 | 15000 | 65000 | 30000 | 55000 | 300 | 15000 | 15000 | 50000 | 60000 |
| 8 | 20000 | 55000 | 50000 | 50000 | 400 | 15000 | 18000 | 50000 | 60000 |
| 10 | 40000 | 20000 | 60000 | 50000 | 900 | 15000 | 50000 | 20000 | 40000 |
| 12 | 25000 | 30000 | 60000 | 40000 | 2700 | 20000 | 70000 | 25000 | 20000 |

PBS injected mice on both immunogens; at 1/100

| Age of PDAPP | mouse 113 | mouse 114 | mouse 115 | mouse 116 | mouse 117 |
|---|---|---|---|---|---|
| 6 | <4x bkg | <4x bkg | <4x bkg | <4x bkg | <4x bkg |
| 10 | 5x bkg | <4x bkg | <4x bkg | <4x bkg | <4x bkg |
| 12 | <4x bkg | <4x bkg | <4x bkg | <4x bkg | <4x bkg |

What is claimed is:

1. A method of prophylactically or therapeutically treating Alzheimer's disease, comprising administering to the patient an effective dosage of a pharmaceutical composition comprising a humanized or chimeric antibody that specifically binds to an epitope within Aβ1–7, and hereby prophylactically or therapeutically treating the patient.

2. The method of claim 1, wherein the antibody is of human isotype IgG1.

3. The method of any one of the preceding claims, wherein the patient is human.

4. The method of claim 1, wherein the antibody specifically binds to an epitope within residues 1–6 of Aβ.

5. The method of claim 1, wherein the antibody specifically binds to an epitope within residues 1–5 of Aβ.

6. The method of claim 1, wherein the antibody specifically binds to an epitope within residues 3–7 of Aβ.

7. The method of claim 1, wherein the antibody specifically binds to an epitope within residues 1–3 of Aβ.

8. The method of claim 1, wherein the antibody specifically binds to an epitope within residues 14 of Aβ.

9. The method of claim 1, wherein the patient is asymptomatic.

10. The method of claim 1, wherein the patient is under 50.

11. The method of claim 1, wherein the patient has inherited risk factors indicating susceptibility to Alzheimer's disease.

12. The method of claim 1, wherein the patient has no known risk factors for Alzheimer's disease.

13. The method of claim 1, wherein the antibody is a human antibody.

14. The method of claim 1, wherein the antibody is a humanized antibody.

15. The method of claim 1, wherein the antibody is a chimeric antibody.

16. The method of claim 1, wherein the antibody is a polyclonal antibody.

17. The method of claim 1, wherein the antibody is a monoclonal antibody.

18. The method of claim 1, further comprising administering an effective dosage of at least one other antibody that binds to a different epitope of Aβ.

19. The method of claim 1, wherein the isotype of the antibody is IgG1 or IgG4.

20. The method of claim 1, wherein the isotype of the antibody is IgG2 or IgG3.

21. The method of claim 1, wherein the antibody comprises two copies of the same pair of light and heavy chains.

22. The method of claim 1, wherein the dosage of antibody is at least 1 mg/kg body weight of the patient.

23. The method of claim 1, wherein the dosage of antibody is at least 10 mg/kg body weight of the patient.

24. The method of claim 1, wherein the antibody is administered with a carrier.

25. The method of claim 1, wherein the antibody specifically binds to Aβ peptide without binding to full-length amyloid precursor protein (APP).

26. The method of claim 1, wherein the antibody is administered intraperitoneally, orally, subcutaneously, intranasally, intramuscularly, topically or intravenously.

27. The method of claim 1, further comprising monitoring the patient for level of administered antibody in the blood of the patient.

28. The method of claim 1, wherein after administration the antibody binds to an amyloid deposit in the patient and induces a clearing response against the amyloid deposit.

29. The method of claim 28, wherein the clearing response is an Fc receptor mediated phagocytosis response.

30. The method of claim 29, further comprising monitoring the clearing response.

31. The method of claims 1, wherein the antibody is a human antibody to Aβ prepared from B cells from a human immunized with an Aβ peptide.

32. The method of claim 31, wherein the human immunized with Aβ peptide is the patient.

33. The method of claim 1, wherein a single dosage of the antibody is administered on multiple occasions.

34. The method of claim 33, wherein the single dosage is administered once every week, once per every two weeks, once a month, once every 3 to 6 months, or yearly.

35. The method of claim 33 or 34 wherein the occasions occur over a period of at least six months.

36. The method of claim 1, wherein the method further comprises monitoring a response to the administration of the antibody to the patient.

* * * * *

UNITED STATES PATENT AND TRADEMARK OFFICE
CERTIFICATE OF CORRECTION

PATENT NO. : 6,761,888 B1
DATED : July 13, 2004
INVENTOR(S) : Dale B. Schenk et al.

It is certified that error appears in the above-identified patent and that said Letters Patent is hereby corrected as shown below:

Title page,
Item [12], delete "Schenk" and replace it with -- Schenk et al. --
Item [75], Inventors, add the following:
-- Frederique Bard, Pacifica, CA (FR)
   Ted Yednock, Forest Knolls, CA (US) --

Column 105,
Line 14, delete claim 5.
Line 20, claim 8, should read as follows:
Claim 8. The method of claim 1, wherein the antibody specifically binds to an epitope within residues 1-4 of Aβ.

Column 106,
Line 28, delete claim 31.
Line 30, delete claim 32.

Signed and Sealed this

Twenty-third Day of November, 2004

JON W. DUDAS
*Director of the United States Patent and Trademark Office*

SEQUENCE LISTING

<160> NUMBER OF SEQ ID NOS: 77

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:10-mer
      peptidefrom AN1792 sequence (human Abeta42, beta-amyloid peptide)

<400> SEQUENCE: 1

Glu Glu Ile Ser Glu Val Lys Met Asp Ala
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 2

-continued

```
Glu Ile Ser Glu Val Lys Met Asp Ala Glu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 3

Ile Ser Glu Val Lys Met Asp Ala Glu Phe
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 4

Ser Glu Val Lys Met Asp Ala Glu Phe Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 5

Glu Val Lys Met Asp Ala Glu Phe Arg His
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 6

Val Lys Met Asp Ala Glu Phe Arg His Asp
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 7

Lys Met Asp Ala Glu Phe Arg His Asp Ser
1               5                   10

<210> SEQ ID NO 8
<211> LENGTH: 10
<212> TYPE: PRT
<213> ORGANISM: Artificial Sequence
```

```
-continued

<220> FEATURE:
<223> OTHER INFORMATION: Description of Artificial Sequence:10-mer
      peptide from AN1792 sequence (human Abeta42, beta-amyloid peptide)

<400> SEQUENCE: 8

Met Asp Ala Glu Phe Arg His Asp Ser Gly
  1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 9

Asp Ala Glu Phe Arg His Asp Ser Gly Tyr
  1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 10

Ala Glu Phe Arg His Asp Ser Gly Tyr Glu
  1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 11

Glu Phe Arg His Asp Ser Gly Tyr Glu Val
  1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 12

Phe Arg His Asp Ser Gly Tyr Glu Val His
  1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 13

Arg His Asp Ser Gly Tyr Glu Val His His
  1               5                  10
```

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 14

His Asp Ser Gly Tyr Glu Val His His Gln
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 15

Asp Ser Gly Tyr Glu Val His His Gln Lys
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 16

Ser Gly Tyr Glu Val His His Gln Lys Leu
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 17

Gly Tyr Glu Val His His Gln Lys Leu Val
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 18

Tyr Glu Val His His Gln Lys Leu Val Phe
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

```
<400> SEQUENCE: 19

Glu Val His His Gln Lys Leu Val Phe Phe
  1               5                  10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 20

Val His His Gln Lys Leu Val Phe Phe Ala
  1               5                  10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 21

His His Gln Lys Leu Val Phe Phe Ala Glu
  1               5                  10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 22

His Gln Lys Leu Val Phe Phe Ala Glu Asp
  1               5                  10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 23

Gln Lys Leu Val Phe Phe Ala Glu Asp Val
  1               5                  10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 24

Lys Leu Val Phe Phe Ala Glu Asp Val Gly
  1               5                  10

<210> SEQ ID NO 25
<211> LENGTH: 10
<212> TYPE: PRT
```

```
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 25

Leu Val Phe Phe Ala Glu Asp Val Gly Ser
 1               5                  10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 26

Val Phe Phe Ala Glu Asp Val Gly Ser Asn
 1               5                  10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 27

Phe Phe Ala Glu Asp Val Gly Ser Asn Lys
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 28

Phe Ala Glu Asp Val Gly Ser Asn Lys Gly
 1               5                  10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 29

Ala Glu Asp Val Gly Ser Asn Lys Gly Ala
 1               5                  10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 30

Glu Asp Val Gly Ser Asn Lys Gly Ala Ile
 1               5                  10
```

-continued

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 31

Asp Val Gly Ser Asn Lys Gly Ala Ile Ile
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 32

Val Gly Ser Asn Lys Gly Ala Ile Ile Gly
 1               5                  10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 33

Gly Ser Asn Lys Gly Ala Ile Ile Gly Leu
 1               5                  10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 34

Ser Asn Lys Gly Ala Ile Ile Gly Leu Met
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 35

Asn Lys Gly Ala Ile Ile Gly Leu Met Val
 1               5                  10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

```
<400> SEQUENCE: 36

Lys Gly Ala Ile Ile Gly Leu Met Val Gly
 1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 37

Gly Ala Ile Ile Gly Leu Met Val Gly Gly
 1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 38

Ala Ile Ile Gly Leu Met Val Gly Gly Val
 1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 39

Ile Ile Gly Leu Met Val Gly Gly Val Val
 1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 40

Ile Gly Leu Met Val Gly Gly Val Val Ile
 1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence:10-mer
      peptide from AN1792 sequence (human Abeta42, beta-amyloid peptide)

<400> SEQUENCE: 41

Gly Leu Met Val Gly Gly Val Val Ile Ala
 1               5                   10

<210> SEQ ID NO 42
<211> LENGTH: 42
```

```
<212> TYPE: PRT
<213> ORGANISM: Homo sapiens
<220> FEATURE:
<223> OTHER INFORMATION: human Abeta42 beta-amyloid peptide

<400> SEQUENCE: 42

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence:influenza
      hemagglutinin HA-307-319 universal T-cell epitope

<400> SEQUENCE: 43

Pro Lys Tyr Val Lys Gln Asn Thr Leu Lys Leu Ala Thr
 1               5                  10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence:PADRE
      universal T-cell epitope
<221> NAME/KEY: misc_feature
<222> LOCATION: (3)
<223> OTHER INFORMATION: Xaa = Any amino acid

<400> SEQUENCE: 44

Ala Lys Xaa Val Ala Ala Trp Thr Leu Lys Ala Ala Ala
 1               5                  10

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence:malaria CS,
      T3 epitope universal T-cell epitope

<400> SEQUENCE: 45

Glu Lys Lys Ile Ala Lys Met Glu Lys Ala Ser Ser Val Phe Asn Val
 1               5                  10                  15

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence:hepatitis B
      surface antigen HBsAg-19-28 universal T-cell epitope

<400> SEQUENCE: 46

Phe Phe Leu Leu Thr Arg Ile Leu Thr Ile
 1               5                  10

<210> SEQ ID NO 47
<211> LENGTH: 19
<212> TYPE: PRT
```

-continued

```
<213> ORGANISM: Artificial Sequence
<220> FEATURE:
<223> OTHER INFORMATION: Description of Artificial Sequence:heat shock
      protein 65 hsp65-153-171 universal T-cell epitope

<400> SEQUENCE: 47

Asp Gln Ser Ile Gly Asp Leu Ile Ala Glu Ala Met Asp Lys Val Gly
 1               5                  10                  15

Asn Glu Gly

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence:bacille
      Calmette-Guerin universal T-cell epitope

<400> SEQUENCE: 48

Gln Val His Phe Gln Pro Leu Pro Pro Ala Val Val Lys Leu
 1               5                  10

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence:tetanus
      toxoid TT-830-844 universal T-cell epitope

<400> SEQUENCE: 49

Gln Tyr Ile Lys Ala Asn Ser Lys Phe Ile Gly Ile Thr Glu Leu
 1               5                  10                  15

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence:tetanus
      toxoid TT-947-967 universal T-cell epitope

<400> SEQUENCE: 50

Phe Asn Asn Phe Thr Val Ser Phe Trp Leu Arg Val Pro Lys Val Ser
 1               5                  10                  15

Ala Ser His Leu Glu
            20

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence:HIV gp120
      T1 universal T-cell epitope

<400> SEQUENCE: 51

Lys Gln Ile Ile Asn Met Trp Gln Glu Val Gly Lys Ala Met Tyr Ala
 1               5                  10                  15

<210> SEQ ID NO 52
<211> LENGTH: 22
<212> TYPE: PRT
<213> ORGANISM: Artificial Sequence
<220> FEATURE:
<223> OTHER INFORMATION: Description of Artificial Sequence:AN 90549
      Abeta 1-7/tetanus toxoid 830-844
```

```
<400> SEQUENCE: 52

Asp Ala Glu Phe Arg His Asp Gln Tyr Ile Lys Ala Asn Ser Lys Phe
 1               5                  10                  15

Ile Gly Ile Thr Glu Leu
            20

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence:AN 90550
      Abeta 1-7/tetanus toxoid 947-967

<400> SEQUENCE: 53

Asp Ala Glu Phe Arg His Asp Phe Asn Asn Phe Thr Val Ser Phe Trp
 1               5                  10                  15

Leu Arg Val Pro Lys Val Ser Ala Ser His Leu Glu
            20                  25

<210> SEQ ID NO 54
<211> LENGTH: 43
<212> TYPE: PRT
<213> ORGANISM: Artificial Sequence
<220> FEATURE:
<223> OTHER INFORMATION: Description of Artificial Sequence:AN90542
      Abeta 1-7/tetanus toxoid 830-844 + 947-967

<400> SEQUENCE: 54

Asp Ala Glu Phe Arg His Asp Gln Tyr Ile Lys Ala Asn Ser Lys Phe
 1               5                  10                  15

Ile Gly Ile Thr Glu Leu Phe Asn Asn Phe Thr Val Ser Phe Trp Leu
            20                  25                  30

Arg Val Pro Lys Val Ser Ala Ser His Leu Glu
        35                  40

<210> SEQ ID NO 55
<211> LENGTH: 22
<212> TYPE: PRT
<213> ORGANISM: Artificial Sequence
<220> FEATURE:
<223> OTHER INFORMATION: Description of Artificial Sequence:AN 90576
      Abeta 3-9/tetanus toxoid 830-844

<400> SEQUENCE: 55

Glu Phe Arg His Asp Ser Gly Gln Tyr Ile Lys Ala Asn Ser Lys Phe
 1               5                  10                  15

Ile Gly Ile Thr Glu Leu
            20

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence:AN90562
      Abeta 1-7/peptide
<221> NAME/KEY: misc_feature
<222> LOCATION: (3)
<223> OTHER INFORMATION: Xaa = any amino acid

<400> SEQUENCE: 56

Ala Lys Xaa Val Ala Ala Trp Thr Leu Lys Ala Ala Ala Asp Ala Glu
 1               5                  10                  15
```

Phe Arg His Asp
            20

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence:AN90543
      Abeta 1-7 x 3/peptide
<221> NAME/KEY: misc_feature
<222> LOCATION: (24)
<223> OTHER INFORMATION: Xaa = any amino acid

<400> SEQUENCE: 57

Asp Ala Glu Phe Arg His Asp Asp Ala Glu Phe Arg His Asp Asp Ala
 1               5                  10                  15

Glu Phe Arg His Asp Ala Lys Xaa Val Ala Ala Trp Thr Leu Lys Ala
            20                  25                  30

Ala Ala

<210> SEQ ID NO 58
<211> LENGTH: 34
<212> TYPE: PRT
<213> ORGANISM: Artificial Sequence
<220> FEATURE:
<223> OTHER INFORMATION: Description of Artificial Sequence:fusion
      protein with Abeta epitope
<221> NAME/KEY: misc_feature
<222> LOCATION: (3)
<223> OTHER INFORMATION: Xaa = any amino acid

<400> SEQUENCE: 58

Ala Lys Xaa Val Ala Ala Trp Thr Leu Lys Ala Ala Ala Asp Ala Glu
 1               5                  10                  15

Phe Arg His Asp Asp Ala Glu Phe Arg His Asp Ala Glu Phe Arg
            20                  25                  30

His Asp

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence:fusion
      protein with Abeta epitope
<221> NAME/KEY: misc_feature
<222> LOCATION: (10)
<223> OTHER INFORMATION: Xaa = any amino acid

<400> SEQUENCE: 59

Asp Ala Glu Phe Arg His Asp Ala Lys Xaa Val Ala Ala Trp Thr Leu
 1               5                  10                  15

Lys Ala Ala Ala
            20

<210> SEQ ID NO 60
<211> LENGTH: 24
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 60

-continued

```
Asp Ala Glu Phe Arg His Asp Ile Ser Gln Ala Val His Ala Ala His
 1               5                  10                  15

Ala Glu Ile Asn Glu Ala Gly Arg
            20
```

<210> SEQ ID NO 61
<211> LENGTH: 24
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 61

```
Phe Arg His Asp Ser Gly Tyr Ile Ser Gln Ala Val His Ala Ala His
 1               5                  10                  15

Ala Glu Ile Asn Glu Ala Gly Arg
            20
```

<210> SEQ ID NO 62
<211> LENGTH: 24
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 62

```
Glu Phe Arg His Asp Ser Gly Ile Ser Gln Ala Val His Ala Ala His
 1               5                  10                  15

Ala Glu Ile Asn Glu Ala Gly Arg
            20
```

<210> SEQ ID NO 63
<211> LENGTH: 34
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 63

```
Pro Lys Tyr Val Lys Gln Asn Thr Leu Lys Leu Ala Thr Asp Ala Glu
 1               5                  10                  15

Phe Arg His Asp Asp Ala Glu Phe Arg His Asp Asp Ala Glu Phe Arg
            20                  25                  30

His Asp
```

<210> SEQ ID NO 64
<211> LENGTH: 27
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 64

```
Asp Ala Glu Phe Arg His Asp Pro Lys Tyr Val Lys Gln Asn Thr Leu
 1               5                  10                  15

Lys Leu Ala Thr Asp Ala Glu Phe Arg His Asp
            20                  25
```

<210> SEQ ID NO 65
<211> LENGTH: 34

```
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 65

Asp Ala Glu Phe Arg His Asp Asp Ala Glu Phe Arg His Asp Asp Ala
 1               5                  10                  15

Glu Phe Arg His Asp Pro Lys Tyr Val Lys Gln Asn Thr Leu Lys Leu
            20                  25                  30

Ala Thr

<210> SEQ ID NO 66
<211> LENGTH: 27
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 66

Asp Ala Glu Phe Arg His Asp Asp Ala Glu Phe Arg His Asp Pro Lys
 1               5                  10                  15

Tyr Val Lys Gln Asn Thr Leu Lys Leu Ala Thr
            20                  25

<210> SEQ ID NO 67
<211> LENGTH: 79
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 67

Asp Ala Glu Phe Arg His Asp Pro Lys Tyr Val Lys Gln Asn Thr Leu
 1               5                  10                  15

Lys Leu Ala Thr Glu Lys Lys Ile Ala Lys Met Glu Lys Ala Ser Ser
            20                  25                  30

Val Phe Asn Val Gln Tyr Ile Lys Ala Asn Ser Lys Phe Ile Gly Ile
        35                  40                  45

Thr Glu Leu Phe Asn Asn Phe Thr Val Ser Phe Trp Leu Arg Val Pro
    50                  55                  60

Lys Val Ser Ala Ser His Leu Glu Asp Ala Glu Phe Arg His Asp
 65                  70                  75

<210> SEQ ID NO 68
<211> LENGTH: 57
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 68

Asp Ala Glu Phe Arg His Asp Asp Ala Glu Phe Arg His Asp Asp Ala
 1               5                  10                  15

Glu Phe Arg His Asp Gln Tyr Ile Lys Ala Asn Ser Lys Phe Ile Gly
            20                  25                  30

Ile Thr Glu Leu Phe Asn Asn Phe Thr Val Ser Phe Trp Leu Arg Val
        35                  40                  45
```

```
Pro Lys Val Ser Ala Ser His Leu Glu
    50                  55

<210> SEQ ID NO 69
<211> LENGTH: 44
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 69

Asp Ala Glu Phe Arg His Asp Gln Tyr Ile Lys Ala Asn Ser Lys Phe
1               5                   10                  15

Ile Gly Ile Thr Glu Leu Cys Phe Asn Asn Phe Thr Val Ser Phe Trp
            20                  25                  30

Leu Arg Val Pro Lys Val Ser Ala Ser His Leu Glu
        35                  40

<210> SEQ ID NO 70
<211> LENGTH: 51
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 70

Asp Ala Glu Phe Arg His Asp Gln Tyr Ile Lys Ala Asn Ser Lys Phe
1               5                   10                  15

Ile Gly Ile Thr Glu Leu Cys Phe Asn Asn Phe Thr Val Ser Phe Trp
            20                  25                  30

Leu Arg Val Pro Lys Val Ser Ala Ser His Leu Glu Asp Ala Glu Phe
        35                  40                  45

Arg His Asp
    50

<210> SEQ ID NO 71
<211> LENGTH: 26
<212> TYPE: PRT
<213> ORGANISM: Artificial Sequence
<220> FEATURE:
<223> OTHER INFORMATION: Description of Artificial Sequence:synuclein
      fusion protein

<400> SEQUENCE: 71

Glu Gln Val Thr Asn Val Gly Gly Ala Ile Ser Gln Ala Val His Ala
1               5                   10                  15

Ala His Ala Glu Ile Asn Glu Ala Gly Arg
            20                  25

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence:Abeta 1-12
      peptide with inserted Cys residue

<400> SEQUENCE: 72

Asp Ala Glu Phe Arg His Asp Ser Gly Tyr Glu Val Cys
1               5                   10

<210> SEQ ID NO 73
```

```
<211> LENGTH: 6
<212> TYPE: PRT
<213> ORGANISM: Artificial Sequence
<220> FEATURE:
<223> OTHER INFORMATION: Description of Artificial Sequence:Abeta 1-5
      peptide with inserted Cys residue

<400> SEQUENCE: 73

Asp Ala Glu Phe Arg Cys
  1               5

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence:Abeta 33-42
      peptide with inserted Cys residue
<221> NAME/KEY: MOD_RES
<222> LOCATION: (2)
<223> OTHER INFORMATION: Xaa = amino-heptanoic acid

<400> SEQUENCE: 74

Cys Xaa Gly Leu Met Val Gly Gly Val Val Ile Ala
  1               5                  10

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence:Abeta 13-28
      peptide with two Gly residues added and inserted Cys residue
<221> NAME/KEY: MOD_RES
<222> LOCATION: (1)
<223> OTHER INFORMATION: Xaa = N-acetyl His

<400> SEQUENCE: 75

Xaa His Gln Lys Leu Val Phe Phe Ala Glu Asp Val Gly Ser Asn Lys
  1               5                  10                  15

Gly Gly Cys

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence:linker

<400> SEQUENCE: 76

Glu Gly Glu Gly
  1

<210> SEQ ID NO 77
<211> LENGTH: 22
<212> TYPE: PRT
<213> ORGANISM: Artificial Sequence
<220> FEATURE:
<223> OTHER INFORMATION: Description of Artificial Sequence:fusion
      protein with Abeta epitope

<400> SEQUENCE: 77

Asp Ala Glu Phe Arg His Asp Gln Tyr Ile Lys Ala Asn Ser Lys Phe
  1               5                  10                  15

Ile Gly Ile Thr Glu Leu
            20
```